(12) United States Patent
Chilkoti et al.

(10) Patent No.: US 11,458,205 B2
(45) Date of Patent: Oct. 4, 2022

(54) GENETICALLY ENCODED INTRINSICALLY DISORDERED STEALTH POLYMERS FOR DELIVERY AND METHODS OF USING SAME

(71) Applicant: Duke University, Durham, NC (US)

(72) Inventors: Ashutosh Chilkoti, Durham, NC (US); Samagya Banskota, Durham, NC (US); Parisa Yousefpour, Durham, NC (US); Jayanta Bhattacharyya, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/749,797

(22) PCT Filed: Aug. 4, 2016

(86) PCT No.: PCT/US2016/045655
§ 371 (c)(1),
(2) Date: Feb. 2, 2018

(87) PCT Pub. No.: WO2017/024182
PCT Pub. Date: Feb. 9, 2017

(65) Prior Publication Data
US 2018/0228908 A1    Aug. 16, 2018

Related U.S. Application Data

(60) Provisional application No. 62/200,726, filed on Aug. 4, 2015.

(51) Int. Cl.
| | | |
|---|---|---|
| A61K 47/64 | (2017.01) | |
| A61K 39/395 | (2006.01) | |
| A61K 39/00 | (2006.01) | |
| C07K 7/06 | (2006.01) | |
| A61P 35/00 | (2006.01) | |
| A61K 38/00 | (2006.01) | |
| A61K 47/60 | (2017.01) | |
| A61K 47/10 | (2017.01) | |
| C12N 15/70 | (2006.01) | |
| A61K 31/337 | (2006.01) | |

(52) U.S. Cl.
CPC .............. *A61K 47/64* (2017.08); *A61K 39/00* (2013.01); *A61K 39/395* (2013.01); *A61K 47/10* (2013.01); *A61K 47/60* (2017.08); *A61P 35/00* (2018.01); *C07K 7/06* (2013.01); *C12N 15/70* (2013.01); *A61K 31/337* (2013.01); *A61K 38/00* (2013.01); *A61K 2039/6031* (2013.01)

(58) Field of Classification Search
CPC ...... A61K 51/00; A61K 51/08; A61K 51/088; A61K 47/00; A61K 47/48; A61K 47/64; A61K 39/00; A61K 39/395; A61K 47/60; A61K 47/10; A61K 31/337; A61K 2039/6031; A61K 2121/00; A61K 2123/00; C07K 7/06; C07K 2319/01; A61P 35/00; C12N 15/70
USPC ........ 424/1.11, 1.49, 1.65, 1.69, 1.73, 1, 81, 424/1.85, 1.89, 9.1, 9.2, 9.3, 9.4, 9.5, 9.6; 514/1, 1.1, 19.2, 19.3, 19.4, 19.5, 19.6, 514/20.9, 21.1, 21.2, 21.3, 21.4, 21.5, 514/21.6, 21.7, 21.8; 530/300, 317, 324, 530/325, 326, 327, 328, 329, 330
See application file for complete search history.

(56) References Cited

U.S. PATENT DOCUMENTS

| | | |
|---|---|---|
| 4,415,732 A | 11/1983 | Caruthers et al. |
| 4,458,066 A | 7/1984 | Caruthers et al. |
| 4,500,707 A | 2/1985 | Caruthers et al. |
| 4,554,101 A | 11/1985 | Hopp |
| 4,668,777 A | 5/1987 | Caruthers et al. |
| 4,973,679 A | 11/1990 | Caruthers et al. |
| 4,976,734 A | 12/1990 | Urry et al. |
| 5,153,319 A | 10/1992 | Caruthers et al. |
| 5,250,516 A | 10/1993 | Urry |
| 5,278,302 A | 1/1994 | Caruthers et al. |
| 5,336,256 A | 8/1994 | Urry |
| 5,453,496 A | 9/1995 | Caruthers et al. |
| 5,534,408 A | 7/1996 | Green et al. |
| 5,578,577 A | 11/1996 | Ching et al. |
| 5,580,859 A | 12/1996 | Feigner et al. |
| 5,602,244 A | 2/1997 | Caruthers et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Feigner et al. |
| 5,935,776 A | 8/1999 | Green et al. |

(Continued)

FOREIGN PATENT DOCUMENTS

| | | |
|---|---|---|
| AU | 2007265628 B2 | 12/2012 |
| CA | 2327325 A1 | 11/1999 |

(Continued)

OTHER PUBLICATIONS

Frandsen et al., Chem. Soo. Rev., vol. 41, pp. 2696-2706 (Year: 2012).*

(Continued)

*Primary Examiner* — D. L. Jones
(74) *Attorney, Agent, or Firm* — Michael Best & Friedrich LLP

(57) ABSTRACT

Provided herein are conjugates including a polypeptide and one or more drug molecules. The polypeptide includes one or more charged motifs, and may further include one or more uncharged motifs. The conjugates may be used to effectively deliver the drug molecule to a subject.

23 Claims, 22 Drawing Sheets
Specification includes a Sequence Listing.

(56) References Cited

U.S. PATENT DOCUMENTS

| | | |
|---|---|---|
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,245,515 B1 | 6/2001 | Vogelstein et al. |
| 6,296,831 B1 | 10/2001 | Weller et al. |
| 6,302,874 B1 | 10/2001 | Zhang et al. |
| 6,413,587 B1 | 7/2002 | Hawker et al. |
| 6,512,060 B1 | 1/2003 | Matyjaszewski et al. |
| 6,541,580 B1 | 4/2003 | Matyjaszewski et al. |
| 6,623,950 B1 | 9/2003 | Osten et al. |
| 6,649,138 B2 | 11/2003 | Adams et al. |
| 6,660,247 B1 | 12/2003 | Gutowska et al. |
| 6,841,617 B2 | 1/2005 | Jeong et al. |
| 6,852,834 B2 | 2/2005 | Chilkoti |
| 6,869,588 B2 | 3/2005 | Weller et al. |
| 7,033,571 B2 | 4/2006 | Gutowska et al. |
| 7,087,244 B2 | 8/2006 | Jeong et al. |
| 7,300,922 B2 | 11/2007 | Sullenger et al. |
| 7,429,458 B2 | 9/2008 | Chilkoti |
| 7,531,524 B2 | 5/2009 | Rusconi |
| 7,664,545 B2 | 2/2010 | Westersten et al. |
| 7,674,882 B2 | 3/2010 | Kaplan et al. |
| 8,129,330 B2 | 3/2012 | Martinez et al. |
| 8,283,125 B2 | 10/2012 | Cebolla Ramirez et al. |
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,586,347 B2 | 11/2013 | Lochhead et al. |
| 8,841,414 B1 | 9/2014 | Raucher et al. |
| 8,912,310 B2 | 12/2014 | Chilkoti et al. |
| 8,937,153 B2 | 1/2015 | Abrahmsén et al. |
| 9,127,047 B2 | 9/2015 | Chilkoti |
| 9,132,178 B2 * | 9/2015 | Philip .............. G01N 33/57423 |
| 9,138,743 B2 | 9/2015 | Yager et al. |
| 9,482,664 B2 | 11/2016 | Chilkoti et al. |
| 9,592,303 B2 | 3/2017 | Chilkoti et al. |
| 9,771,396 B2 | 9/2017 | Chilkoti et al. |
| 9,804,170 B2 | 10/2017 | Krishna et al. |
| 9,890,420 B2 | 2/2018 | Chilkoti et al. |
| 10,064,954 B2 | 9/2018 | Wu |
| 10,131,690 B2 | 11/2018 | Bonny et al. |
| 10,302,636 B2 | 5/2019 | Chilkoti et al. |
| 10,364,451 B2 | 7/2019 | Chilkoti et al. |
| 10,385,115 B2 | 8/2019 | Chilkoti et al. |
| 10,434,182 B2 | 10/2019 | Weng et al. |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0008308 A1 | 1/2003 | Enzelberger et al. |
| 2003/0138829 A1 | 7/2003 | Unger et al. |
| 2003/0175290 A1 | 9/2003 | Renner et al. |
| 2003/0185741 A1 | 10/2003 | Matyjaszewski et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1 | 9/2004 | Snow et al. |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2009/0215194 A1 | 8/2009 | Magni et al. |
| 2010/0015070 A1 | 1/2010 | Bollschweiler et al. |
| 2010/0022455 A1 | 1/2010 | Chilkoti |
| 2010/0048473 A1 | 2/2010 | Chaikof et al. |
| 2010/0120018 A1 | 5/2010 | Quake et al. |
| 2010/0241054 A1 | 9/2010 | Dacey et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0119778 A1 | 5/2011 | Liss |
| 2011/0165557 A1 | 7/2011 | Ah et al. |
| 2011/0207673 A1 | 8/2011 | Chilkoti et al. |
| 2011/0248698 A1 | 10/2011 | Kikuchi et al. |
| 2011/0294189 A1 | 12/2011 | Chilkoti et al. |
| 2011/0303303 A1 | 12/2011 | Proper et al. |
| 2011/0305718 A1 | 12/2011 | Mugica et al. |
| 2012/0121709 A1 | 5/2012 | Chilkoti et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0197359 A1 | 8/2013 | Park et al. |
| 2013/0281624 A1 | 10/2013 | Chilkoti et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matem et al. |
| 2016/0209356 A1 | 7/2016 | Herget et al. |
| 2016/0220727 A1 | 8/2016 | Lu et al. |
| 2016/0250165 A1 | 9/2016 | Sullenger et al. |
| 2016/0271262 A1 | 9/2016 | Lopez et al. |
| 2016/0303091 A1 | 10/2016 | Wang |
| 2016/0348147 A1 | 12/2016 | Lopez et al. |
| 2016/0355802 A1 | 12/2016 | Isaacs et al. |
| 2017/0088670 A1 | 3/2017 | Rowan et al. |
| 2017/0102357 A1 | 4/2017 | Liang et al. |
| 2017/0166621 A1 | 6/2017 | Boettcher et al. |
| 2017/0170142 A1 | 6/2017 | Edelstein et al. |
| 2017/0189545 A1 | 7/2017 | Lee et al. |
| 2017/0233714 A1 | 8/2017 | Chilkoti et al. |
| 2017/0239363 A1 | 8/2017 | Chilkoti et al. |
| 2017/0369651 A1 | 12/2017 | Cheng et al. |
| 2018/0135060 A1 | 5/2018 | Romero Ramos et al. |
| 2018/0161772 A1 | 6/2018 | Rammohan et al. |
| 2018/0171337 A1 | 6/2018 | O'Neill et al. |
| 2018/0200196 A1 | 7/2018 | Fahmy et al. |
| 2018/0217136 A1 | 8/2018 | Chilkoti et al. |
| 2018/0231469 A1 | 8/2018 | Gibbons et al. |
| 2018/0238864 A1 | 8/2018 | Burd et al. |
| 2018/0326044 A1 | 11/2018 | Carter |
| 2018/0327752 A1 | 11/2018 | Pillay et al. |
| 2019/0016763 A1 | 1/2019 | Kitazawa et al. |
| 2019/0204309 A1 | 7/2019 | Gibbs |
| 2019/0285623 A1 | 9/2019 | Chilkoti et al. |
| 2019/0292549 A1 | 9/2019 | Zhang et al. |
| 2019/0345228 A1 | 11/2019 | Chilkoti et al. |
| 2020/0078313 A1 | 3/2020 | Roy et al. |
| 2020/0121809 A1 | 4/2020 | Hope et al. |
| 2020/0148724 A1 | 5/2020 | Chilkoti et al. |
| 2020/0163878 A1 | 5/2020 | Baumhof et al. |

(56) References Cited

U.S. PATENT DOCUMENTS

| | | |
|---|---|---|
| 2020/0181555 A1 | 6/2020 | Hinojosa et al. |
| 2021/0154143 A1 | 5/2021 | Chilkoti et al. |

FOREIGN PATENT DOCUMENTS

| | | |
|---|---|---|
| CA | 2423488 A1 | 4/2002 |
| CN | 104725628 B | 4/2018 |
| EP | 1670315 B1 | 4/2017 |
| EP | 2664340 B1 | 2/2020 |
| JP | 2014-156428 A | 8/2014 |
| JP | 2014-534265 A | 12/2014 |
| WO | WO1991/019813 A1 | 12/1991 |
| WO | WO 2003/040165 A2 | 10/2002 |
| WO | WO 2004/096124 A2 | 11/2004 |
| WO | WO 2006/004778 A2 | 1/2006 |
| WO | 2006/110292 A2 | 10/2006 |
| WO | WO 2007/073486 A2 | 6/2007 |
| WO | WO 2007/108013 A2 | 9/2007 |
| WO | WO 2007/134245 A2 | 11/2007 |
| WO | 2008/012543 A1 | 1/2008 |
| WO | 2008/030968 A2 | 3/2008 |
| WO | WO 2009/067584 A1 | 5/2009 |
| WO | WO 2010/054699 A1 | 5/2010 |
| WO | WO 2010/057154 A1 | 5/2010 |
| WO | WO 2010/096422 A1 | 8/2010 |
| WO | 2011/025572 A1 | 3/2011 |
| WO | WO 2011/123813 A2 | 10/2011 |
| WO | 2012/162426 A1 | 11/2012 |
| WO | WO2013/049234 A2 | 4/2013 |
| WO | WO 2013/065009 A1 | 5/2013 |
| WO | WO2013/106715 A1 | 7/2013 |
| WO | WO2014/037373 A1 | 3/2014 |
| WO | WO 2014/194244 A1 | 12/2014 |
| WO | 2015/011231 A1 | 1/2015 |
| WO | WO 2015/130846 A2 | 9/2015 |
| WO | WO 2016/065273 A1 | 4/2016 |
| WO | WO2016/065300 A1 | 4/2016 |
| WO | WO 2016/090103 A1 | 6/2016 |
| WO | WO 2016/154530 A1 | 9/2016 |
| WO | WO 2017/015132 A1 | 1/2017 |
| WO | WO 2017/024182 A1 | 2/2017 |
| WO | WO 2017/112825 A2 | 6/2017 |
| WO | WO 2017/112826 A2 | 6/2017 |
| WO | 2017/192449 A1 | 11/2017 |
| WO | WO2018/115401 A1 | 6/2018 |
| WO | WO 2018/144854 A1 | 8/2018 |
| WO | WO2019/103744 A1 | 5/2019 |
| WO | 2019/147954 A1 | 8/2019 |
| WO | 2020/037214 A1 | 2/2020 |
| WO | WO2020/160472 A1 | 8/2020 |

OTHER PUBLICATIONS

Abbruzzese et al., "A phase I clinical, plasma, and cellular pharmacology study of gemcitabine," J. Clin Oncol. 1991, 3, 491-498.

Aladini et al., "Chemical Synthesis and Characterization of Elastin-Like Polypeptides (ELPs) With Variable Guest Residues," J Pept Sci, 2016, 22(5):334-342.

Alconcel et al., "FDA-approved poly(ethylene glycol)-protein conjugate drugs," Polym. Chem. 2, 2011, 1442-1448.

Alley et al., "Feasibility of drug screening with panels of human tumor cell tines using a microculture tetrazolium assay," Cancer Res., 1988, 48, 589-601.

Aluri et al., "Elastin-like peptide amphiphiles Form nanofibers with tunable length," Biomacromolecules, 2012, 13, 2645-2654.

Amiram et al., "A depot-forming glucagon-like peptide-1 fusion protein reduces blood glucose for five days with a single injection," J. Control. Release, 2013, 172, 144-151.

Amiram et al., "Injectable protease-operated depots of glucagon-like peptide-1 provide extended and tunable glucose control," Proc. Natl. Acad. Sci. 110, 2013, 2792-2797.

Antos et al., "Lipid Modification of Proteins through Sortase-Catalyzed Transpeptidation," J. Am. Chem. Soc. 2008, 130, 16338-16343.

Antos et al., "Site-Specific N- and C-Terminal Labeling of a Single Polypeptide Using Sortases of Different Specificity," J. Am. Chern Soc. 2009, 131, 10800-10801.

Arias et al., "Superior preclinical efficacy of gemcitabine developed as chitosan nanoparticulate system," Biomacromolecules 2011, 12, 97-104.

Armstrong et al., "Antibody against poly(ethylene glycol) adversely affects PEG-asparaginase therapy in acute lymphoblastic leukemia patients," Cancer 110, 2007, 103-111.

Armstrong et al., "The Hydrodynamic Radii of Macromolecules and Their Effect on Red Blood Cell Aggregation," Biophys. J., 2004, 87, 4259-4270.

Arnida et al., "Geometry and surface characteristics of gold nanoparticles influence their biodistribution and uptake by macrophages," Eur J Pharm Biopharm, 2011, 77, 417-423.

Averick et al., "ATRP under biologically relevant conditions: grafting from a protein," ACS Macro. Lett. 1, 2012, 6-10.

Averick et al., "Protein-polymer hybrids: conducting ARGET ATRP from a genetically encoded cleavable ATRP initiator," Eur. Polym. J. 49, 2013, 2919-2924.

Awai et al., "Studies of the metabolism of 1-131-labeled human transferrin," J. Lab. Clin. Med. 61, 1963, 363-396.

Axup et al., "Synthesis of site-specific antibody-drug conjugates using unnatural amino acids," Proc Natl Acad Sci USA, 2012, 109(40):16101-16106.

Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.

Banga et al., "Parenteral controlled delivery and parmacokinetics of therapeutic peptides and proteins," (CRC Press, Boca Raton, FL, 2005).

Bansal et al., "PEGylation improves pharmacokinetic profile, liver uptake and efficacy of Interferon gamma in liver fibrosis," J. Control. Release 2011, 154, 233-240.

Bedford et al., "WW do main-mediated interactions reveal a spliceosome-associated protein that binds a third class of proline-rich motif: The proline glycine and methionine-rich motif," PNAS, 1998, 95: 10602-10607.

Bellucci et al., "A noncanonical function of sortase enables site-specific conjugation of small molecules to lysine residues in proteins," Angew. Chem. Int. Ed. 54, 2015, 441-445.

Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, 2013, 52(13):3703-3708.

Bender et al., "Synthesis, Crystallization, and Biological Evaluation of an Orally Active Prodrug of Gemcitabine," J. Med. Chem. 2009, 52, 6958-6961.

Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.

Berndt et al., "Synthetic lipidation of peptides and amino acids: Monolayer structure and properties," J. Am Chem. Soc., 1995, 117, 9515-9522.

Bessa et al., "Thermoresponsive self-assembled elastin-based nanoparticles for delivery of BMPs," Journal of Controlled Release, 2010, 142, 312-318.

Bhattacharyya et al., "A paclitaxel-loaded recombinant polypeptide nanoparticle outperforms Abraxane in multiple murine cancer models," Nat. Commun. 2015, 6, 7939.

Bidwell et al., "Development of elastin-like polypeptide for thermally targeted delivery of doxorubicin," Biochemical Pharmacology, 2007, 73(5):620-631.

Boekhorst et al., "Genome-wide detection and analysis of cell wall-bound proteins with LPxTG-like sorting motifs," J. Bacteriol. 187, 2005, 4928-4934.

Bond, "Exenatide (Byetta) as a novel treatment option for type 2 diabetes mellitus," Proc. (Bayl. Univ. Med. Cent.) 19, 2006, 281-284.

(56) References Cited

OTHER PUBLICATIONS

Bontempo et al., "Streptavidin as a macroinitiator for polymerization: in situ protein-polymer conjugate formation," J. Am. Chem. Soc., 2005, 6508-6509.
Boyer et al., "Well-Defined Protein-Polymer Conjugates via in Situ RAFT Polymerization," J. Am. Chem. Soc. 2007, 129, 7145-7154.
Broyer et al., "Emerging synthetic approaches for protein-polymer conjugations," Chem. Commun. 2011, 47, 2212.
Brusa et al., "Antitumor activity and pharmacokinetics of liposomes containing lipophilic gemcitabine prodrugs," Anticancer Res. 2007, 27, 195-199.
Cai et al., "Long-acting preparations of exenatide," Drug Des. Dev. Ther. 7, 2013, 963-970.
Caliceti et al., "Pharmacokinetic and biodistribution properties of poly(ethylene glycol)-protein conjugates," Adv. DrugDeliv. Rev, 2003, 55, 1261-1277.
Campbell et al., "Pegylated peptides V. Carbo xy-terminal PEGlyted analogs of growth hormone-releasing factor (GRF) display enhanced duration of biological activity in vivo," J. Peptide Res., 1997, 49:527-537.
Carrico et al., "Introducing genetically encoded aldehydes into proteins," Nat Chem Biol, 2007, 3(6):321-322.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers To Probe the Mechanism of Elastin Elasticity," J. Am Chem. Soc., 2009, 132(13):4577-4579.
Chen et al., "Site-specific labeling of cell surface proteins with biophysical probes using biotin ligase," Nat Methods, 2005, 2(2):99-104.
Chilkoti et al., "Design of thermally responsive, recombinant polypeptide carriers for targeted drug delivery," Advance Drug Delivery Reviews, 2002, 54:1093-1111.
Chilkoti et al., "Targeted drug delivery by thermally responsive polymers," Advanced Drug Delivery Reviews, 2002, 54:613-630.
Chithrani et al., "Determining the size and shape dependence of gold nanoparticle uptake into mammalian cells," Nano Lett, 2006, 6, 662-668.
Chitkara et al., "Self-Assembling, Amphiphilic Polymer-Gemcitabine Conjugate Shows Enhanced Antitumor Efficacy Against Human Pancreatic Adenocarcinoma," Bioco njug. Chem. 2013, 24, 1161-1173.
Cho et al., "Effects of hofmeister anions on the phase transition temperature of elastin-like polypeptides," J. Phys. Chem. B., 2008, 112, 13765-13771.
Cho et al., "Therapeutic nanoparticles for drug delivery in cancer," Clin. Cancer Res., 2008, 14, 1310-1316.
Chow et al., "Peptide-based biopolymers in biomedicine and biotechnology," Mater. Sci. Eng. R Reports, 2008, 62, 125-155.
Chow et al., "Ultra-High Expression of a Thermally Responsive Recombinant Fusion Protein in E. coli," Biotechnology Progress, 2006, 22(3):638-646.
Christensen et al., "Fusion order controls expression level and activity of elastin-like polypeptide fusion proteins," Protein Science, 2009, 18:1377-1387.
Coin et al., "Solid-phase peptide synthesis: from standard procedures to the synthesis of difficult sequences," Nat. Protoc., 2007, 2, 3247.
Craik et al., "The future of peptide-based drugs," Chemical biology & drug design 81, 2013, 136-147.
Cui et al., "Amino acid sequence in constitutionally isomeric tetrapeptide amphiphiles dictates architecture of one-dimensional nanostructures," J. Am. Chem. Soc., 2014, 136, 12461-12468.
Cui et al., "Self-assembly of peptide amphiphiles: from molecules to nanostructures to biomaterials," Biopolymers, 2010, 94, 1-18.
Dalla Poza et al., "Targeting gemcitabine containing liposomes to CD44 expressing pancreatic adenocarcinoma cells causes an increase in the antitumoral activity," Biochim. Biophys. Acta, 2013, 1828, 1396-1404.

Dasgupta et al., "Isopeptide Ligation Catalyzed by Quintessential Sortase A: Mechanistic Cues From Cyclic and Branched Oligomers of Indolicidin," The Journal of Biological Chemistry, 2011, vol. 286, No. 27, pp. 23996-24006, Supplemental Information.
De et al., "Temperature-Regulated Activity of Responsive Polymer-Protein Conjugates Prepared by Grafting-from via RAFT Polymerization," J. Am. Chem. Soc. 2008, 130, 11288-11289.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylationfor stabilizing biologies," Acta Biomater. 2009, 5, 560-569.
Diehl et al., "A Good Practice Guide to the Administration of Substances and Removal of Blood Including Routes and Volumes," J Appl Toxicol, 2001, 21, 15-23.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. 2008, 130, 687-694.
Dreher, M. R. Ph.D. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm, 2007, 341, 207-214.
Drucker et al., "The incretin system glucagon-like peptide-1 receptor agonists and dipeptidyl peptidase-4 inhibitors in type 2 diabetes," Lancet 368, 2006, 1696-1705.
Drucker, "Glucagon-like peptides," Diabetes 47, 1998, 159-169.
Du et al., "Tailor-made dual pH-sensitive polymer-doxorubicin nanoparticles for efficient anticancer drug delivery," J. Am Chem. Soc., 2011, 133, 17560-17563.
Duan et al., "Fibronectin type III do main based monobody with high activity," Biochemistry, 2007 46(44):12656-12664.
Dubey et al., "Development and evaluation of folate functionalized albumin nanoparticles for targeted delivery of gemcitabine," Int J Pharm, 2015, 492(1-2):80-91.
Duncan, R. "Polymer conjugates as anticancer nanomedicines," Nat. Rev. Cancer 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Eisenhaber et al., "Prediction of lipid posttranslational modifications and localization signals from protein sequences: Big-II, NMT and PTS1," Nucleic Acids Res., 2003, 31, 3631-3634.
Etrych et al., "HPMA Copolymer Conjugates of Paclitaxe; and Docetaxel withpH-Controlled Drug Release," Molecular Pharmaceutics, 2010, 7(4): 1015-1026.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Feng et al., "Protein resistant surfaces: comparison of acrylate graft polymers bearing oligo-ethylene oxide and phosphorylcholine side chains," Biointerphases, 2006, 1 (1), 50.
Flue gel et al., "Chain stiffness of elastin-like polypeptides," Biomacromolecules 2010, 11, 3216-3218.
Friedman et al., "Directed Evolution to Low Nano molar Affinity of a Tumor-Targeting Epidermal Growth Factor Receptor-Binding Affibody Molecule," J. Mol. Biol., 2008, 376, 1388-1402.
Furgeson et al., "Structural optimization of a "smart" doxorubicin-polypeptide conjugate for thermally targeted delivery to solid tumors," Journal of Controlled Release, 2006, 110:362-369.
Gaberc-Porekar et al., "Obstacles and pitfalls in the PEGylationof therapeutic proteins," Curr. Opin DrugDiscov. Devel. 11, 2008, 242-250.

(56) References Cited

OTHER PUBLICATIONS

Gabizon et al., "Prolonged circulation time and enhanced accumulation in malignant exudates of doxorubicin encapsulated in polyethylene-glycol coated liposomes," Cancer Res. 1994, 54, 987-992.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, 2006, R12-R22.
Ganson et al., "Pre-existing anti-PEG antibody linked to first-exposure allergic reactions to Pegnivacogin, a PEGylated RNA aptamer," J. Allergy Clin. Immunology, (2015).
Gao et al., "In situ growth of a PEG-like polymer from the C terminus of an intein fusion protein improves pharmacokinetics and tumor accumulation" PNAS Early Edition, 2010, vol. 107, 1-6.
Gao et al., "In situ growth of a PEG-like polymer from the C terminus of an intein fusion protein improves pharmacokinetics and tumor accumulation," Proc. Natl. Acad. Sci. 107, 2010, 16432-16437.
Gao et al., "In situ growth of a stoichiometric PEG-like conjugate at a protein's N-terminus with significantly improved pharmacokinetics," Proc. Natl. Acad. Sci., 2009,15231-15236.
Garanger et al., "Structural Evolution of a Stimulus-Responsive Diblock Polypeptide Micelle by Temperature Tunable Compaction of its Core," Macromolecules, 2015, 48, 6617-6627.
Garay et al., "Antibodies against polyethylene glycol in healthy subjects and inpatients treated withPEG-conjugated agents," Expert Opinion DrugDeliv. 9, 2012, 1319-1323.
Gauthier et al., "Peptide/protein-polymer conjugates: synthetic strategies and design concepts," Chem. Commun., 2008, 2591-2611.
Ge et al., "Self-Cleavable Stimulus Responsive Tags for Protein Purification without Chromatography" J. Am. Chem. Soc., 2005, 127: 11228-11229.
Genbank AccessionNM_001182082.1 (2017).
Gibson et al., "Enzymatic assembly of DNA molecules up to several hundred kilobases," Nat Methods, 2009, 6, 343-345.
Gluck et al., "Single Vector System for Efficient N-myristoylation of Recombinant Proteins in *E. coli*," Pios One. 2010, 5(4) e100881.
Goke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Gordon et al., "Protein N-myristoylation," J. Biol. Chem., 1991, 266, 8647-8650.
Goutelle et al., "The Hill equation: a review of its capabilities in pharmacological modelling. Fundam," Clin Pharmacol. 22, 2008, 633-648.
Green et al., "Novel dipeptidyl peptidase IV resistant analogues of glucagon-like peptide-1(7-36)amide have preserved biological activities in vitro conferring improved glucose-lowering action in vivo" J. of Mol. Endocrin, 2003, 31(3): 529-540.
Greenfield, "Using circular dichroism spectra to estimate protein secondary structure," Nat. Protoc., 2006, 1(6):2876-90.
Grover et al., "Protein-Polymer Conjugates: Synthetic Approaches by Controlled Radical Polymerizations & Interesting Applications", Curr Opin Chem Bioi., Dec. 2010; 14(6): 818-827.
Haider et al., "Genetically engineered polymers: Status and prospects for controlled release," J. Control. Release, 2004, 95, 1-26.
Hamidi et al., "Pharmacokinetic Consequences of Pegylation," DrugDeliv. 2006, 13, 399-409.
Hamley, "Self-assembly of amphiphilic peptides," Soft Matter, 2011, 7, 4122.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, 2015, 48, 4183-4195.
Hassouneh et al., "Elastin-Like Polypeptides as a Purification Tag for Recombinant Proteins," Curr Protoc Protein Sci., 2010, Chapter 6. Unit 6.11. 10.1002/0471140864.ps0611s61.
Hassouneh et al., "Fusions of elastin-like polypeptides to pharmaceutical proteins," Methods Enzymol., 2012, 502, 215-37.
Hassouneh et al., "Unexpected Multivalent Display of Proteins by Temperature Triggered Self-assembly of Elastinlike Polypeptide Block Copolymers," Biomacromolecules, 2012, vol. 13, Issue 4, pp. 1598-1605.
He et al., "Comparative genomics of elastin Sequence analysis of a highly repetitive protein," Matrix Biology, 2007, 26:524-540.
He et al., "Improving protein resistance of $\alpha$-Al2O3 membranes by modification with POEGMA brushes," Applied Surface Science, 2011, 258 (3), 1038-1044.
Heagerty et al., Biometrics, "Time-dependent ROC curves for censored survival data and a diagnostic marker," 2000, 56(2):337-44.
Heal et al., "N-Myristoyl transferase-mediated protein labelling in vivo," Org. Biomol. Cham., 2008, 6(13):2308-2315.
Heal et al., "Site-specific N-terminal labelling of proteins in vitro and in vivo using N-myristoyl transferase and bioorthogonal ligation chemistry," Chem. Commun., 2008, 3, 480-482.
Heredia et al., "In Situ Preparation of Protein-"Smart" Polymer Conjugates with Retention of Bioactivity," J. Am. Chem. Soc. 2005, 127, 16955-16960.
Hershfield et al., "Induced and pre-existing anti-polyethylene glycol antibody in a trial of every 3-week dosing of pegloticase for refractory gout, including in organ transplant recipients," Arthritis Res. Ther. 16, 2014, R63.
Ho et al., "Chemoenzymatic Labeling of Proteins for Imaging in Bacterial Cells," J. Am. Chem. Soc., 2016, 138(46):15098-15101.
Hober et al., "Protein A chromatography for antibody purification," Journal of Chromatography B 848, 2007, pp. 40-47.
Hochkoeppler, "Expanding the landscape of recombinant protein production in *Escherichia coli*," Biotechnol. Lett., 2013,35, 1971-1981.
Holehouse et al., "CIDER: Classification of Intrinsically Disordered Ensemble Regions," Biophysical Journal, 2015, vol. 108, Issue 2, Supplement 1, p. 228a.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem, 2015, 7, 1-8.
Ishida et al., "Accelerated blood clearance (ABC) phenomenon upon repeated injection of PEGylated liposomes," International Journal of Pharmaceutics, 2008, 354(1-2):56-62.
Jakubowski et al., "Activators regenerated by electron transfer for atom-transfer radical polymerization of (meth)acrylates and related block copolymers," Angew. Chem. Int. Ed., 2006, 4482-4486.
Janes et al., "Chitosan nanoparticles as delivery systems for doxorubicin," J. Control Release, 2001, 73, 255-267.
Jia et al., "Preparation, physicochemical characterization and cytotoxicity in vitro of gemcitabine-loaded PEG-PDLLA nanovesicles," World J. Gastroenterol. 2010, 16(8):1008-1013.
Jiang et al., "The internal structure of self-assembled peptide amphiphiles nanofibers," Soft Matter, 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, 2009, 70 (1), 53-9.
Junutula et al., "Site-specific conjugation of a cytotoxic drug to an antibody improves the therapeutic index," Nat Biotechnol, 2008, 26(8):925-932.
Kanoski et al., "The role of nausea in food intake and body weight suppression by peripheral GLP-1 receptor agonists, exendin-4 and liraglutide," Neuropharmacology 62, 2012, 1916-1927.
Katti et al., "Amino acid repeat patterns inprotein sequences: Their diversity and structural-functional implications," Protein Science, 2000, 9: 1203-1209.

(56) References Cited

OTHER PUBLICATIONS

Keefe et al., "Poly(zwitterionic)protein conjugates offer increased stability without sacrificing binding affinity or bioactivity," Nat Chem, 2012, 4(1):59-63.
Keller et al., "Empirical Statistical Model To Estimate the Accuracy of Peptide Identifications Made by MS/MS and Database Search," Anal. Chem. 2002, 74, 5383-5392.
Kelly et al., "How to study proteins by circular dichroism," Biochim Byophys. Acta—Proteins Proteomics, 2005, 1751(2):119-39.
Khandare et al., "Polymer-drug conjugates: Progress in polymeric drugs," Prog. Polym. Sci., 2005, vol. 31, pp. 359-397.
Kim et al., "Site-Specific PEGylated Exendin-4 Modified with a High Molecular Weight Tri meric PEG Reduces Steric Hindrance and Increases Type 2 Antidiabetic Therapeutic Effects," Bioconjugate Chem. 2012, 23, 2214-2220.
Kim et al., "Ultrasensitive Carbon nanotube-based biosensors using antibody-binding fragments," Analytical Biochemistry, 2008, 381, 193-198.
Knop et al., "Poly(ethylene glycol) in Drug Delivery: Pros and Cons as Well as Potential Alternatives," Angewandte Chemie International Edition, 2010, 49(36):6288-6308.
Knudsen, "Glucagon-like Peptide-1: The Basis ofaNew Class of Treatment for Type 2 Diabetes" J. Med. Chem, 2004, 47:4128-4134.
Kobashigawa et al., "Attachment Of An NMR-lnvisible Solubility Enhancement Tag Using A Sortase-Mediated Protein Ligation Method," J Biomol NMR. Mar. 2009, vol. 43, No. 3; pp. 145-150.
Kontos et al., "Drug development: longer-lived proteins," Chemical Society Reviews, 2012, 41(7):2686-2695.
Kothare et al., "Pharmacokinetics, pharmacodynamics, tolerability, and safety of exenatide in Japanese patients with type 2 diabetes mellitus," J. Clin. Pharmacol. 48, 2008, 1389-1399.
Kramer et al., "Quantitative Side-Chain Modifications of Methionine-Containing Elastin-Like Polypeptides as a Versatile Tool to Tune Their Properties," ACS Macro Lett., 2015, 4(11):1283-1286.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem, 2015, 26(10):2153-2160.
Kulkarni et al., "Selective functionalization of the protein N terminus withN-myristoyl transferase for bioconjugation in cell lysate," ChemBioChem, 2013, 14, 1958-1962.
Kumar et al., "N-Terminal Region of the Catalytic Domain of Human N-Myristoyl transferase 1 Acts as an Inhibitory Module," PLoS One, 2015, 10(5):e0127661.
Kyte et al., "A Simple Method for Displaying the Hydropathic Character of a Protein," J. Mol. Biol., 1982, 157:105-132.
Langer et al., "Designing materials for biology and medicine," Nature, 2004, 428, 487-92.
Le Droumaguet et al., "Recent advances in the design of bioconjugates from co ntrolled/living radical polymerization," Polym. Chem. 2010, 1, 563-598.
Le Meins et al., "Hybrid polymer/lipid vesicles: State of the art and future perspectives," Mater. Today, 2013, 16, 397-402.
Leader et al., "Protein therapeutics: a summary and pharmacological clasification," Nat. Rev. Drug Discov. 7, 2008, 21-39.
Lee et al., "Atomistic molecular dynamics simulations of peptide amphiphile self-assembly into cylindrical nanofibers," J. Am. Chem. Soc., 2011, 133, 3677-3683.
Lee et al., "Theranostic nanoparticles with controlled release of gemcitabine for targeted therapy and MRI of pancreatic cancer," ACS Nano 2013, 7(3):2078-2089.
Lele et al., "Synthesis of uniform protein-polymer conjugates," Bio macro molecules 6, 2005, 3380-3387.
Lennen et al., "Membrane Stresses Induced by Overproduction of Free Fatty Acids in *Escherichia coli*," Appl EnvironMicrob., 2011, 77(22):8114-28.

Leung et al., "Bio-Click Chemistry: Enzymatic Functionalization of PEGylated Capsules for Targeting Applications**," Angew. Chem. Int. Ed. 2012, 51, 7132-7136.
LeVine et al., "Thioflavine T interaction with synthetic Alzheimer's disease beta-amyloid peptides: detection of amyloid aggregation in solution," Protein Sci., 1993, 2, 404-10.
Li et al., "Molecular description of the lest behavior of an elastin-like polypeptide," Biomacromolecules, 2014, 15, 3522-3530.
Li et al., "Protein adsorption on oligo(cthylcnc glycol)-terminated alkanethiolate self-assembled monolayers: The molecular basis for nonfouling behavior," The journal ofphysical chemistry. B, 2005, 109 (7), 2934-41.
Li et al., "Temperature-Triggered Phase Separation of a Hydrophilic Resilin-Like Polypeptide," Macramol. Rapid Commun, 2015, 36(1):90-95.
Liao et al., "Removal ofN-terminal methionine from recombinant proteins by engineered *E. coli* methionine aminopeptidase," Prot. Sci. 13, 2004, 1802-1810.
Liechty et al., "Polymers for Drug Delivery Systems," Annual review of chemical and biomolecular engineering, 2010, 1:149-173.
Lim et al., "Improved Non-Chromatographic Purification of a Recombinant Proteinby Cationic Elastin-like Polypeptides" Biomacromolecules, 2007, 8(5): 1417-1424.
Lim et al., "In situ cross-linking of elastin-like polypeptide block copolymers for tissue repair," Biomacromolecules, 2008, 9, 222-230.
Lim et al., "In vivo post-translational modifications of recombinant mussel adhesive protein in insect cells," Biotechnol. Prog., 2011, 27, 1390-1396.
Linder et al., "Lipid Modifications of G Protein Subunits," J. Biol. Chem., 1991, 266(7):4654-4659.
Ling et al., "Protein thioester synthesis enabled by sortase," J. Am ChemSoc, 2012, 134(26):10749-10752.
Liu et al., "Hydrophobic modifications of cationic polymers for gene delivery," Prog. InPolym. Sci., 2010, 35, 1144-1162.
Liu et al., "In Situ Formation of Protein-Polymer Conjugates through Reversible Addition Fragmentation Chain Transfer Polymerization**," Angew. Chem. Int. Ed. 2007, 46, 3099-3103.
Liu et al., "Injectable intratumoral depot of thermally responsive polypeptide-radionuclide conjugates delays tumor progression in a mouse model," J. Control Release, 2010, 144(1):2-9.
Livingstone, "Theoretical property predictions. CurrTopMed ChemFIELD Full Journal Tide: Current topics in medicinal chemistry," Curr. Top. Med. Chem. 2003, 3, 1171-1192.
Lovshin et al., "Incretin-based therapies for type 2 diabetes mellitus," Nat. Rev. Endocrinol. 5, 2009, 262-269.
Luginbuhl et al., "One-week glucose control via zero-order release kinetics from an injectable depot of glucagon-like peptide-1 fused to a thermosensitive biopolymer," Nat. Biomed. Eng., 2017, 1, 0078.
Luginbuhl et al., "Recombinant Synthesis of Hybrid Lipid-Peptide Polymer Fusions that Self-Assemble and Encapsulate Hydrophobic Drugs," Angew Chem Int Ed Engl., 2017, 56: 13979-13984.
Lukyanov et al., "Micelles FromLipid Derivatives of Water-Soluble Polymers as Delivery Systems for Poorly Soluble Drugs," Adv. Drug Deliver. Rev., 2004, 56(9): 1273-1289.
Lund et al., "Phase II study of gemcitabine (2',2'-difluorodeoxycytidine) in previously heated ovarian cancer patients," J. Natl. Cancer. Inst. 1994, 86(20):1530-1533.
Ma et al., "Non-fouling" oligo(ethylene glycol)-functionalized polymer brushes synthesized by surface-initiated atomtransfer radical polymerization, Advanced Materials 2004, 16 (4), 338.
Ma et al., "Protein-resistant polymer coatings on silicon oxide by surface-initiated atom transfer radical polymerization," Langmuir : the ACS journal of surfaces and colloids, 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, 2006, 16 (5), 640-648.
MacEwan et al., "Digital switching of local arginine density in a genetically encoded self-assembled polypeptide nanoparticle controls cellular uptake," Nano Lett., 2012, 12, 3322-3328.

(56) References Cited

OTHER PUBLICATIONS

MacEwan et al., "Elastin-like polypeptides: Biomedical applications of tunable biopolymers," Biopolymers, 2010, 94, 60-77.
MacEwan et al., "Non-chromato graphic Purification of Recombinant Elastin-like Polypeptides and their Fusions with Peptides and Proteins from *Escherichia coli*," 2014, 88, p. e51583.
MacEwan et al., "Phase Behavior and Self-Assembly of Perfectly Sequence-Defined and Monodisperse Multiblock Copolypeptides," Biomacromolecules, 2017, 18(2):599-609.
Mack et al., "Antiobesity action of peripheral exenatide (exendin-4) in rodents: effects on food intake, body weight, metabolic status and side-effect measures," Int. J. Obes. 30, 2006, 1332-1340.
Mackay et al., "Self-assembling chimeric polypeptide-doxorubicin conjugate nanoparticles the abolish tumors after single injection," Nat Mater, 2009, 8(12):993-999.
Maeda et al., "Tumor vascular permeability and the EPR effect in macromolecular therapeutics: a review," J. Control. Release, 2000, 65(1-2)271-284.
Magnusson et al., "In Situ Growthof Side-Chain PEG Polymers from Functionalized Human Growth Hormone—A New Technique for Preparation of Enhanced Protein-Polymer Conjugates," Bioconjugate Chem 21, 2010, 671-678.
Malik et al., "Recent advances inproteinand peptide drug delivery systems," Curr. Drug Deliv. 2, 2007, 141-151.
Mann et al., "Proteomic analysis of post-translational modifications," Nat. Biotechnol., 2003, 21, 255-61.
Mao et al., "Sortase-mediated protein ligation: a new method for protein engineering," J. Am Chem. Soc., 2004, 126(9):2670-2671.
Maraffini et al., "Sortases and the art of anchoring proteins to the envelopes of Gram—positive bacteria," Microbiol Mol Biol Rev, 2006, 70(1):192-221.
Marr et al., "Effect of Temperature onthe Composition of Fatty Acids in *Escherichia coli*," J Bacteriol., 1962, 84(6):1260-7.
Maskarinec et al., "Protein engineering approaches to biomaterials design," Curr. Opin Biotechnol., 2005, 16, 422-426.
Massey et al., "Self-Assembly of a Novel Organometallic—Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, 2015, 208:52-8.
Matsumura et al., "A new concept for macromolecular therapeutics in cancer chemotherapy: mechanismof tumoritropic accumulation of proteins and the antitumor agent smancs," Cancer Res. 1986, 46, 6387-6392.
Matyjaszewski et al., "Atom transfer radical polymerization," Chem. Rev. 101, 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the CollagenType IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.
McDaniel et al., "A unified model for de novo design of elastin-like polypeptides with tunable inverse transition temperatures," Biomacromolecules, 2013, 14(8):2866-2872.
McDaniel et al., "Drug delivery to solid tumors by elastin-like polypeptides," Adc. Drug Deliver. Rev., 2010, 62(15):1456-1467.

McDaniel et al., "Noncanonical Self-Assembly of Highly Asymmetric Genetically Encoded Polypeptide Amphiphiles into Cylindrical Micelles," Nano Lett, 2014, 14(11):6590-6598.
McDaniel et al., "Self-assembly of thermally responsive nanoparticles of a genetically encoded peptide polymer by drug conjugation," Chem. Int. Ed. 2013, 52, 1683-1687.
McDaniell, J.R. et al., "Recursive Directional Ligation by Plasmid Reconstruction Allows Rapid and Seamless Cloning of Oligomeric Genes," Biomacromolecules, 2010, 11(4):944-952.
McHale et al., "Synthesis and in vitro evaluation of enzymatically cross-linked elastin-like polypeptide gels for cartilaginous tissue repair," Tissue Eng, 2005, 11, 1768-1779.
McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
Mejuch et al., "Synthesis of lipidatedproteins," Bioconjug. Chem. 27, 2016, 1771-1783.
Mero et al., "Transglutaminase-mediated PEGylationof proteins: direct identification of the sites protein medificationby mass spectrometry using a novel monodisperse PEG," Bioconjug Chem, 2009, 20(2):384-389.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol.,1999, 17(11):1112-1115.
Meyer et al., "Quantification of the effects of chain length and concentration on the thermal behavior of elastin-like polypeptides," Biomacromolecules, 2004, 5(3):846-51.
Meyer et al., "Targeting a Genetically Engineered Elastin-Like Polypeptide to Solid Tumors by Local Hyperthermia," Cancer Res., 2001, 61(4):1548-1554.
Mosbach et al., "Formation of proinsulin by immobilized Bacillus subtilis," Nature, 1983, 302, 543-545.
Muiznies et al., "Modulated growth, stability and interactions of liquid-like coacervate assemblies of elastin," Matrix Biology 36, 2014, pp. 39-50.
Muralidharan et al., "Protein Ligation an Enabling Technology for the Biophysical Analysis ofProteins," Nature Methods, 2006, vol. 3, No. 6, pp. 429-438.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials 2014, 35(24):6482-6497.
Naim et al., "A Synthetic Resilin Is Largely Unstructured," Biophysical Journal, 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Neidigh et al., "Exendin-4 and glucagon-like-peptide-q: NMR structural comparisons in the solution and micelle-associated states," Biochemistry 40, 2001, 13188-13200.
Newcomb et al., "Advances in cryogenic transmission electron microscopy for the characterization of dynamic selfassembling nanostructures," Current Opinion in Colloid and Interface Science, 2012, 17, 350-359.
Nicolas et al., "Fluorescently tagged polymer bioconjugates from protein derived macroinitiators," Chem. Commun. 2006, 45, 4697-4699.
Nielsen, "Incretin mimetics and DPP-IV inhibitors for the treatment of type 2 diabetes," DrugDiscov. Today 10, 2005,703-710.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, 2008, 9, 2755-2763.
O'Day et al., "Therapeutic Protein-polymer Conjugates: Advancing beyond PEGylation," J. Am Chem Soc., 2014, vol. 136, pp. 14323-14332.

(56) References Cited

OTHER PUBLICATIONS

Ortony et al., "Internal dynamics of a supramolecular nanofibre," Nat. Mater., 2014, 13, 1-5.
Pace et al., "How to measure and predict the molar absorption coefficient of a protein" Protein Science 1995, 4:2411-2423.
Paiva et al., "Secretion of interferon by Bacillus subtilis," Gene, 1983, 22, 229-235.
Paolino et al., "Folate-targeted supramolecular vesicular aggregates as a new frontier for effective anticancer treatment in in vivo model," Eur. J. Pharm. Biopharm. 2012, 82(1):94-102.
Paolino et al., "Gemcitabine-loaded PEGylated unilamellar liposomes vs GEMZAR: biodistribution, pharmacokinetic features and invivo antitumor activity," J. Control. Release 2010, 144(2):144-150.
Papa et al., "PEGylated Liposomal Gemcitabine: Insights Into a Potential Breast Cancer Therapeutic," Cell Oncol. (Dordr) 2013, 36(6):449-457.
Paramonov et al., "Self-assembly of peptide-amphiphile nanofibers: The roles of hydro gen bonding and amphiphilic packing," J. Am. Chem. Soc., 2006, 128, 7291-7298.
Park et al., "Formulation optimization and invivo proof-of-concept study of thermosensitive liposomes balanced by phospholipid, elastin-tike polypeptide, and cholesterol," PLoS One, 2014, 9: e103116, 13 pages.
Parkes et al. "Discovery and development of exenatide: the first antidiabetic agent to leverage the multiple benefits of the incretin hormone, GLP-1," Expert Opinion. DrugDeliv. 8, 2012, 219-244.
Parveen et al., "Nanomedicine," Clinical Pharmacokinetics, 2006, 45(10):965-988.
Peeler et al., "Genetically encoded initiator for polymer growth from proteins," J. Am. Chem. Soc. 132, 2010, 13575-13577.
Peters, "Serumalbumin," Adv. Protein Chem 37, 1985, 161-245.
Petitdemange et al., "Tuning Thermoresponsive Properties of Cationic Elastin-like Polypeptides by Varying Counterions and Side-Chains," Bioconjug. Chem., 2017, 28(5): 1403-1412.
Pinkas et al., "Tunable, post-translational hydroxylation of collagen domains in *Escherichia coli*," ACS Chem. Biol., 2011, 6, 320-324.
Popp et al., "Site-specific labeling via sortase-mediated transpeptidation," Curr. Protoc. Protein Sci. 56, 2009, 15.13.1-15.13.9.
Popp et al., "Sortase-Catalyzed Transformations That Improve The Properties Of Cytokines," PNAS, 2011, vol. 108, No. 8, pp. 3169-3174.
Pulaski et al., "Mouse 4T1 breast tumor model," Curr. Protoc. Immunol., 2001, Chapter 20, Unit 20.2.
Qi et al., Dataset for A brush-polymer conjugate of exendin-4 reduces blood glucose for up to five days and eliminates poly(ethylene glycol) antigenicity. Figshare, 2016, <http://dx.doi.org/10.6084/m9.figshare.3976761> 28 pages.
Qi et al., "Growing polymers from peptides and proteins: abiomedical perspective," Polym Chem. 5, 2014, 266-276.
Qi et al., "Protein-polymer conjugation—movingbeyondPEGylation," Curr. Opin Chem. Biol. 28, 2015, 181-193.
Qi et al., "Sortase-catalyzed initiator attachment enables high yield growth of a stealth polymer from the C terminus of a protein," Macromol. Rapid Commun. 34, 2013, 1256-1260.
Qiu et al., "Polymer Architecture and Drug Delivery," Pharmaceutical Research, 2006, 23(1):1-30.
Quiroz et al., "Sequence heuristics to encode phase behaviour in intrinsically disordered protein polymers," Nat. Mater., 2015, 14, 1164-1171.
Radivojac et al., "Intrinsic Disorder and Functional Proteomics," Biophysical Journal, 2007, vol. 92, Issue 5, pp. 1439-1456.
Rapaka et al., "Coacervation of Sequential Polypeptide Models of Tropoelastin," Int J Peptide Protein Res, 1978, 11: 97-108.
Rauscher et al. "Proline and Glycine Control Protein Self-Organization into Elastomeric or Amyloid Fibrils," Structure, 2006, 14:1667-1676.
Richards et al., "Engineered fibronectin type III domain with a RGDWE sequence binds with enhanced affinity and specificity to human $\alpha v\beta 3$ integrin," J Mol Biol, 2003, 326(5):1475-1488.

Riddles et al., "Ellman's reagent: 5,5'-dithiobis(2-nitrobenzoic acid)—a reexamination," Anal Biochem 1979, 94(1):75-81.
Ritcher et al., "Antibodies against polyethylene glycol produced in animals by immunization with mo No. methoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with mono methoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., 2015, 589, 2477-2486.
Robinet et al. "Elastin-derived peptides enhance angiogenesis by promoting endothelial cell migration and tubulogenesis through upregulation of MT1-MMP," J. Cell Science, 2005, 118:343-356.
Römer et al., "The elaborate structure of spider silk: structure and function of a natural high performance fiber," Prion 2, 2008, 154-161.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem Pharmacol. 1996, 51(7):911-908.
Saifer et al., "Selectivity of binding of PEGs and PEG-like oligomers to anti-PEG antibodies induced by methoxyPEG-proteins," Molecular Immunology 57, 2014, 236-246.
Sandler et al., "Gemcitabine: Single-Agent and Combination Therapy in Non-Small Cell Lung Cancer," Oncologist 1999, 4(3)241-251.
Schellenberger et al., "A recombinant polypeptide extends the in vivo half-life of peptides and proteins in a tunable manner," Nat. Biotechnol. 27, 2009, 1186-1188.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., 2007, 93, 2429-2435.
Shen et al., "Conjugation site modulates the in vivo stability and thearpeutic activity of antibody-drug conjugates," Nat Biotechnol, 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, 2009, 10:1955-1961.
Sherman et al., "Next-Generation PEGylation Enables Reduced Immunoreactivity of PEG-Protein Conjugates," Drug and Development & Delivery, 2012, vol. 12, No. 5, 36-42.
Sherman et al., "Role of the Methoxy Group in Immune Responses to mPEG-Protein Conjugates," Bioconjugate Chemistry, 2012, 23, 485-499.
Shi et al., "Cell adhesion on a POEGMA-modified topographical surface," Langmuir: the ACS journal of surfaces and colloids, 2012, 28 (49), 17011-8.
Shimoboji et al., "Temperature-Induced Switching of Enzyme Activity with Smart Polymer-Enzyme Conjugates," Bioconjugate Chem. 2003, 14, 517-525.
Siegwart et al., "ATRP In The Design Of Functional Materials For Biomedical Applications," Prog Polymer Science, 2012, vol. 37, No. 1, pp. 18-37.
Silva et al., "Selective differentiation of neural progenitor cells by high-epitope density nanofibers," Science, 2004, 303, 1352-5.
Simakova et al., "Aqueous ARGET ATRP," Macromolecules 45, 2012, 6371-6379.
Sorkin et al., "Signal transduction and endocytosis: close encounters of many kinds," Nat Rev Mol Cell Biol, 2002, 3(8):600-614.

(56) References Cited

OTHER PUBLICATIONS

Stefl et al., "RNA sequence-and shape-dependent recognition by proteins in the ribonucleoprotein particle" EMBO reports (2005) 6(1):33-38.
Sumerlin, "Proteins as Initiators of Controlled Radical Polymerization: Grafting-fromvia ATRP and RAFT," ACS Macro Lett. 2012, 1, 141-145.
Surwit et al., Diet-induced type II diabetes inC57BL/6J mice, Diabetes 37, 1988, 1163-1167.
Swee et al., "Sortase-mediated modification of αDEC205 affords optimization of antigen presentation and immunization against a set of viral epitopes," Proc Natl Acad Sci USA, 2013, 110(4):1428-1433.
Swers et al., Multivalent Scaffold Proteins as Superagonists of TRAIL Receptor 2-Induced Apoptosis, Mol Cancer Ther, 2013, 12, 1235-1244.
Tang et al., "Combinatorial codon scrambling enables scalable gene synthesis and amplification of repetitive proteins," Nature Mater., 2016, 15, 419-424.
Tantakitti et al., "Energy landscapes and functions of supramolecular systems," Nat. Mater., 2016, 15, 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, 2012, 3 (10), 2743-2751.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tong et al., "Protein Modification with Amphiphilic Block Copoly(2-oxazoline)s as a New Plataform for Enhanced Cellular Delivery," Mol. Pharm., 2010, vol. 7, No. 4, pp. 984-992.
Ton-That et al., "Assembly of pili on the surface of Corynebacterium diptheriae," 2003, 50(4):1429-1438.
Ton-That et al., "Purification and characterization of sortase, the transpeptide that cleaves surface proteins of Staphylococcus aureus and the LPXTG motif," Proc Natl Acad Sci USA, 1999, 96(22):12424-12429.
Torchilin, "Recent advances with liposomes as pharmaceutical carriers," Nature Rev. DrugDiscov. 2005, 4(2):145-160.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Expression and purification of recombinant proteins from Escherichia coli: Comparison of an elastin-like polypeptide fusion with an oligo histidine fusion" Protein Science, 2004, 13: 3274-3284.
Triola et al., "Chemical biology of lipidated proteins," ACS Chemical Biology, 2012, 7, 87-99.
Troyanskaya et al., "Nonparametric methods for identifying differentially expressed genes in microarray data," Bioinformatics, 2002, 18(11):1454-61.
Tsarevsky et al., "Deactivation efficiency and degree of control over polymerization in ATRP in protic solvents," Macromolecules 37, 2004, 9768-9778.
Tsume et al., "The development of orally administrable gemcitabine prodrugs with D-enantiomer amino acids: Enhanced membrane permeability and enzymatic stability," Eur. J. Pharm Biopharm 2014, 86(3):514-523.
Turunen et al., "Paclitaxel Succinate Analogs: Anionic Introduction as a Strategy to Impart Blood Brain Barrier Permeability," Bioorg Med Chem Lett, 2008, 18(22):5971-5974.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based onlnverseTemperature Transitions," Biopolymers, 1992, 32:1243-1250.

Urry et al., "Physical chemistry of biological free energy transduction as demonstrated by elastic protein-based polymers," J. of Phys. Chem. B.,1997, 101, 11007-11028.
Urry et al., "Temperature of polypeptide inverse temperature transition depends on mean residue hydrophobicity," J. Am. Chem. Soc., 1991, 113(11):4346-4348.
Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Veronese et al., "PEGylation successful approach to drug delivery," Drug Discovery Today, 2005, 10(21):1451-1458.
Veronese, "Peptide and protein PEGylation: a review of problems and solutions," Biomaterials 22, 2001, 405-417.
Viegas et al.,"Polyoxazoline: Chemistry, properties and applications," Bioconjugate Chem., 2011, vol. 22, pp. 976-986.
Voelker et al.,"Alteration of the specificity and regulation of fatty acid synthesis of Escherichia coli by expression of a plant medium-chain acyl-acyl carrier protein thioesterase," J Bacteriol., 1994, 176(23):7320-7.
Vrignaud et al., "Strategies for the nanoencapsulation of hydrophilic molecules in polymer-based nanoparticles," Biomaterials 2011, 32(33):8593-8604.
Walczak, "DeathReceptor-Ligand Systems in Cancer, Cell Death, and Inflammation," Cold Spring Harb. Perspect. Biol., 2013, 5, a008698.
Walsh et al., "Post-translational modifications in the context of therapeutic proteins," Nat. Biotechnol., 2006, 24, 1241-1252.
Walsh et al., "Posttranslationale Proteinmodifikation die Chemie der Proteomdiversifizierung," Angew Chem, 2005, 117, 7508-7539.
Walsh et al., "Protein posttranslational modifications: The chemistry of proteome diversifications," Angew. Chem. Int Ed., 2005, 44, 7342-7372.
Wang et al., "Enhanced Tumor Delivery of Gemcitabine via PEG-DSPE/TPGS Mixed Micelles," Mol. Pharm. 2014, 11, 1140-1150.
Wendt et al., "DNA-mediated Folding and Assembly of MyoD-E47 Heterodimers," Journal of Biol. Chem., 1998, 273(10):5735-5743.
Werle et al., "Strategies to improve plasma half life time ofpeptide and protein drugs," Amino Acids 30, 2006, 351-367.
Wienkers et al., "Predicting in vivo drug interactions fromin vitro drug discovery data," Nat. Rev. Drug. Discov. 2005, 4(10):825-833.
Williamson et al., "Efficient N-terminal labeling of proteins by use of sortase," Angew Chem Int ed Engl, 2012, 51(37):9377-9380.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wu et al., "Site-specific chemical modification of recombinant proteins produced in mammalian cells by using the genetically encoded aldehyde tag," Proc Natl Acad Sci USA, 2009, 106(9):3000-3005.
Wu et al., "Sortase A—Catalyzed Transpeptidation of Glycosylphosphatidylinositol Derivatives for Chemoenzymatic Synthesis of GPI-Anchored Proteins," J. Am. Chem. Soc. 2010, 132, 1567-1571.
Xavier et al., "HPLC Method for the Dosage of Paclitaxel in Copaiba Oil: Development, Validation. Application to the Determination of the Solubility and Partition Coefficients," Chromatographia, 2016, 79, 405-412.
Xu et al., "A quality by design (QbD) case study on liposomes containing hydrophilic API: II. Screening of critical variables, and establishment of design space at laboratory scale," Int. J. Pharm. 2012, 423(2):543-553.
Xu et al., "Exendin-4 stimulates both beta-cell replication and neogenesis, resulting in increased beta-cell mass and improved glucose tolerance in diabetic rats," Diabetes 48, 1999, 2270-2276.

(56) References Cited

OTHER PUBLICATIONS

Xu et al., "Self-assembly behavior of peptide amphiphiles (PAs) with different length of hydrophobic alkyl tails," Colloids Surfaces B Biointerfaces, 2010, 81, 329-335.
Yang et al., "Poly(carboxybetaine) nanomaterials enable long circulation and prevent polymer-specific antibody production," Nano Today, 2014, 9(1):10-16.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm Res., 1999, 16(7): 1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem Pharmacol, 2007, 73: 84-93.
Youn et al., "High-yield production of biologically active mono-PEGylated salmon calcitonin by site-specific PEGylation," J. Control. Release 117, 2007, 371-379.
Zhang et al., "A self-assembly pathway to aligned monodomain gels," Nat. Mater., 2010, 9, 594-601.
Zhang et al., "Nanoparticles in medicine: therapeutic applications and developments," Clin. Pharmacol. Ther. 2008, 83(5):761-769.
Zhang et al., "Shape Effects of Nanoparticles Conjugated with Cell-Penetrating Peptides (HIV Tat PTD) on CHO Cell Uptake," Bioconjugate Chem, 2008, 19(9):1880-1887.
Zhao et al., "Fluorescence probe techniques used to study micelle formation in water-soluble block copolymers," Langmuir 1990, 6(2):514-516.
Zimm, "Apparatus and Methods for Measurement and Interpretation of the Angular Variation of Light Scattering; Preliminary Results onPolystyrene Solutions," J. Chem. Phys. 1948, 16, 1099-1116.
Zong et al., "Crystal structures of Staphylococcus aureus sortase A and its substrate complex," J. Biol. Chem. 279, 2004,31383-31389.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2015 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
Chockalingam et al., "Design and application of stimulus-responsive peptide systems," Protein Engineering, Design & Selection, 2007, 20(4):155-161.
Eurasian Patent Office Action for Application No. 201890417 dated Oct. 11, 2019 (4 pages).
Park et al., "Protein stitchery: Design of a protein for selective binding to a specific DNA sequence," PNAS, 1992, vol. 39:9094-9096.
Olafsen et al., "Covalent disulfide-linked anti-CEA diabody allows site-specific conjugation and radiolabeling for tumor targeting applications," Protein Engineering, Design & Selection, 2004, 17(1):21-27.
Hu et al., "Nanografting De Novo Proteins onto Gold Surfaces," Langmuir, 2005, vol. 21:9103-9109.
McDaniel, "Assembly of Highly Asymmetric Genetically-Encoded Amphiphiles for Thermally Targeted Delivery of Therapeutics," Dissertation, 2013, 295 pages.
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
United States Patent Office Action for U.S. Appl. No. 16/058,924 dated Nov. 26, 2019 (23 pages).
AACR, "AACR Cancer Progress Report 2016," Clin Cancer Res, 2016, 22, 143 pages.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, 2009, 90, 67-74.
Adamska et al., "Pancreatic ductal adenocarcinoma: Current and evolving therapies," J Mol Sci, 2017, 18, 1338-1380.
Adiseshaiah et al., "Nanomedicine strategies to overcome the pathophysiological barriers of pancreatic cancer," Nat Rev Clin Oncol, 2016, 13, 750-765.
Albanese et al., "The effect of nanoparticle size, shape, and surface chemistry on biological systems," Annu. Rev. Biomed. Eng., 2012, 14, 1-16.
Andersen et al., "Extending Half-life by Indirect Targeting of the Neonatal Fc Receptor (FcRn) Using a Minimal Albumin Binding Domain," Journal of Biological Chemistry, 2011, 286(7): p. 5234-5241.
Asai et al., "Protein polymer hydrogels by in situ, rapid and reversible self-gelation," Biomaterials, 2012, 33, 5451-5458.
Atun et al., "Expanding global access to radiotherapy," Lancet Oncol, 2015, 16, 1153-1186.
Awasthi et al., "Comparative benefits of Nab-paclitaxel over gemcitabine or polysorbate-based docetaxel in experimental pancreatic cancer," Carcinogenesis, 2013, 34, 2361-2369.
Awasthi et al., "Evaluation of combination treatment benefits of nab-paclitaxel in experimental pancreatic cancer," Journal of Clinical Oncology, 2012, 30, 170.
Azhdarinia et al., "Regional radiochemotherapy using in situ hydrogel," Pharm Res., 2005, 22, 776-783.
Bache et al., "Investigating the accuracy of microstereotactic-body-radiotherapy utilizing anatomically accurate 3D printed rodent-morphic dosimeters," Medical Physics, 2015, 42, 846-855.
Bailey et al., "Genomic analyses identify molecular subtypes of pancreatic cancer," Nature, 2016, 531, 47-52.
Bamford et al., "The COSMIC (Catalogue of Somatic Mutations in Cancer) database and website," British Journal of Cancer, 2004, 91, 355-358.

(56) References Cited

OTHER PUBLICATIONS

Barbuti et al., "Paclitaxel through the ages of anticancer therapy: Exploring its role in che mo resista nee and radiation therapy," Cancers, 2015, 7, 2360-2371.

Barnett et al., "Normal tissue reactions to radiotherapy: towards tailoring treatment dose by genotype," Nat Rev Cancer, 2009, 9, 134-142.

Barton et al., "Estimating the demand for radiotherapy form the evidence: A review of changes from 2003 to 2012," Radiother Oncol, 2014, 112, 140-144.

Baskar et al., "Cancer and Radiation Therapy: Current Advances and Future Directions," Int. J. Med. Sci., 2012, 9, 193-199.

Begg et al., "Strategies to improve radiotherapy with targeted drugs," Nat Rev Cancer, 2011, 11, 239-253.

Bernacki et al., "Length-dependent aggregation of uninterrupted polyalanine peptides," Biochemistry, 2011, 50, 9200-9211.

Blasko et al., "Brachytherapy for carcinoma of the prostate: Techniques, patient selection, and clinical outcomes," Seminars in Radiation Oncology, 2002, 12, 81-94.

Blasko et al., "The role of external beam radiotherapy with i-125/Pd-103 brachytherapy for prostate carcinoma," Radiother Oncol, 2000, 57, 273-278.

Blasko et al., "Transperineal percutaneous iodine-125 implantation for prostatic carcinoma using transrectal ultrasound and template guidance," Endocurietherapy/Hyperthermia Oncology, 1987, 3, 131-139.

Bley et al., "Microtubule stabilising agents and ionising radiation: Multiple exploitable mechanisms for combined treatment," Eur J Cancer, 2013, 49, 245-253.

Bocci et al., "The pharmacological bases of the antiangiogenic activity of paclitaxel," Angiogenesis, 2013, 16, 481-492.

Bochicchio et al., "Investigating by CD the molecular mechanism of elasticity of elastomeric proteins," Chirality, 2008, 20, 985-994.

Boldt, "Use of albumin: an update," Br J. Anaesth., 2010, 104 (3), 276-284.

Branco et al., "Self-assembling materials for therapeutic delivery," Acta Biomaterialia, 2009, 5(3): p. 817-831.

Burchard, "Light Scattering Techniques," Physical techniques for the study of food biopolymers, 1994, 151-213.

Burnouf, "Modern plasma fractionation," Transfus. Med. Rev., 2007, 21 (2), 101-117.

Cabral et al., "Accumulation of sub-100 nm polymeric micelles in poorly permeable tumours depends on size," Nature Nanotechnology, 2011, 6, 815-823.

Callahan et al., "Triple stimulus-responsive polypeptide nanoparticles that enhance intratumoral spatial distribution," Nano Letters, 2012, 12, 2165-2170.

Camilloni et al., "Determination of secondary structure populations in disordered states of proteins using nuclear magnetic resonance chemical shifts," Biochemistry, 2012, 51, 2224-2231.

Cao et al., "Monitoring the effects of anti-angiogenesis on the radiation sensitivity of pancreatic cancer xenografts using dynamic contrast-enhanced computed tomography," Int J Radiation Oncol Biol Phys, 2014, 88, 412-418.

Cardenes et al., "Locally advanced pancreatic cancer: Current therapeutic approach," The Oncologist, 2006, 11, 612-623.

Cataldo et al., "Radiation-induced crosslinking of collagen gelatin into a stable hydrogel," Journal of Radioanalytical and Nuclear Chemistry, 2008, 275, 125-131.

Ceska et al., "A new and rapid method for the clinical determination of a-amylase activities in human serum and urine. Optimal conditions," Clinica Chimica Acta, 1969, 26, 437-444.

Chakrabartty et al., "Stability of a-Helices," Adv Protein Chem, 1995, 46, 141-176.

Chang et al., "Tumor-stroma interaction in orthotopic primary pancreatic cancer xenografts during hedgehog pathway inhibition," Int. J. Cancer, 2013, 133, 225-235.

Chaudhury et al., "The major histocompatibility complex-related Fc receptor for IgG (FcRn) binds albumin and prolongs its lifespan," J Exp Med, 2003, 197(3): p. 315-22.

Chen et al., "Anisotropic hydrogels fabricated with directional freezing and radiation-induced polymerization and crosslinking method," Materials Letters, 2012, 89, 104-107.

Chen et al., "Rheology of Soft Materials," Annual Review of Condensed Matter Physics, 2010, 1, 301-322.

Chen et al., "The use of self-adjuvanting nanofiber vaccines to elicit high-affinity B cell responses to peptide antigens without inflammation," Biomaterials 34, 2013, 8776-8785.

Cho et al., "Hydrogen bonding of β-turn structure is stabilized in D(2)O," J Am Chern Soc, 2009, 131, 15188-15193.

Choi et al., "Renal Clearance of Nanoparticles," Nature biotechnology, 2007, 25(10): p. 1165-1170.

Choy et al., "Investigation of taxol as a potential radiation sensitizer," Cancer, 1993, 71, 3774-3778.

Christensen et al., "Predicting Transition Temperatures of Elastin-Like Polypeptide Fusion Proteins," Biomacromolecules, 2013, 14(5): p. 1514-1519.

Cid-Arregui et al., "Perspectives in the treatment of pancreatic adenocarcinoma," World Journal of Gastroenterology, 2015, 21, 9297-9316.

Ciezki et al., "Brachytherapy or surgery? A composite view," Oncology, 2009, 23, 960-964.

Cima, "AVMA Guidelines for the Euthanasia of Animal: 2013 Edition," Journal of the American Veterinary Medical Association, 2013, 242, 102 pages.

Cirulis et al., "Viscoelastic properties and gelation of an elastin-like polypeptide," Journal of Rheology, 2009, 53, 1215-1228.

Clarke et al., "Tropoelastin massively associates during coacervation to form quantized protein spheres," Biochemistry, 2006, 45, 9989-9996.

Clave et al., "Amylase, lipase, pancreatic isoamylase, and phospholipase A in diagnosis of acute pancreatitis," Clinical Chemistry, 1995, 41, 1129-1134.

Colomb et al., "Radiation-Convertible Polymers from Norbornenyl Derivatives. Crosslinking with Ionizing Radiation," Journal of Applied Polymer Science, 1970, 14, 1659-1670.

Conrad et al., "ELPylated anti-human TNF therapeutic single-domain antibodies for prevention of lethal septic shock," Plant Biotechnology Journal, 2011, 9, 22-31.

Darzynkiewicz et al., "DNA content measurement for DNA ploidy and cell cycle analysis," Current Protocols in Cytometry, 2001, 7.5.1-7.5.24.

De Simone et al., "Accurate random coil chemical shifts from an analysis of loop regions in native states of proteins," J Am Chern Soc, 2009, 131, 16332-16333.

Deer et al., "Phenotype and genotype of pancreatic cancer cell lines," Pancreas, 2010, 39, 425-435.

Dejana et al., "The role of adherens junctions and VE-cadherin in the control of vascular permeability," J Cell Sci, 2008, 121, 2115-2122.

Delaglio et al., "NMRPipe: A multidimensional spectral processing system based on UNIX pipes," Journal of Biomolecular NMR 6, 1995, 277-293.

Delisser et al., "Vascular endothelial platelet endothelial cell adhesion molecule 1(PECAM-1) regulates advanced metastatic progression," PNAS, 2010, 107, 18616-18621.

Dennis et al., "Albumin binding as a general strategy for improving the pharmacokinetics of proteins," J Biol Chem, 2002, 277(38): p. 35035-43.

Deshayes et al., "Radium 223 dichloride for prostate cancer treatment," Drug Des Devel Ther, 2017, 11, 2643-2651.

Diana et al., "Prognostic role and correlation of CA9, CD31, CD68 and CD20 with the desmoplastic stroma in pancreatic ductal adenocarcinoma," Oncotarget, 2016, 7, 72819-72832.

Ding et al., "Mechanism for the alpha-helixto beta-hairpin transition," Proteins, 2003, 53, 220-228.

Dreher et al., "Thermal cycling enhances the accumulation of a temperature-sensitive biopolymer in solid tumors," Cancer Res, 2007, 67, 4418-4424.

Du et al., "Endoscope-assisted brachytherapy for pancreatic cancer: From tumor killing to pain relief and drainage," Journal of interventional gastroenterology, 2011, 1, 23-27.

(56) References Cited

OTHER PUBLICATIONS

Ducreux et al., "Radiation plus docetaxel and cisplatin in locally advanced pancreatic carcinoma: A non-comparative randomized phase II trial," Digestive and Liver Disease, 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Accessed Jan. 11, 2017.
Duncan, "The dawning era of polymer therapeutics," Nature Reviews Drug Discovery, 2003, 2, 347-360.
Eisenhauer et al., "New response evaluation criteria in solid tumours: Revised RECIST guideline (version 1.1)," Eur J Cancer, 2017, 45, 228-247.
Ellis, "Macromolecular crowding: obvious but underappreciated," Trends Biochem. Sci., 2001, 26 (10), 597-604.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Falk et al., "Hyperthermia in oncology," Int J Hyperthermia, 2001, 17, 1-18.
Farmer et al., "Conformational behavior of chemically reactive alanine-rich repetitive protein polymers," Biomacromolecules, 2005, 6, 1531-1539.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, 2015, 16, 3389-3398.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, 2018, 130:A19112.
Frilling et al., "Recommendations for management of patients with neuroendocrine liver metastases," The lancet oncology, 2014, 15, e8-21.
Fu et al., Recent Patents on Anti-Cancer Drug Discovery, 2009. 4(3): p. 262-272.
Fujiwara et al., "Modulating effect of the PI3-kinase inhibitor LY294002 on cisplatin in human pancreatic cancer cells," Journal of Experimental & Clinical Cancer Research, 2008, 27, 76.
Furumoto et al., "Effect of coupling of albumin onto surface of PEG liposome on its In vivo disposition," International Journal of Pharmaceutics, 2007, 329(1-2): p. 110-116.
Ghoorchian et al., "Molecular architecture influences the thermally induced aggregation behavior of elastin-like polypeptides," Biomacromolecules, 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, 2009, 27, 607-612.
Glassman et al., "Toughening of Thermoresponsive Arrested Networks of Elastin-Like Polypeptides To Engineer Cytocompatible Tissue Scaffolds," Biomacromolecules, 2016, 17, 415-426.
Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Greco et al., "The search for synergy: a critical review from a response surface perspective," Pharmacological Reviews, 1995, 24, 331-385.
Green et al., "Abraxane@, a novel Cremophor®-free, albumin-bound particle form of paclitaxel for the treatment of advanced non-small-cell lung cancer," Annals of Oncology, 2006, 17, 1263-1268.

Grimm et al., "Advances in Brachytherapy," Reviews in Urology, 2004, 6, S37-S48.
Güngör et al., "Pancreatic cancer," British Journal of Pharmacology, 2014, 171, 849-858.
Guo et al., "Nanoparticles escaping RES and endosome: challenges for siRNA delivery for cancer therapy," J. Nano.materials, 2011, 2011: 1-12.
Gustafsson, "Nonlinear structured-illumination microscopy: widefield fluorescence imaging with theoretically unlimited resolution," Proc Natl Acad Sci USA, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, 2016, 139, 2116-2126.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, 2013, vol. 4, Article 331, 7 pages.
Han et al., "Survival of patients with advanced pancreatic cancer after iodine$^{125}$ seeds implantation brachytherapy: A meta-analysis," Medicine, 2017, 96, e5719.
Harmon et al., "A Model for Hysteresis Observed in Phase Transitions of Thermally Responsive Instrinsically Disordered Protein Polymers," Biophysical Journal, 2017, 112(3):207a.
Hathout et al., "Analysis of seed loss and pulmonary seed migration in patients treated with virtual needle guidance and robotic seed delivery," American journal of clinical oncology, 2011, 34, 449-453.
Herrero-Vanrell et al., "Self-assembled particles of an elastin-like polymer as vehicles for controlled drug release," J Control Release, 2005, 102, 113-122.
Hidalgo, "Pancreatic Cancer," N Engl J Med, 2010, 362, 1605-1617.
Hingorani et al., "Phase 1b Study of PEGylated Recombinant Human Hyaluronidase and Gemcitabine in Patients with Advanced Pancreatic Cancer," Clinical Cancer Research, 2016, 22, 2848-2854.
Ho et al., "Internal radiation therapy for patients with primary or metastatic hepatic cancer: a review," Cancer, 1998, 83, 1894-1907.
Holm et al., "Transperineal $^{125}$iodine seed implantation in prostatic cancer guided by transrectal ultrasonography," The Journal of urology, 2002, 167, 985-988.
Hopp et al., "The effects of affinity and valency of an albumin-binding domain (ABD) on the halflife of a single-chain diabody-ABD fusion protein," Protein Engineering Design and Selection, 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, 2007, 119, 25-33.
Hruby et al., "Thermoresponsive polymeric radionuclide delivery system—an injectable brachytherapy," Eur J Pharm Sci., 2011,42, 484-488.
Hrycushko et al., "Direct intratumoral infusion of liposome encapsulated rhenium radionuclides for cancer therapy: effects of non-uniform intratumoral dose distribution," Med Phys, 2011, 38, 1339-1347.
Hu et al., "Design of tumor-homing and pH-responsive polypeptide-doxorubicin nanoparticles with enhanced anticancer efficacy and reduced side effects," Chemical Communications, 2015, 51, 11405-11408.

(56) References Cited

OTHER PUBLICATIONS

Huang et al., "Photodynamic Therapy Synergizes with Irinotecan to Overcome Compensatory Mechanisms and Improve Treatment Outcomes in Pancreatic Cancer," Cancer Research, 2016, 76, 1066-1077.
Huotari et al., "Endosome maturation," EMBO J, 2011, 30 (17), 3481-3500.
Hwang et al., "Caprolactonic poloxamer analog: PEG-PCL-PEG," Biomacromolecules, 2005, 6, 885-890.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase 1 and pharmacokinetic study of ABI-007, a Cremophor-free, protein-stabilized, nanoparticle formulation of paclitaxel," Clin. Cancer Res., 2002, 8 (5), 1038-1044.
Ito et al., "In vivo antitumor effect of the mTOR inhibitor CCI-779 and gemcitabine in xenograft models of human pancreatic cancer," International Journal of Cancer, 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jenkins et al., In vivo monitoring of tumor relapse and metastasis using bio luminesce nt PC-3M-Iuc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, 2012, 13, 206-215.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Jonsson et al., "Engineering of a femtomolar affinity binding protein to human serum albumin," Protein Engineering Design and Selection, 2008, 21(8): 515-527.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, 2011, 89, 183-188.
Kamisawa et al., "Pancreatic cancer," Lancet, 2016, 388, 73-85.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001,61, 14-18.
Karamanolis et al., "Increased expression of VEGF and CD31 in postradiation rectal tissue: implications for radiation proctitis," Mediators Inflamm, 2013, 515048.
Karperien, A. FracLac for Image J, version 2.5 <http://rsb.info.nih.gov/ij/plugins/fraclac/FLHelp/Introduction.htm> 1999-2012.
Katakura, "Nuclear Data Sheets for A 32 125," Nuclear Data Sheets, 2011, 112, 495-705.
Kato et al., "Acidic extracellular microenvironment and cancer," Cancer Cell Int, 2013, 13, 89, 8 pages.
Keten et al., "Nanoconfinement controls stiffness, strength and mechanical toughness of β-sheet crystals in silk," Nat Mater, 2010, 9, 359-367.
Khanna et al., "The dog as a cancer model," Nat. Biotechnol., 2006, 24, 1065-1066.
Khazov et al., "Nuclear Data Sheets for A=131," Nuclear Data Sheets, 2006, 107, 2715-2930.
Kim et al., "Recombinant elastin-mimetic biomaterials: Emerging applications in medicine," Adv Drug DelivRev, 2010, 62, 1468-1478.

Kobayashi et al., "Summary of recombinant human serum albumin development," Biologicals, 2006, 34(1): 55-59.
Koehler et al., "Albumin affinity tags increase peptide half-life In vivo," Bioorganic & Medicinal Chemistry Letters, 2002, 12(20): 2883-2886.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, 2008, 1778, 631-645.
Krempien et al., "Neoadjuvant chemoradiation in patients with pancreatic adenocarcinoma," HPB (Oxford), 2006, 8, 22-28.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Labelle et al., "Vascular endothelial cadherin promotes breast cancer progression via transforming growth factor β signaling," Cancer Res, 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Lee et al., "Immunohistochemical analysis of claudin expression in pancreatic cystic tumors," Oncology Reports, 2011, 25(4): 971-978.
Lee et al., "In vivo bioluminescent imaging of irradiated orthotopic pancreatic cancer xenografts in nonobese diabeti-sever combined immunodeficient mice: a novel method for targeting and assaying efficacy of ionizing radiation," Transl. Oncol., 2010, 3, 153-159.
Lee et al., "Mechanical properties of cross-linked syntheti elastomeric polypentapeptides," Macromolecules, 2001, 34, 5968-5974.
Lee et al., "Phase transition and elasticity of protein-based hydrogels," J. Biomater. Sci. Polymer Edn, 2001, 12, 229-242.
Levy et al., "Novel Exenatide Analogs with Peptidic Albumin Binding Domains: Potent Anti-Diabetic Agents with Extended Duration of Action," PLoS ONE, 2014, 9(2): e87704, 9 pages.
Li et al., "Elastin is an essential determinant of arterial morphogenesis," Nature, 1998, 393, 276-280.
Li et al., "Nanoparticles Evading The Reticuloendothelial System: Role of The Supported Bilayer," Biochim. Biophys. Acta, 2009, 1788 (10), 2259-2266.
Li et al., "Pancreatic cancer," Lancet, 2004, 363, 1049-1057.
Lillie et al., "The viscoelastic basis for the tensile strength of elastin," Int J Biol Macromol, 2002, 30, 119-127.
Lin et al., "Utility of immunohistochemistry in the pancreatobiliary tract," Arch Pathol Lab Med, 2015, 139, 24-38.
Litiere et al., "RECIST—learning from the past to build the future," Nat Rev Clin Oncol, 2017, 14, 187-192.
Liu et al., "Brachytherapy using injectable seeds that are self-assembled from genetically encoded polypeptides in situ," Cancer Res, 2012, 72, 5956-5965.
Liu et al., "Tracking the in vivo fate of recombinant polypeptides by isotopic labeling," Journal of Controlled Release, 2006, 114, 184-192.
Liu et al., "Tumor accumulation, degradation and pharmacokinetics of elastin-like polypeptides in nude mice," Journal of Controlled Release, 2006, 116, 170-178.
Ludden, "Nonlinear pharmacokinetics: clinical Implications," Clin. Pharmacokinet., 1991,20 (6), 429-446.
Luo et al., "Noncovalent Modulation of the Inverse Temperature Transition and Self-Assembly of Elastin-b-Collagen-like Peptide Bioconjugates," J Am Chem Soc, 2015, 137, 15362-15365.
MacEwan et al., "Applications of elastin-like polypeptides in drug delivery," Journal of Controlled Release, 2014, 190: p. 314-330.
MacEwan et al., "Controlled apoptosis by a thermally toggled nanoscale amplifier of cellular uptake," Nano Letters, 2014, 14, 2058-2064.

(56) References Cited

OTHER PUBLICATIONS

Maitra et al., "Pancreatic Cancer," Annu Rev Pathol Meeh Dis, 2008, 3, 157-188.
Manzoor et al., "Overcoming limitations in nanoparticle drug delivery: triggered, intravascular release to improve drug penetration into tumors," Cancer Res, 2012, 72, 5566-5575.
Mao et al., "DNA repair by nonhomologous end joining and homologous recombination during cell cycle in human cells," Cell cycle, 2008, 7, 2902-2906.
Mariam et al., "Albumin corona on nanoparticles—a strategic approach in drug delivery," Drug Deliv., 2016, 23 (8), 2668-2676.
Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival - CapRI-2," BMC Cancer, 2009, 9, 1-8.
Matsumura, "Cancer stromal targeting (CAST) therapy," Advanced Drug Delivery Reviews, 2012, 64, 710-719.
McConkey et al., "Molecular Characterization of Pancreatic Cancer Cell Lines," Pancreatic Cancer, 2010, 457-469.
McDaniel et al., "Actively targeting solid tumours with thermoresponsive drug delivery systems that respond to mild hyperthermia," Int J Hyperthermia, 2013, 29, 501-510.
McDaniel et al., "Doxorubicin-conjugated chimeric polypeptide nanoparticles that respond to mild hyperthermia," Control. Release, 2012, 159 (3), 362-367.
McDaniel et al., "Rational design of "heat seeking" drug loaded polypeptide nanoparticles that thermally target solid tumors," Nano Letters, 2014, 14, 2890-2895.
Merrick et al., "Seed fixity in the prostate/periprostatic region following brachytherapy," International journal of radiation oncology, biology, physics, 2000, 46, 215-220.
Methods and Welfare Considerations in Behavioral Research with Animal. (2002).
Meyer et al., "Drug targeting using thermally responsive polymers and local hyperthermia," Journal of Controlled Release, 2001, 74, 213-224.
Miao et al., "Sequence and domain arrangements influence mechanical properties of elastin-like polymeric elastomers," Biopolymers, 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, 2013, 62, 317-326.
Micsonai et al. "Accurate secondary structure prediction and fold recognition for circular dichroism spectroscopy," Proc Natl Acad Sci USA, 2015, 112, E3095-3103.
Milenic et al., "Antibody-targeted radiation cancer therapy," Nature Reviews Drug Discovery, 2004, 3, 488-498.
Miller et al., "Solubilized, Spaced Polyalanines: A Context-Free System for Determining Amino Acid a-Helix Propensities," Journal of the American Chemical Society, 2002, 124, 945-962.
Miyata et al., "Polymeric micelles for nano-scale drug delivery," Reaction & Functional Polymers, 2011, 71, 227-234.
Mjelle et al., "Cell cycle regulation of human DNA repair and chromatin remodeling genes," DNA Repair, 2015, 30, 53-67.
Morgan et al., "The combination of epidermal growth factor receptor inhibitors with gemcitabine and radiation in pancreatic cancer," Clin Cancer Res, 2008, 14, 5142-5149.
Muiznieks et al., "Structural changes and facilitated association of tropoelastin," Archives of Biochemistry and Biophysics, 2003, 410, 317-323.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Murphy et al., "A dosimetric model of duodenal toxicity after stereotactic body radiotherapy for pancreatic cancer," Int J Radiation Oncology Biol Phys, 2010, 78, 1420-1426.
Na et al., "Thermoresponsive pore structure of biopolymer microspheres for a smart drug carrier," Langmuir, 2010, 26, 11165-11169.
Nettles et al., "Applications of elastin-like polypeptides in tissue engineering," Adv Drug Deliv Rev, 2010, 62, 1479-1485.
Nettles et al., "In situ crosslinking elastin-like polypeptide gels for application to articular cartilage repair in a goat osteochondral defect model," Tissue Eng Part A, 2008, 14, 1133-1140.
Newton et al., "Commissioning a small-field biological irradiator using point, 2D, and 3D dosimetry techniques," Medical Physics, 2011, 38, 6754-6762.
Nichols et al., "Claudin 4 protein expression in primary and metastatic pancreatic cancer," Am J Clin Pathol, 2004, 121, 226-230.
Nie, "Understanding and overcoming major barriers in cancer nanomedicine," Nanomedicine (Lond) 2010, 5 (4), 523-528.
Nilvebrant et al., "The albumin-binding domain as a scaffold for protein engineering," Computational and Structural Biotechnology Journal, 2013, 6: e201303009, 8 pages.
Ogawara et al., "Pre-coating with serum albumin reduces receptor-mediated hepatic disposition of polystyrene nanosphere: implications for rational design of nano particles," Journal of Controlled Release, 2004, 100(3): 451-455.
Pagani et al., "International guidelines for management of metastatic breast cancer: can metastatic breast cancer be cured?," Journal of the National Cancer Institute, 2010, 102, 456-463.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, 2016, 96, S204-S205.
Paoloni et al., "Translation of new cancer treatments from pet dogs to humans," Nat. Rev. Cancer 2008, 8 (2), 147-156.
Patil et al., "Cellular delivery of doxorubicin via pH-controlled hydrazone linkage using multifunctional nano vehicle based on poly(beta-l-malic acid)," Int J Mol Sci, 2012, 13, 11681-11693.
Phan et al., "Temperature-responsive self-assembly of charged and uncharged hydro>Q(ethylcellulose-graft-poly(N-isopropylacrylamide) copolymer in aqueous solution," Colloid Polym. Sci., 2011, 289 (9), 993-1003.
Pliarchopoulou et al., "Pancreatic cancer: Current and future treatment strategies," Cancer Treatment Reviews, 2009, 35, 431-436.
Pometun et al., "Quantitative observation of backbone disorder in native elastin," J Biol Chem, 2004, 279, 7982-7987.
Potters et al., "12-year outcomes following permanent prostate brachytherapy in patients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, 2012, 21,418-429.
Provenzano et al., "Hyaluronan, fluid pressure, and stromal resistance in pancreas cancer," Br J Cancer, 2013, 108, 1-8.

(56) References Cited

OTHER PUBLICATIONS

Qiu et al., "Development of Orthotopic Pancreatic Tumor Mouse Models," Methods Mol Biol, 2013, 980: 215-223.
Quarmby et al., "Irradiation induces upregulation of CD31 in human endothelial cells," Arterioscler Thromb Vase Biol, 1999, 19, 588-597.
Quarmby et al., "Radiation-induced normal tissue injury: role of adhesion molecules in leukocyte-endothelial cell interactions," Int J Cancer, 1999, 82, 385-395.
Rabotyagova et al., "Protein-based block copolymers," Biomacromolecules, 2011, 12, 269-289.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, 2016, 76.
Rankine et al., "Investigating end-to-end accuracy of image guided radiation treatment delivery using a micro-irradiator," Physics in Medicine and Biology, 2013, 58, 7791-7801.
Rao et al., "Synthetic nanoparticles camouflaged with biometric erythrocyte membranes for reduced reticuloendothelial system uptake," Nanotechnology, 2016, 27 (8), 85106, 9 pages.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, 2016, 3, 107-110.
Regier et al., American Heart Association 2014 Scientific Sessions, 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, 2008, 2(2): p. 141-150.
Ribeiro et al., "Influence of the amino-acid sequence on the inverse temperature transition of elastin-like polypeptides," Biophysical Journal, 2009, 97, 312-320.
Richards et al., "Man's best friend: what can pet dogs teach US about non-Hodgkin lymphoma?" Inmunol Rev., 2016, 263 (1), 173-191.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, 2015, 17, 661-670.
Roopenian et al., "FcRn: the neonatal Fc receptor comes of age," Nat. Rev. Immunol., 2007, vol. 7, No. 9, 715-725.
Rosenberg et al., "Present and future innovations in radiation oncology," Surg Oncol Clin N Am, 2013, 22, 599-618.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Russo et al., "The role of neoadjuvant therapy in pancreatic cancer: a review," Future Oncol, 2016, 12, 669-685.
Ryerson et al., "Annual report to the nation on the status of cancer, 1975-2012, featuring the Increasing incidence of liver cancer," Cancer, 2016, 122, 1312-1337.
Saba et al., "A Comparative Oncology Study of Iniparib Defines Its Pharmacokinetic Profile and Biological Activity in a Naturally-Occurring Canine Cancer Model," PLoS One, 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, 2009, 131, 9304-9310.
Schaal et al., "Biopolymer ß-brachytherapy delivered with concomitant paclitaxel outperforms traditional x-ray radiation to include complete regression in multiple pancreatic tumor xenograft models through synergistic modulation of the tumor microenvironment," Poster #5831,2018.
Schaal et al., "Injectable polypeptide micelles that form radiation crosslinked hydrogels in situ for intratumoral radiotherapy," Journal of Controlled Release, 2016, 228, 58-66.
Schellenberg et al., "Gemcitabine chemotherapy and single-fraction stereotactic body radiotherapy for locally advanced pancreatic cancer," Int J Radiation Oncol Biol Phys, 2008, 72, 678-686.
Schellenberg et al., "Single-fraction stereotactic body radiation therapy and sequential gemcitabine for the treatment of locally advanced pancreatic cancer," Int J Radiation Oncology Biol Phys, 2011, 81, 181-188.
Schlaff et al., "Bringing the heavy: carbon ion therapy in the radiobiological clinical context," Radiation Oncology, 2014, 9, 1-18.
Schneider et al., "NIH Image to Imaged: 25 years of image analysis," Nature Methods, 2012, 9, 671-675.
Shadwick, "Mechanical design in arteries," J Exp Biol, 1999, 202, 3305-3313.
Shang et al., "pH-Dependent Protein Conformational Changes in Albumin:Gold Nanoparticle Bioconjugates: A Spectroscopic Study," Langmuir, 2007, 23 (5), 2714-2721.
Shao et al., "Super-resolution 3D microscopy of live whole cells using structured illumination," Nat Methods, 2011, 8, 1044-1046.
Siegel et al., "Absorbed fractions for electrons and beta particles in spheres of various sizes," J Nucl Med, 1994, 35, 152-156.
Silberstein et al., "The SNM Practice Guideline for Therapy of Thyroid Disease with $^{131}$I, 3.0," J Nucl Med, 2012, 53, 1-19.
Simnick et al., "In vivo tumor targeting by a NGR-decorated micelle of a recombinant diblock copolypeptide," J Control Release, 2011, 155, 144-151.
Simnick et al., "Morphing low-affinity ligands into high-avidity nanoparticles by thermally triggered self-assembly of a genetically encoded polymer," ACS Nano, 2010, 4, 2217-2227.
Sisson et al., "Radiation safety in the treatment of patients with thyroid diseases by radioiodine 1311: practice recommendations of the American Thyroid Association," Thyroid, 2011, 21, 335-346.
Sonawane et al., "Hydrazo linkages in pH responsive drug delivery systems," European Journal Pharmaceutical Sciences, 2017, 99, 45-65.
Sousa et al., "Production of a polar fish antimicrobial peptide in Escherichia coli using an ELP-inteintag," J Biotechnol, 2016, 234:83-89.
Sriraman et al., "Barriers to drug delivery in solid tumors," Tissue Barriers, 2014, 2, 2-10.
Stock et al., "Penile erectile function after permanent radioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, 2007, 20(11): p. 569-576.
Strohmaier et al., "Comparison of $^{60}$Co and $^{192}$Ir sources in HDR brachytherapy," J Contemp Brachyther, 2011, 3, 199-208.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human antitransferring receptor monoclonal antibody in pancreatic cancer mouse models," PLoS One, 2015, 10, 1-17.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, 2015, 16, 438-449.
Sun et al., "EUS-guided interstitial brachytherapy of the pancreas: a feasibility study," Gastrointestinal Endoscopy, 2005, 62, 775-779.

(56) References Cited

OTHER PUBLICATIONS

Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Sussman et al., "Porous implants modulate healing and induce shifts in local macrophage polarization in the foreign body reaction," Ann Biomed Eng, 2014, 42, 1508-1516.
Takalkar et al., "Radium-223 dichloride bone-targeted alpha particle therapy for hormone-refractory breast cancer metastatic to bone," Exp Hematol Oncol, 2014, 8, 23.
Tallarida, "Quantitative methods for assessing drug synergism," Genes & Cancer, 2011, 2, 1003-1008.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, 2006, 45, 9518-9530.
Tan et al., "Characterization of a new primary human pancreatic tumor line," Cancer investigation, 1986, 4, 15-23.
Tang et al., "Identification of PECAM-1 in solid tumor cells and its potential involvement in tumor cell adhesion to endothelium," J. Biol. Chem., 1993, 268, 22883-22894.
Teicher, "In vivo/ex vivo and in situ assays used in cancer research: a brief review," Toxicol. Pathol., 2009, 37 (1), 114-122.
Therasse et al., "New guidelines to evaluate the response to treatment in solid tumors," J Natl Cancer Inst, 2000, 92, 205-216.
Tompa et al., "Fuzzy complexes: polymorphism and structural disorder in protein-protein interactions," Trends Biochem Sci, 2008, 33, 2-8.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trakul et al., "Stereotactic body radiotherapy in the treatment of pancreatic cancer," Semin Radiat Oncol, 2014, 24, 140-147.
Trieu et al., "P0157 Preclinical evaluation of NBN-paclitaxel in pancreatic cancer xenograft models," Eur J Cancer, 2014, 50, e53.
Tu et al., "Stages in tropoelastin coalescence during synthetic elastin hydrogel formation," Micron, 2010, 41, 268-272.
Tward et al., "Survival of men with clinically localized prostate cancer treated with prostatectomy, brachytherapy, or no definitive treatment: impact of age at diagnosis," Cancer, 2006, 107, 2392-2400, doi:10.1002/cncr.22261.
Uchida et al., "Potential of adenovirus-mediated REIC/Dkk-3 gene therapy for use in the treatment of pancreatic cancer," Journal of Gastroenterology and Hepatology, 2014, 29, 973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci USA, 1970, 65, 845-852.
Urry et al., "Distortions in circular dichroism patterns of particulate (or membranous) systems," Arch Biochem Biophys, 1968, 128, 802-807.
Urry et al., "Temperature dependence of length of elastin and its polypentapeptide," Biochem Biophys Res Commun, 1986, 141, 749-755.
Urry, "Protein elasticity based on conformations of sequential polypeptides: The biological elastic fiber," J Protein Chemistry, 1984, 3, 403-436.
Valkenburg et al., "Targeting the tumour stroma to improve cancer therapy," Nature Reviews Clinical Oncology, 2018, 15, 366-381.
Van der Lee et al., "Classification of intrinsically disordered regions and proteins," Chem Rev, 2014, 114, 6589-6631.
Van Roey et al., "Short linear motifs: ubiquitous and functionally diverse protein interaction modules directing cell regulation," Chem Rev, 2014, 114, 6733-6778.
Van Roy, "Beyond E-cadherin: roles of other cadherin superfamily members in cancer," Nat Rev Cancer, 2014, 14, 121-134.
Vicini et al., "An interinstitutional and interspecialty comparison of treatment outcome data for patients with prostate carcinoma based on predefined prognostic categories and minimum follow-up," Cancer, 2002, 95, 2126-2135.
Volkova et al., "Anthracycline Cardiotoxicity: Prevalence, Pathogenesis and Treatment," Curr. Cardiol. Rev., 2011, vol. 7, No. 4, pp. 214-220.
Vrhovski et al., "Biochemistry of tropoelastin," Eur J Biochem, 1998, 258, 1-18.
Wang et al., "Extending Half Life of H-Ferritin Nanoparticle by Fusing Albumin Binding Domain for Doxorubicin Encapsulation," Biomacromolecules, 2018, 12, 19(3):773-781.
Wang et al., "Quantitative Mapping of the Spatial Distribution of Nanoparticles in Endo-Lysosomes by Local pH," Nano Lett., 2017, 17(2): 1226-1232.
Wang et al., "Size and dynamics of caveolae studied using nanoparticles in living endothelial cells," ACS nano, 2009, 3(12): p. 4110-4116.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wei et al., "Anticancer drug nanomicelles formed by self-assembling amphiphilic dendrimer to combat cancer drug resistance," Proceedings of the National Academy of Sciences of the United States of America, 2015, 112(10): 2978-2983.
Williams et al., "Targeted radionuclide therapy," Medical Physics, 2008, 35, 3062-3068.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wust et al., "Hyperthermia in combined treatment of cancer," The Lancet Oncology, 2002, 3, 487-497.
Xia et al., "Tunable self-assembly of genetically engineered silk—elastin-like protein polymers," Biomacromolecules, 2011, 12, 3844-3850.
Xu et al., "Genetically engineered block copolymers: influence of the length and structure of the coiled-coil blocks on hydrogel self-assembly," Pharm Res, 2008, 25, 674-682.
Xu et al., "Role of pancreatic stellate cells in pancreatic cancer metastasis," Am J of Pathology, 2010, 177, 2585-2596.
Yates et al., "Contemporary management of patients with high-risk non-muscle-invasive bladder cancer who fail intravesical BCG therapy," World journal of urology, 2011,29, 415-422.
Yeo et al., "Coacervation of tropoelastin," Adv Colloid Interface Sci, 2011, 167, 94-103.
Yokoe et al., "Albumin-conjugated PEG liposome enhances tumor distribution of liposomal doxorubicin in rats," International Journal of Pharmaceutics, 2008, 353(1-2): 28-34.
Yousefpour et al., "Co-opting biology to deliver drugs," Biotechnol Bioeng, 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett. 2018, 18(12): 7784-7793.
Yu et al., "Effectiveness and security of CT-guided percutaneous implantation of (125)I seeds in pancreatic carcinoma," The British journal of radiology, 2014, 87, 20130642, 7 pages.
Zhang et al., "Novel agents for pancreatic ductal adenocarcinoma: emerging therapeutics and future directions," Jounral of Hematology & Oncology, 2018, 11:14, 17 pages.
Zhao et al., "A new Bliss Independence model to analyze drug combination data," J Biomol Screen, 2014, 19, 817-821.

(56) References Cited

OTHER PUBLICATIONS

Zini et al., "Contemporary management of adrenocortical carcinoma," European urology, 2011, 60, 1055-1065.
International Search Report and Written Opinion for Application No. PCT/US2018/040409 dated Nov. 5, 2018 (16 pages).
United States Patent Office Action for U.S. Appl. No. 15/561,799 dated Dec. 27, 2018 (8 pages).
European Patent Office Extended Search Report for Application No. 16833900.0 dated Feb. 12, 2019 (7 pages).
Alarcon et al., "Exendin 4 controls insulin production in rat islet beta cells predominantly by potentiation of glucose-stimulated proinsulin biosynthesis at the translational level," Diabetologia, 2006, 49(12):2920-2929.
American Diabetes Association (2018) Standards of medical care in diabetes—2018. Diabetes Care 41(Suppl 1):S1-S159.
Arner et al., "FGF21 attenuates lipolysis in human adipocytes—a possible link to improved insulin sensitivity," FEBS Lett, 2008, 582(12):1725-1730.
Badi, "Non-linear PEG-based thermoresponsive polymer systems," Progress in Polymer Science, 2017, 66, 54-79.
Baggio et al., "Biology of Incretins: GLP-1 and GIP," Gastroenterology, 2007, 132(6):2131-2157.
Beenken et al., "The FGF family: biology, pathophysiology and therapy," Nat Rev Drug Discov, 2009, 8(3):235-253.
Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, 2017, 27(12):1-9.
Bobo et al., "Nanoparticle-based medicines: a review of FDA-approved materials and clinical trials to date." Pharmaceutical research 33.10 (2016): 2373-2387.
Buteau et al., "Glucagon-like peptide-1 prevents beta cell glucolipotoxicity," Diabetologia, 2004, 47(5):806-815.
Butler et al., "β-Cell Deficit and Increased β-Cell Apoptosis in Humans With Type 2 Diabetes," Diabetes, 2003, 52(1):102-110.
Cabrera et al., "Automated, High-Throughput Assays for Evaluation of Human Pancreatic Islet Function," Cell Transplant, 2008, 16(10):1039-1048.
Cabrera et al., "Glutamate Is a Positive Autocrine Signal for Glucagon Release," Cell Metab, 2008, 7(6):545-554.
Centers for Disease Control and Prevention (2017) National Diabetes Statistics Report, 2017. ed U.S. Dept of Health and Human Services (Atlanta).
Chatterjee et al., "Type 2 diabetes," The Lancet, 2017, 389(10085): 2239-2251.
Chilkoti et al., "Stimulus responsive elastin biopolymers: applications in medicine and biotechnology," Curr Opin Chem Biol, 2006, 10(6):652-657.
Coskun et al., "Fibroblast Growth Factor 21 Corrects Obesity in Mice," Endocrinology, 2008, 149(12):6018-6027.
Day et al., "A new glucagon and GLP-1 co-agonist eliminates obesity in rodents," Nat Chem Biol, 2009, 5:749.
Deyoung et al.."Encapsulation of exenatide in poly-(D,L-lactide-co-glycolide) microspheres produced an investigational long-acting once-weekly formulation for type 2 diabetes," Diabetes Technol Ther, 2011, 13, 1145-1154.
Ding et al., "βKlotho Is Required for Fibroblast Growth Factor 21 Effects on Growth and Metabolism," Cell Metab, 2012, 16(3):387-393.
Drucker "Mechanisms of Action and Therapeutic Application of Glucagon-like Peptide-1," Cell Metab, 2018, 27(4):740-756.
Drucker, "Incretin action in the pancreas: potential promise, possible perils, and pathological pitfalls," Diabetes, 2013, 62, 3316-3323.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.

El-Assaad et al., "Saturated Fatty Acids Synergize with Elevated Glucose to Cause Pancreatic β-Cell Death," Endocrinology, 2003, 144(9):4154-4163.
Finan et al., "A rationally designed monomeric peptide triagonist corrects obesity and diabetes in rodents," Nat Med, 2015, 21:27-36.
Finan et al., "Unimolecular Dual Incretins Maximize Metabolic Benefits in Rodents, Monkeys, and Humans," Sci Transl Med, 2013, 5(209):209ra151.
Fosgerau et al., "Peptide therapeutics: current status and future directions," Drug Discovery Today, 2015, 20, 122-128.
Gaich et al., "The Effects of LY2405319, an FGF21 Analog, in Obese Human Subjects with Type 2 Diabetes," Cell Metab, 2013, 18(3):333-340.
Ganson et al., "Pre-existing anti-polyethylene glycol antibody linked to first-exposure allergic reactions to pegnivacogin, a PEGylated RNA aptamer," J Allergy Clin Immunol, 2016, 137(5): 1610-1613, e1617.
Gao, "Site-specific andin situgrowth of stealth polymer conjugates of proteins with significally improved pharmacology," Journal of Controlled Release, 2013, 172(1):e116-e117.
Gilroy et al., "Fusion of fibroblast growth factor 21 to a thermally responsive biopolymer forms an injectable depot with sustained anti-diabetic action," J Control Release, 2018, 277:154-164.
Gu et al., "Enzymatic Synthesis of Nucleobase-Modified Single-Stranded DNA Offers Turnable Resistance to Nuclease Degradation," Biomacromolecules, 2018, 19, 3525-3535.
Gu et al., "Photocontrolled micellar aggregation of amphiphilic DNA-azobenzene conjugates," Colloids Surfaces B: Biointerfaces, 2015, 135, 126-132.
Ha et al., "Immunoglobulin Fc Heterodimer Platform Technology: From Design to Applications in Therapeutic Antibodies and Proteins," Front Immunol, 2016, 7(394) (in English).
Hampp et al., "Use of Antidiabetic Drugs in the U.S., 2003-2012," Diabetes Care, 2014, 37: 1367-1374.
Hart et al., "Attenuation of FGF signalling in mouse B-cells leads to diabetes," Nature, 2000, 408:864.
Ito et al., "Impaired negative feedback suppression of bile acid synthesis in mice lacking pKlotho," J Clin Invest, 2005, 115(8):2202-2208.
Johnson et al., "Fibroblast Growth Factor 21 Reduces the Severity of Cerulein-Induced Pancreatitis in Mice," Gastroenterology, 2009, 137(5):1795-1804.
Kaspar et al., "Future directions for peptide therapeutics development," Drug Discovery Today, 2013, 18, 807-817.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, 2015, 26(11):608-617.
Kharitonenkov et al., "Fibroblast growth factor 21 night watch: advances and uncertainties in the field," J Intern Med, 2016, 281(3):233-246.
Kharitonenkov et al., "Inventing new medicines: The FGF21 story," Mol Metab, 2014, 3(3):221-229.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, 2007, 30, 1487-93.
Kurosu et al., "Tissue-specific Expression of βKlotho and Fibroblast Growth Factor (FGF) Receptor Isoforms Determines Metabolic Activity of FGF19 and FGF21," J Biol Chem, 2007, 282(37):26687-26695.
Laybutt et al., "Endoplasmic reticulum stress contributes to beta cell apoptosis in type 2 diabetes," Diabetologia, 2007, 50(4):752-763.
Lee et al., "Nanoparticle-Delivered Chemotherapy: Old Drugs in New Packages." Oncology (Williston Park, NY) 31.3 (2017): 198-208.

(56) References Cited

OTHER PUBLICATIONS

Lee et al., "Structures of β-klotho reveal a 'zip code'-like mechanism for endocrine FGF signaling," Nature, 2018, 553:501-505.
Leibowitz et al., "Glucose-Regulated Proinsulin Gene Expression Is Required for Adequate Insulin Production during Chronic Glucose Exposure," Endocrinology, 2002, 143(9):3214-3220.
Li et al., "Prediction of solvent-induced morphological changes of polyelectrolyte diblock copolymer micelles," Soft Matter, 2015, 11(42): 8236-45.
Lin et al., "Adiponectin Mediates the Metabolic Effects of FGF21 on Glucose Homeostasis and Insulin Sensitivity in Mice," Cell Metab, 2013, 17(5):779-789.
Lin et al., "Functional expression of a biologically active fragment of soluble gp130 as an ELP-fusion protein in transgenic plants: purification via inverse transition cycling," Biochem J, 2006, 398(3):577-583.
Lin et al., "Statistical properties of the traditional algorithm-based designs for phase I cancer clinical trials," Biostatistics, 2001,2(2):203-215.
Lutz et al., "About the Phase Transitions in Aqueous Solutions of Thermoresponsive Copolymers and Hydrogels Based on 2-(2-metholxyethoxy)ethyl Methacrylate and Oligo(ethylene glycol) Methacrylate," Macromolecules, 2007, 40, 2503-2508.
Lutz et al., "Preparation of Ideal PEG Analogues with a Tunable Thermosensitivity by Controlled Radical Copolymerization of 2-(2-Metholoxyethoxy)ethyl Methacrylate and Oligo(ethylene glycol) Methacrylate," Macromolecules, 2006, 39, 893-896.
Magnusson et al., "Ion-Sensitive "Isothermal" Responsive Polymers Prepared in Water," Journal of the American Chemical Society, 2008, 130, 10852-10853.
Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, 2008, 93(12):4810-4817.
Meier et al., "Determination of Optimal Sample Size for Quantification of β-Cell Area, Amyloid Area and -Cell Apoptosis in Isolated Islets," J Histochem Cytochem, 2015, 63(8):663-673.
Mu et al., "FGF21 Analogs of Sustained Action Enabled by Orthogonal Biosynthesis Demonstrate Enhanced Antidiabetic Pharmacology in Rodents," Diabetes, 2012, 61(2):505-512.
Nanoprecision Medical, "Pipeline, Type II Diabetes," <http://www.nanoprecisionmedical.com/pipeline/diabetes> webpage available as early as Aug. 2018.
Nauck "Glucagon-like Peptide 1 (GLP-1) in the Treatment of Diabetes," Horm Metab Res, 2004, 36(11/12):852-858 (in English).
Nies et al., "Fibroblast Growth Factor Signaling in Metabolic Regulation," Front Endocrinol, 2016, 6(193) (in English).
Ozer et al., "Site-Specific and Stoichiometric Stealth Polymer Conjugates of Therapeutic Peptides and Proteins," Bioconjug Chem, 2017, 28(3):713-723.
Pang et al., "A Modular Method for the High-Yield Synthesis of Site-Specific Protein-Polymer Therapeutics," Angew Chem Int Ed Engl, 2016, 55, 10296-10300.
Park et al., "Exendin-4 and exercise improve hepatic glucose homeostasis by promoting insulin signaling in diabetic rats," Metabolism, 2010, 59, 123-133.
Poitout et al., "Glucolipotoxicity: Fuel Excess and -Cell Dysfunction," Endocr Rev, 2008, 29(3):351-366.
Potthoff et al., "Endocrine fibroblast growth factors 15/19 and 21: from feast to famine," Genes Dev, 2012, 26(4):312-324.
Qi et al., "A brush-polymer conjugate of exendin-4 reduces blood glucose for up to five days and eliminates poly(ethylene glycol) antigenicity," Nat Biomed Eng, 2016, 1:0002.
Ray et al., "Aptamer-mediated delivery of chemotherapy to pancreatic cancer cells." Nucleic acid therapeutics, 2012, 22(5): 295-305.
Riedel et al., "Engineered glucagon-like peptide-1-producing hepatocytes lower plasma glucose levels in mice," Am J Physiol Endocrinol Metab, 2009, 296(4):E936-E944.
Rodriguez-Diaz et al., "Alpha cells secrete acetylcholine as a non-neuronal paracrine signal priming beta cell function in humans," Nat Med, 2011, 17:888-892.
Schwendeman et al., "Injectable controlled release depots for large molecules," J Control Release, 2014, 190, 240-253.
Shusharina et al., "Micelles of Diblock Copolymers with Charged and Neutral Blocks: Scaling and Mean-Field Lattice Approaches," Macromolecules, 2000, 33(10): 3892-3901.
Singhal et al., "Fibroblast Growth Factor 21 (FGF21) Protects against High Fat Diet Induced Inflammation and Islet Hyperplasia in Pancreas," PLoS One, 2016, 11(2):e0148252.
Smith et al., "The Role of Beta Cell Glucagon-like Peptide-1 Signaling in Glucose Regulation and Response to Diabetes Drugs," Cell Metab, 2014, 19(6):1050-1057.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, 2017, 158(5):1314-1327.
Sun et al., "Autofluorescence Imaging of Living Pancreatic Islets Reveals Fibroblast Growth Factor-21 (FGF21)-lnduced Metabolism," Biophys J, 2012, 103(11):2379-2388.
Sun et al., "On the Thermally Reversible Dynamic Hydration Behavior of Oligo(ethylene glycol) Methacrylate-Based Polymers in Water," Macromolecules, 2013, 46, 236-246.
Talukdar et al., "A Long-Acting FGF21 Molecule, PF-05231023, Decreases Body Weight and Improves Lipid Profile in Non-human Primates and Type 2 Diabetic Subjects," Cell Metab, 2016, 23(3):427-440.
Tang et al., "Enzymatic Polymerization of High Molecular Weight DNA Amphiphiles That SelfAssemble into Star-Like Micelles," Advanced Materials, 2014, 26(19): 3050-3054.
Tang et al., "High-Molecular-Weight Polynucleotides by Transferase-Catalyzed Living Chain-Growth Polycondensation," Angew. Chern., 2017, 56(24): 6778-6782.
Tomiyama et al., "Relevant use of Klotho in FGF19 subfamily signaling system in vivo," Proc Natl Acad Sci USA, 2010, 107(4): 1666-71.
Tschöp et al., "Unimolecular Polypharmacy for Treatment of Diabetes and Obesity," Cell Metab, 2016, 24(1):51-62.
Urry, "Free energy transduction in polypeptides and proteins based on inverse temperature transitions," Prog Biophys Mol Biol, 1992, 57(1):23-57.
Vlieghe et al., "Synthetic therapeutic peptides: science and market," Drug Discovery Today, 2010, 15, 40-56.
Wali et al., "Measuring Death of Pancreatic Beta Cells in Response to Stress and Cytotoxic T Cells," Methods in Molecular Biology, 2015, 1292:165-176.
Wei et al., "Fibroblast growth factor 21 promotes bone loss by potentiating the effects of peroxisome proliferator-activated receptor γ," Proc Natl Acad Sci USA, 2012, 109(8):3143-3148.
Wente et al., "Fibroblast Growth Factor-21 Improves Pancreatic β-Cell Function and Survival by Activation of Extracellular Signal13 Regulated Kinase 1/2 and Akt Signaling Pathways," Diabetes, 2006, 55(9):2470-2478.
Xiaodong et al., "FGF21 Is Not a Major Mediator for Bone Homeostasis or Metabolic Actions of PPARα and PPARγ Agonists," J Bone Miner Res, 2017, 32(4):834-845.
Xu et al., "Downregulation of GLP-1 and GIP Receptor Expression by Hyperglycemia," Diabetes, 2007, 56(6): 1551-58.
Xu et al., "Fibroblast Growth Factor 21 Reverses Hepatic Steatosis, Increases Energy Expenditure, and Improves Insulin Sensitivity in Diet-Induced Obese Mice," Diabetes, 2009, 58(1):250-259.
Yamamoto et al., "ATRP Synthesis of Thermally Responsive Molecular Brushes from Oligo(ethylene oxide) Methacrylates," Macromolecules, 2007, 40, 9348-9353.
Yang et al., "Long Term Exendin-4 Treatment Reduces Food Intake and Body Weight and Alters Expression of Brain Homeostatic and Reward Markers," Endocrinology, 2014, 155, 3473-3483.
Yusta et al., "GLP-1 receptor activation improves p cell function and survival following induction of endoplasmic reticulum stress," Cell Metab, 2006, 4(5):391-406.

(56) References Cited

OTHER PUBLICATIONS

Zhang et al., "In Depth Analysis on the Unusual Multistep Aggregation Process of Oligo(ethylene glycol) Methacrylate-Based Polymers in Water," Macromolecules, 2014, 47, 4728-4737.
Zununi Vahed et al., "Targeted cancer drug delivery with aptamer-functionalized polymeric nanoparticles," Journal of drug targeting, 2019, 27(3):292-299.
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
Aaron et al., "Elastin as a Random-Network Elastomer—a Mechanical and Optical Analysis of Single Elastin Fibers," Biopolymers, 1981, 20(6):1247-1260.
Allen et al., "Liposomal drug delivery systems: from concept to clinical applications," Adv Drug Deliv Rev, 2013, 65(1):36-48.
Anselmo et al., "Nanoparticles in the clinic, " Bioeng Transl Med, Jun. 2016, 1(1):10-29.
Arami et al., "In vivo delivery, pharmacokinetics, biodistribution and toxicity of iron oxide nanoparticles," Chem Soc Rev, Dec. 2015, 44(23):8576-8607.
Astete et al., "Synthesis and characterization of PLGA nanoparticles," Journal of Biomaterials Science, Polymer Edition 2006, 17(3):247-289.
Babu, "The contribution of intrinsically disordered regions to protein function, cellular complexity, and human disease," Biochem Soc Trans, Oct. 2016, 44(5):1185-1200.
Bae et al., "Targeted drug delivery to tumors: myths, reality and possibility," J Control Release, 2011, 153(3):198-205.
Balu et al., "An16-resilin: an advanced multi-stimuli-responsive resilin-mimetic protein polymer," Acta Biomater, Nov. 2014, 10:4768-4777.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, 2011, 104:489-507.
Banjade et al., "Phase transitions of multivalent proteins can promote clustering of membrane receptors," Elife, Oct. 2014, 3:e04123.
Banskota et al., "Genetically encoded stealth nanoparticles of a zwitterionic polypeptidepaclitaxel conjugate have wider therapeutic window than Abraxane in multiple tumor models," Nano Lett, Mar. 2020, 20(4):2396-2409.
Bates et al., "Block copolymer thermodynamics: theory and experiment," Annu Rev. Phys. Chem., 1990, 41:525-57.
Best, "Computational and theoretical advances in studies of intrinsically disordered proteins," Curr Opin Struct Biol, Feb. 2017, 42:147-154.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Boeynaems et al., "Protein Phase Separation: A New Phase in Cell Biology," Trends Cell Biol, Jun. 2018, 28(6):420-435.
Borst et al., "The Therapeutic Antibody LM609 Selectively Inhibits Ligand Binding to Human αVβ3 Integrin via Steric Hindrance," Structure, Nov. 2017, 25(11):1732-1739.e5.
Bowditch et al., "Identification of a novel integrin binding site in fibronectin. Differential utilization by β3 integrins," Journal of Biological Chemistry, 1994, 269(14):10856-10863.
Brangwynne et al., "Polymer physics of intracellular phase transitions," Nature Physics, Nov. 2015, 11(11):899-904.

Brannon-Peppas et al., "Nanoparticle and targeted systems for cancer therapy," Advanced Drug Delivery Reviews, 2012, 64(11):206-212.
Broome et al., "Expanding the utility of beta-galactosidase complementation: piece by piece," Mol Pharm, 2010, 7(1):60-74.
Burke et al., "Multimodal nanoparticle imaging agents: design and applications," Philos Trans A Math Phys Eng Sci, Nov. 2017, 375:20170261.
Carreiras et al., "Expression and localization of alpha v integrins and their ligand vitronectin in normal ovarian epithelium and in ovarian carcinoma," Gynecol Oncol, 1996, 62(2):260-7.
Champion et al., "Particle shape: a new design parameter for micro- and nanoscale drug delivery carriers," J Control Release, 2007, 121(1-2):3-9.
Champion et al., "Role of particle size in phagocytosis of polymeric microspheres," Pharm Res, 2008, 25(8):1815-21.
Champion et al., "Role of target geometry in phagocytosis," Proc Natl Acad Sci USA, 2006, 103(13):4930-4.
Champion et al., "Shape induced inhibition of phagocytosis of polymer particles," Pharm Res, 2009, 26(1):244-9.
Chen, "Small-molecule delivery by nanoparticles for anticancer therapy," Trends Mol Med, 2010, 16(12):594-602.
Chithrani et al., "Elucidating the mechanism of cellular uptake and removal of protein-coated gold nanoparticles of different sizes and shapes," Nano letters, 2007, 7(6):1542-1550.
Conner et al., "Regulated portals of entry into the cell," Nature, 2003, 422(6927):37-44.
Costa et al., "Active Targeting of Cancer Cells by Nanobody Decorated Polypeptide Micelle with Bio-orthogonally Conjugated Drug," Nano letters, Dec. 2018, 19(1):247-254.
Dai et al., "Versatile biomanufacturing through stimulus-responsive cell-material feedback," Nature chemical biology, Sep. 2019, 15(10):1017-1024.
Dalhaimer et al., "Single Molecule Visualization of Stable, Stiffness-Tunable, Flow-Conforming Worm Micelles," Macromolecules, 2003, 36(18):6873-6877.
Das et al., "Conformations of intrinsically disordered proteins are influenced by linear sequence distributions of oppositely charged residues," Proc Natl Acad Sci USA, 2013, 110(33):13392-13397.
Dignon et al., "Relation between single-molecule properties and phase behavior of intrinsically disordered proteins," Proc Natl Acad Sci USA, Oct. 2018, 115(40):9929-9934.
Dignon et al., "Sequence determinants of protein phase behavior from a coarse-grained model," PLoS Comput Biol, Jan. 2018, 14(1):e1005941.
Duan et al., "Improving the thermostability and catalytic efficiency of Bacillus deramificans pullulanase by site-directed mutagenesis," Appl Environ Microbiol, 2013, 79(13):4072-4077.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Ehlerding et al., "Biodegradable and Renal Clearable Inorganic Na No. particles," AdvSci (Weinh), Feb. 2016, 3(2):1500223.
Elbaum-Garfinkle et al., "The disordered P granule protein LAF-1 drives phase separation into droplets with tunable viscosity and dynamics," Proc Natl Acad Sci USA, Jun. 2015, 112(23):7189-7194.
Elsabahy et al., "Design of polymeric nanoparticles for biomedical delivery applications," Chem Soc Rev, 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, 2015, Chapter Six, vol. 98, pp. 169-221.
Farokhzad et al., "Targeted nanoparticle-aptamer bioconjugates for cancer chemotherapy in vivo," Proc Natl Acad Sci U S A, 2006, 103(16):6315-20.
Franzmann et al., "Phase separation of a yeast prion protein promotes cellular fitness," Science, Jan. 2018, 359(6371):eaao5654.

(56) References Cited

OTHER PUBLICATIONS

Garcia Quiroz et al., "Syntaxof Phase Transition Peptide Polymers with LCST and UCST Behavior," Jan. 1, 2013, Retrieved from the Internet: URL: https://dukespace.lib.duke.edu/dspace/bitstream/handle/10161/7256/GarciaQuirozduke0066D 11972.pdf?sequence=1&isAllowed=y.

Geng et al., Shape effects of filaments versus spherical particles in flow and drug delivery, Nat Nanotechnol, 2007, 2(4):249-55.

Gilbreth et al., "Structural insights for engineering binding proteins based on non-antibody scaffolds," Curr Opin Struct Biol, 2012, 22(4):413-20.

Gillies et al., "Dendrimers and dendritic polymers in drug delivery," Drug Discovery Today, 2005, 10(1):35-43.

Goldsmith et al., "Enzyme engineering: reaching the maximal catalytic efficiency peak," Curr Opin Struct Biol, Dec. 2017, 47:140-150.

Graff et al., "Theoretical analysis of antibody targeting of tumor spheroids: importance of dosage for penetration, and affinity for retention," Cancer Research, 2003, 63(6):1288-1296.

Gratton et al., "The effect of particle design on cellular internalization pathways," Proc Natl Acad Sci U S A, 2008, 105(33):11613-8.

Gu et al., "Precise engineering of targeted nanoparticles by using self-assembled biointegrated block copolymers," Proc Natl Acad Sci U S A, 2008, 105(7):2586-91.

Hofmann et al., "A kinetic study on the enzymatic hydrolysis of fluoresceindiacetate and fluorescein-di-β-D-galactopyranoside," Analytical biochemistry, 1983, 131(1):180-186.

Holehouse et al.."Functional Implications of Intracellular Phase Transitions," Biochemistry, May 2018, 57(17):2415-2423.

Huber et al., "Designer amphiphilic proteins as building blocks for the intracellular formation of organelle-like compartments," Nat Mater, Jan. 2015, 14(1):125-132.

Jiang et al., "Nanoparticle-mediated cellular response is size-dependent," Nat Nanotechnol, 2008, 3(3):145-50.

Jokerst et al., "Nanoparticle PEGylation for imaging and therapy," Nanomedicine (Lond), 2011, 6(4):715-28.

Jurney et al., "Unique size and shape-dependent uptake behaviors of non-spherical nanoparticles by endothelial cells due to a shearing flow," J Control Release, Jan. 2017, 245:170-176.

Kamaly et al., "Targeted polymeric therapeutic nanoparticles: design, development and clinical translation," Chem Soc Rev, 2012, 41(7):2971-3010.

Karagoz et al., "Polymerization-Induced Self-Assembly (PISA)—control over the morphology of nanoparticles for drug delivery applications," Polym. Chem., Jan. 2014, 5(2):350-355.

Kataoka et al., "Block copolymer micelles for drug delivery: Design, characterization and biological significance," Advanced Drug Delivery Reviews, 2001, 47:113-131.

Kelly et al., "Shape-specific, monodisperse nano-molding of protein particles," J Am Chem Soc, 2008, 130(16):5438-9.

Kesharwani et al., "Dendrimer as nanocarrier for drug delivery," Progress in Polymer Science, Feb. 2014, 39(2):268-307.

Kulkarni et al., "Design of lipid nanoparticles for in vitro and in vivo delivery of plasmid DNA," Nanomedicine, May 2017, 13(4):1377-1387.

Lee et al., "Polymersomes for drug delivery: design, formation and characterization," J Control Release, 2012, 161(2):473-83.

Lewis et al., "Use of digitized video microscopy with a fluorogenic enzyme substrate to demonstrate cell-and compartment-specific gene expression in Salmonella enteritidis and Bacillus subtilis," Molecular microbiology, 1994, 13:655-662.

Li et al., "Phase transitions in the assembly of multivalent signalling proteins," Nature, 2012, 483(7389):336-340.

Li et al., "Tunable Assembly of Protein-Microdomains in Living Vertebrate Embryos," Advanced Biosystems, Oct. 2018, 2(10):1800112.

Lin et al., "Formation and Maturation of Phase-Separated Liquid Droplets by RNA-Binding Proteins," Mol Cell, Oct. 2015, 602):208-219.

Lin et al., "Intrinsically disordered sequences enable modulation of protein phase separation through distributed tyrosine motifs," J Biol Chem, Nov. 2017, 292(46):19110-19120.

Lin et al., "Phase Separation and Single-Chain Compactness of Charged Disordered Proteins Are Strongly Correlated," Biophys J, May 2017, 112(10):2043-2046.

Lin et al., "Sequence-Specific Polyampholyte Phase Separation in Membraneless Organelles," Phys Rev Lett, Oct. 2016, 117(17):178101.

Liong et al., "Multifunctional inorganic nanoparticles for imaging, targeting, and drug delivery," ACS Nano, 2008, 2(5):889-96.

Liu et al., "Integrin $\alpha v\beta$-Targeted Cancer Therapy," Drug Dev Res, 2008, 69(6):329-339.

Loh et al., "Utilising inorganic nanocarriers for gene delivery," Biomater Sci, Jan. 2016, 4(1):70-86.

Lopresti et al., "Polymersomes: nature inspired nanometer sized compartments," Journal of Materials Chemistry 2009, 19(22):3576-3590.

Lukyanov et al., "Tumor-targeted liposomes: doxorubicin-loaded long-circulating liposomes modified with anti-cancer antibody," J Control Release, 2004, 100(1):135-44.

Lyons et al., "Comparisons of Recombinant Resilin-like Proteins: Repetitive Domains Are Sufficient to Confer Resilin-like Properties," Biomacromolecules, 2009, 10(11):3009-3014.

Lyons et al., "Design and facile production of recombinant resilin-like polypeptides: Gene construction and a rapid protein purification method," Protein Engineering Design & Selection, 2007, 20(1):25-32.

Maeda et al., "Tumoritropic and lymphotropic principles of macromolecular drugs," Critical reviews in therapeutic drug carrier systems, 1989, 6(3):193-210.

Maeda, "The enhanced permeability and retention (EPR) effect in tumor vasculature: the key role of tumor-selective macromolecular drug targeting," Advances in Enzyme Regulation, 2001, 41(1):189-207.

Malam et al., "Liposomes and nanoparticles: nanosized vehicles for drug delivery in cancer," Trends Pharmacol Sci 2009, 30(11):592-9.

Manders et al., "Dynamics of three-dimensional replication patterns during the S-phase, analysed by double labelling of DNA and confocal microscopy," Journal of cell science, 1992, 103(Pt 3):857-862.

Mao et al., "Net charge per residue modulates conformational ensembles of intrinsically disordered proteins," Proc Natl Acad Sci U S A, 2010, 107(18):8183-8188.

Masood, "Polymeric nanoparticles for targeted drug delivery system for cancer therapy," Mater Sci Eng C Mater Biol Appl, Mar. 2016, 60:569-578.

Mastria et al., "Nanoparticle formulation improves doxorubicin efficacy by enhancing host antitumor immunity," J Control Release, Jan. 2018, 269:364-373.

McKenzie et al., "Multivalent Binding of a Ligand-Coated Particle: Role of Shape, Size, and Ligand Heterogeneity," Biophys J, Apr. 2018, 114(8):1830-1846.

Meng et al., "Stimuli-responsive polymersomes for programmed drug delivery," Biomacromolecules, 2009, 10(2):197-209.

Merkel et al., "Using mechanobiological mimicry of red blood cells to extend circulation times of hydrogel microparticles," Proc Natl Acad Sci U S A, 2011, 108(2):586-91.

Mitragotri et al., "Physical approaches to biomaterial design," J. Nat Mater, 2009, 8(1): 15-23.

Modery et al., "Heteromultivalent liposomal nanoconstructs for enhanced targeting and shearstable binding to active platelets for site-selective vascular drug delivery," Biomaterials, 2011, 32(35):9504-9514.

Molliex et al., "Phase separation by low complexity domains promotes stress granule assembly and drives pathological fibrillization," Cell, Sep. 2015, 163(1):123-133.

Moosmann et al., "Alpha complementation of LacZ in mammalian cells," Nucleic Acids Res, 1996, 24(6):1171-1172.

Mozhdehi et al., "Genetically Encoded Cholesterol-Modified Polypeptides," Journal of the American Chemical Society, Jan. 2019, 141(2):945-951.

(56) References Cited

OTHER PUBLICATIONS

Mozhdehi et al., "Genetically encoded lipid-polypeptide hybrid biomaterials that exhibit temperature-triggered hierarchical self-assembly," Nature chemistry, May 2018, 10(5):496-505.
Muiznieks et al., "Proline periodicity modulates the self-assembly properties of elastin-like polypeptides," J Biol Chem, 2010, 285(51):39779-39789.
Muro, "Challenges in design and characterization of ligand-targeted drug delivery systems," J Control Release, 2012, 164(2):125-37.
Napier et al., "Nanoparticle drug delivery platform," Journal of Macromolecular Science, Part C: Polymer Reviews, 2007, 47(3):321-327.
Nayeem et al., "Engineering enzymes for improved catalytic efficiency: a computational study of site mutagenesis in epothilone-B hydroxylase," Protein Eng Des Sei, 2009, 22(4):257-266.
Ni et al., "Engineering of inorganic nanoparticles as magnetic resonance imaging contrast agents," Chem Soc Rev, Nov. 2017, 46(23):7438-7468.
Niu et al., "The role of adhesion molecules, αVβ, av5 and their ligands in the tumor cell and endothelial cell adhesion," Eur J Cancer Prev, 2007, 16(6):517-27.
Nott et al., "Phase transition of a disordered nuage protein generates environmentally responsive membraneless organelles," Mol Cell, Mar. 2015, 57(5):936-947.
Ortega et al., "Hydrodynamic properties of rodlike and dislike particles in dilute solution," The Journal of Chemical Physics, 2003, 119(18):9914-9919.
Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Pardridge, "The blood-brain barrier: bottleneck in brain drug development," NeuroRx, 2005, 2(1):3-14.
Parker et al., "Antibody mimics based on human fibronectin type three domain engineered for thermostability and high-affinity binding to vascular endothelial growth factor receptor two," Protein Eng Des Sei, 2005, 18(9):435-44.
Pastuszka et al., "A tunable and reversible platform for the intracellular formation of genetically engineered protein microdomains," Biomacromolecules, 2012, 13(11):3439-3444.
Peng et al., "Length-dependent prediction of protein intrinsic disorder," BMC Bioinformatics, 2006, 7:208.
Petros et al., "Strategies in the design of nanoparticles for therapeutic applications," Nat Rev Drug Discov, 2010, 9(8):615-27.
Qamar et al., "FUS Phase Separation Is Modulated by a Molecular Chaperone and Methylation of Arginine Cation-pi Interactions," Cell, Apr. 2018, 173(3):720-734.e15.
Quiroz et al., "Intrinsically disordered proteins access a range of hysteretic phase separation behaviors," Scientific advances, Oct. 2019, 5(10):eaax5177.
Ravikumar et al., "Mimicking adhesive functionalities of blood platelets using ligand-decorated liposomes," Bioconjugate chemistry, 2012, 23(6):1266-1275.
Rolland et al., "Direct fabrication and harvesting of monodisperse, shape-specific nanobiomaterials," J Am Chem Soc, 2005, 127(28):10096-100.
Rosenholm et al., "Towards multifunctional, targeted drug delivery systems using mesoporous silica nanoparticles—opportunities & challenges," Nanoscale, 2010, 2(10):1870-83.
Rosier et al., "Advanced drug delivery devices via self-assembly of amphiphilic block copolymers," Advanced Drug Delivery Reviews, 2001, 53:95-108.
Ryu et al., "Elastin-like polypeptide for improved drug delivery for anticancer therapy: preclinical studies and future applications," Expert Opinion on Drug Delivery, 2014, 12(4):653-667.
Sanna et al., "Targeted therapy using nanotechnology: focus on cancer," Int J Nanomedicine, Jan. 2014, 9:467-83.

Schnell et al., "Expression of integrin av3 in gliomas correlates with tumor grade and is not restricted to tumor vasculature," Brain Pathol, 2008, 18(3):378-86.
Sharma et al., "Dendrimer nanoarchitectures for cancer diagnosis and anticancer drug delivery," Drug DiscovToday, Feb. 2017, 22(2):314-326.
Sharma et al., "PLGA-based nanoparticles: A new paradigm in biomedical applications," TrAC Trends in Analytical Chemistry, Jun. 2016, 80:30-40.
Sharma et al., "Polymer particle shape independently influences binding and internalization by macrophages," Journal of Controlled Release, 2010, 147(3):408-412.
Shi et al., "Triggered sorting and co-assembly of genetically engineered protein microdomains in the cytoplasm," Adv Mater, 2014, 26(3):449-454.
Shin et al., "Liquid phase condensation in cell physiology and disease," Science, Sep. 2017, 357(6357):eaaf4382.
Sickmeier et al., "DisProt: the Database of Disordered Proteins," Nucleic Acids Res, 2007, 35:D786-793.
Simon et al., "Engineered Ribonucleoprotein Granules Inhibit Translation in Protocells," Molecular cell, Jul. 2019, 75(1):66-75.
Simon et al., "Programming molecular self-assembly of intrinsically disordered proteins containing sequences of low complexity," Nat Chem, Jun. 2017, 9(6):509-515.
Skerra, "Alternative non-antibody scaffolds for molecular recognition," Curr Opin Biotechnol, 2007, 18(4):295-304.
Smits et al., "Elastin-Like Polypeptide Based Nanoparticled: Design Rationale Toward Nanomedicine," Macromolecular Bioscience, 2014, 15(1):36-51.
Steichen et al., "A Review of Current Nanoparticle and Targeting Moieties for the Delivery of Cancer Therapeutics," Eur J Pharm Sci, 2013, 48(3):416-27.
Strulson et al., "RNA catalysis through compartmentalization," Nat Chem, 2012, 4(11):941-946.
Suk et al., "PEGylation as a Strategy for Improving Nanoparticle-Based Drug and Gene Delivery ," Adv Drug Deliv Rev, Apr. 2016, 99(Pt A):28-51.
Swider et al., "Customizing Poly(lactic-Co-Glycolic Acid) Particles for Biomedical Applications," Acta Biomater, Jun. 2018, 73:38-51.
Talelli et al., "Core-Crosslinked Polymeric Micelles: Principles, Preparation, Biomedical Applications and Clinical Translation," Nano Today, Feb. 2015, 10(1):93-117.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, 2013, 1(1):e24360.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, 2011, 32(33):8462-73.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, 2010, 1804(6):1231-1264.
Vazquez-Lombardi et al., "Challenges and Opportunities for Non-Antibody Scaffold Drugs," Drug DiscovToday, Oct. 2015, 20(10):1271-83.
Venkataraman et al., "The Effects of Polymeric Nanostructure Shape on Drug Delivery," Adv Drug Deliv Rev, 2011, 63(14-15):1228-46.
Verma et al., "Effect of surface properties on nanoparticle-cell interactions," Small, 2010, 6(1):12-21.
Von Roemeling et al., "Breaking Down the Barriers to Precision Cancer Nanomedicine," Trends Biotechnol, Feb. 2017, 35(2):159-171.

(56) References Cited

OTHER PUBLICATIONS

Vonarbourg et al., "Evaluation of pegylated lipid nanocapsules versus complement system activation and macrophage uptake," J Biomed Mater Res A, 2006, 78(3):620-8.
Vrhovski et al., "Coacervation Characteristics of Recombinant Human Tropoelastin," European Journal of Biochemistry, 1997, 250(1):92-98.
Wang et al., "A Molecular Grammar Governing the Driving Forces for Phase Separation of Prion-like RNA Binding Proteins," Cell, Jul. 2018, 174(3):688-699.e616.
Wang et al., "More effective nanomedicines through particle design," Small, 2011, 7(14):1919-31.
Wang et al., "Nanoparticle delivery of cancer drugs," Annu Rev Med, 2012, 63:185-98.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface To Enhance Cancer Cell Targeting by Polymer Micelles," Nano Lett Oct. 2017, 17(10):5995-6005.
Wechsel et al., "Renal Cell Carcinoma: Immunohistological Investigation of Expression of the Integrin av3," Anticancer research, 1999, 19(2C):1529-1532.
Weis et al., "αV Integrins in Angiogenesis and Cancer," Cold Spring Harb Perspect Med, 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wilkins et al., "Hydrodynamic Radii of Native and Denatured Proteins Measured by Pulse Field Gradient NMR Techniques," Biochemistry, 1999, 38(50):16424-16431.
Wimley et al., "Experimentally determined hydrophobicity scale for proteins at membrane interfaces," Nature Structural & Molecular Biology, 1996, 3(10):842-848.
Wright et al., "Intrinsically disordered proteins in cellular signalling and regulation," Nat Rev Mol Cell Biol, Jan. 2015, 16(1):18-29.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, 2011, 155(2):248-61.
Xu et al., "Inorganic nanoparticles as carriers for efficient cellular delivery," Chemical Engineering Science, 2006, 61(3):1027-1040.
Zhao et al., "Cellular uptake, intracellular trafficking, and cytotoxicity of nanomaterials," Small, 2011, 7(10):1322-37.
Zhao et al., "Tumor αvβ3 Integrin Is a Therapeutic Target for Breast Cancer Bone Metastases," Cancer Res, 2007, 67(12):5821-30.
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
European Patent Office Extended Search Report for Application No. 17851568.0 dated Mar. 16, 2020 (9 pages).
Merriam Webster Dictionary, "Plurality," <https://www.merriam-webster.com/dictionary/plurality> webpage accessed Jun. 25, 2020.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
International Search Report and Written Opinion for Application No. PCT/US2019/061144 dated May 21, 2020 (15 pages).
United States Patent Office Action for U.S. Appl. No. 16/058,924 dated Jul. 6, 2020 (51 pages).
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Agarwal et al., "One-step microfluidic generation of pre-hatching embryo-like core-shell microcapsules for miniaturized 3D culture of pluripotent stem cells," Lab Chip, 2013, 13: 4525-4533.
Amiram et al., "Evolution of translation machinery in recoded bacteria enables multi-site incorporation of nonstandard amino acids," Nat Biotechnol, 2015, 33:1272-1279.
Appleyard et al., "Multiplexed protein quantification with barcoded hydrogel microparticles," Anal Chem, 2011, 83 193-199.
Bain et al., "Formation of monolayer films by the spontaneous assembly of organic thiols from solution onto gold," Journal of the American Chemical Society, 1989, 111: 321-335.
Boeynaems et al., "Spontaneous driving forces give rise to protein-RNA condensates with coexisting phases and complex material properties," Proc Natl Acad Sci USA, 2019, 116: 7889-7898.
Cha et al., "Microfluidics-assisted fabrication of gelatin-silica core-shell microgels for injectable tissue constructs," Biomacromolecules, 2014, 15: 283-290.
Chapin et al., "Rapid microRNA profiling on encoded gel microparticles," Angew Chem Int Ed Engl, 2011, 50: 2289-2293.
Chin et al., "Addition of p-azido-l-phenylalanine to the genetic code of *Escherichia coli*," Journal of the American Chemical Society, 2002, 124: 9026-9027.
Choi et al., "Multiplexed detection of mRNA using porosity-tuned hydrogel microparticles," Anal Chem, 2012, 84: 9370-9378.
Choi et al., "Recent advances in engineering microparticles and their nascent utilization in biomedical delivery and diagnostic applications," Lab Chip, 2017,17: 591-613.
Chu et al., "Controllable monodisperse multiple emulsions," Angew Chern Int Ed Engl, 2007,46: 8970-8974.
Costa et al., "Photo-crosslinkable unnatural amino acids enable facile synthesis of thermoresponsive nano- to microgels of intrinsically disordered polypeptides," Adv Mater, 2018, 30(5): 1704878.
Darling et al., "Viscoelastic properties of zonal articular chondrocytes measured by atomic force microscopy," Osteoarthritis Cartilage, 2006, 14: 571-579.
Griffin et al., "Accelerated wound healing by injectable microporous gel scaffolds assembled from annealed building blocks," Nat Mater, 2015, 14: 737-744.
Hutter et al., "Calibration of atomic-force microscope tips," Review of Scientific Instruments, 1993, 64:1868-1873.
Hwang et al., "Differentially degradable janus particles for coi ill oiled release applications," Macromol Rapid Commun, 2012, 33:1178-1183.
Jang et al., "Engineering Globular Protein Vesicles through Tunable Self-Assembly of Recombinant Fusion Proteins," Small, 2017, 13(36): 1700399.
Khademhosseini et al., "Micromolding of photocrosslinkable hyaluronic acid for cell encapsulation and enlrapment," J Biomed Mater Res A, 2006, 79: 522-532.
Kim et al., "Generation of core-shell microcapsules with three-dimensional focusing device for efficient formation of cell spheroid," Lab Chip, 2011, 11: 246-252.
Liu, L. et al., "Monodisperse core-shell chitosan microcapsules for pH-responsive burst release of hydrophobic drugs," Soft Matter, 2011, 7: 4821-4827.
Ma et al., "Core-shell hydrogel microcapsules for improved islets encapsulation," Adv Healthc Mater, 2013, 2: 667-672.
Matsunaga et al., "Molding cell beads for rapid construction of macroscopic 3D tissue architecture," Adv Mater, 2011, 23: H90-94.
Oh et al., "The development of microgels/nanogels for drug delivery applications," Progress in Polymer Science, 2008, 33(4): 448-477.
Panda et al., "Stop-flow lithography to generate cell-laden microgel particles," Lab Chip, 2008, 8:1056-1061.
Paulsen et al., "Optofluidic fabrication for 3D-shaped particles," Nat Commun, 2015, 6: 6976.
Roberts et al., "Injectable tissue integrating networks from recombinant polypeptides with tunable order," Nature Materials, 2018, 17(12): 1154-1163.
Rodriguez-Cabello et al., "Elastin-like polypeptides in drug delivery," Adv Drug Deliv Rev, 2016, 97: 85-100.
Song et al., "Budding-like division of all-aqueous emulsion droplets modulated by networks of protein nanofibrils," Nat Commun, 2018, 9: 2110.
Srinivas et al., "Aptamer-functionalized microgel particles for protein detection," Anal Chem, 2011, 83: 9138-9145.

(56) References Cited

OTHER PUBLICATIONS

Tsuda et al., "Monodisperse cell-encapsulating peptide microgel beads for 3D cell culture," Langmuir, 2010, 26: 2645-2649.
Utada et al., "Monodisperse double emulsions generated from a microcapillary device," Science, 2005, 308: 537-541.
Uversky, "Protein intrinsic disorder-based liquid-liquid phase transitions in biological systems: Complex coacervates and membrane-less organelles," Adv Colloid Interface Sci, 2017, 239: 97-114.
Volodkin et al., "One-Step Formulation of Protein Microparticles with Tailored Properties: Hard Templating at Soft Conditions," Advanced Functional Materials, 2012, 22:1914-1922.
Wang et al., "Functional polymeric microparticles engineered from collrollable microfluidic emulsions," Acc Chem Res, 2014, 47: 373-384.
Yeh et al., "Micromolding of shape-conkrolled, harvestable cell-laden hydrogels," Biomaterials, 2006, 27: 5391-5398.
United States Patent Office Action for U.S. Appl. No. 16/305,696 dated Jan. 28, 2021 (15 pages).
United States Patent Office Notice of Allowance for U.S. Appl. No. 16/332,865 dated Apr. 2, 2021 (10 pages).
Brazilian Patent Office Action for Application No. 112018002342-6 dated Jan. 19, 2021 (7 pages, English translation included).
Chinese Patent Office Action for Application No. 201680058249.5 dated Jan. 5, 2021 (13 pages, English translation included).
Resh, "Covalent Lipid Modifications of Proteins," Curr Biol., May 2013, 23(10): R431-R435.
United States Patent Office Action for U.S. Appl. No. 16/477,229 dated Apr. 12, 2021 (14 pages).
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
Japanese Patent Office Action for Application No. 2018-506150 dated Jul. 27, 2020 (7 pages, English translation ncluded).
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
Indian Patent Office Examination Report for Application No. 201837005279 dated Oct. 1, 2021 (6 pages).
Nikolic et al., "Structural basis for the recognition of LDL-receptor family members by VSV glycoprotein," Nature Communications, 2018, 9:1029, 12 pages.
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
Alghoul et al., "The effect of hyaluronan hydrogel on fat graft survival," Aesthet Surg J, 2012, 32: 622-633.
American Society of Plastic Surgeons, "2017 Plastic Surgery Statistics Report," Oct. 2018, 25 pages.
Balaji, "Subdermal fat grafting for Parry-Romberg syndrome," Ann Maxillofac Surg, 2014, 4: 55-59.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Bennett et al., "Association of Fat Grafting With Patient-Reported Outcomes in Postmastectomy Breast Reconstruction," JAMA Surg, 2017, 152: 944-950.
Brzezienski et al., "Autologous Fat Grafting to the Breast Using REVOLVE System to Reduce Clinical Costs," Ann Plast Surg, 2016, 77: 286-289.
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
Eom et al., "The No. of operations required for completing breast reconstruction," Plast Reconstr Surg Glob Open, 2012, 2: e242.
Gabriel et al., "Fat grafting and breast reconstruction: tips for ensuring predictability," Gland Surg, 2015, 4:232-243.
Gylbert, "Applanation tonometry for the evaluation of breast compressibility," Scand J Plast Reconstr Surg Hand Surg, 1989, 23: 223-229.
Hess et al., "Graphene Transistors for Multifunctional Polymer Brushes for Biosensing Applications," Applied Materials & Interfaces, 2014, 6: 9705-9710.
Hsu et al., "Fat grafting's past, present, and future: why adipose tissue is emerging as a critical link to the advancement of regenerative medicine," Aesthet Surg J, 2015, 32: 892-899.
Hwang et al., "Synthesis and Characterization of Polystyrene Brushes for Organic Thin Film Transistors," Journal of Nanoscience and Nanotechnology, 2012, 12: 4137-4141.
Kronowitz et al., "Delayed-Immediate Breast Reconstruction," Plastic and Reconstructive Surgery, 2004, 113: 1617-1628.
Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Pan et al., "A Pig Model for the Histological Analysis of Adipocytes after Co—injections of Autologous Fat with Fillers," International Journal of Surgery & Surgical Techniques, 2016, 2: 7 pages.
Park et al., "Polymer Brush As a Facile Dielectric Surface Treatment for High-Performance, Stable, Soluble Acene-Based Transistors," Chemistry of Materials, 2010, 22: 5377-5382.
Rasmussen et al., "A Novel Porcine Model for Future Studies of Cell-enriched Fat Grafting," Plast Reconstr Surg Glob Open, 2018, 6: e1735.
Roca et al., "Autologous Fat Grafting for Treatment of Breast Implant Capsular Contracture: A Study in Pigs," Aesthet Surg J, 2014, 34: 769-775.
Sandberg et al., "The Structure of the Elastic Fiber: An Overview," The Journal of Investigative Dermatology, 1982, 79(S1): 128s-132s.
Simonacci et al., "Procedure, applications, and outcomes of autologous fat grafting," Ann Med Surg(Lond), 2017, 20: 49-60.
Strong et al., "The Current State of Fat Grafting: A Review of Harvesting, Processing, and Injection Techniques," Plast Reconstr Surg, 2015, 136: 897-912.
Tamburro et al., "Fractal aspects of elastin supramolecular organization," J Biomol Struct Dyn, 1995, 12: 1161-1172.
Toshima et al., "Three-dimensional architecture of elastin and collagen fiber networks in the human and rat lung," Arch Histol Cytol, 2004, 67: 31-40.
UniProtKB—P15214 (GST_PROMI) acessed online at <https://www.uniprot.org/uniprot/P152146/> on Jun. 8, 2021, 7 pages.
Wang et al., "Pigs Can Be Used as a Large Animal Model for Autologous Fat Grafting," Ophthalmic Plast Reconstr Surg, 2016, 32: 73-74.
Wu et al., "An injectable adipose matrix for soft-tissue reconstruction," Plast Reconstr Surg, 2012, 129: 1247-1257.
Chinese Patent Office Action for Application No. 201680058249.5 dated May 24, 2021 (4 pages, statement of relevance included).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.
Amanat et al., "A serological assay to detect SARS-CoV-2 seroconversion in humans," Nat Med, 2020, 26(7): 1033-1036.
American Hospital Association, "AHA Hospital Statistics," 2020 edition. Available at: <https://www.aha.org/statistics/fast-facts-us-hospitals>.
Armbruster et al., "Limit of blank, limit of detection and limit of quantitation," Clin Biochem Rev, 2008, 29 Suppl 1: S49-52.

(56) References Cited

OTHER PUBLICATIONS

Arshavsky-Graham et al., "Lab-on-a-Chip Devices for Point-of-Care Medical Diagnostics," Advances in Biochemical Engineering/Biotechnology, 2020, 19 pages.

Atyeo et al., "Distinct Early Serological Signatures Track with SARS-CoV-2 Survival," Immunity, 2020, 53: 524-532.

Baraf et al., "Infusion-related reactions with pegloticase, a recombinant uricase for the treatment of chronic gout refractory to conventional therapy," J Clin Rheumatol, 2014, 20: 427-432.

Benn et al., "Physiology of Hyperuricemia and Urate-Lowering Treatments," Front Med (Lausanne), 2018, 5: 160, 28 pages.

Berry et al., "Development and characterisation of neutralising monoclonal antibody to the SARS-coronavirus," J Virol Methods, 2004, 120: 87-96.

Bryant et al., "Serology for SARS-CoV-2: Apprehensions, opportunities, and the path forward," Sci Immunol, 2020, 5: eabc6347, 4 pages.

Calabrese et al., "Frequency, distribution and immunologic nature of infusion reactions in subjects receiving pegloticase for chronic refractory gout," Arthritis Res Ther, 2017, 19: 191, 7 pages.

Caves et al., "Thermal inactivation of uricase (urate oxidase): mechanism and effects of additives," Biochemistry, 2013, 52: 497-507.

Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.

Chan et al., "A randomized, repeat-dose, pharmacodynamic and safety study of an antidote-controlled factor IXa inhibitor," J Thromb Haemost, 2008, 6(5): 789-796.

Chan et al., "Phase 1b randomized study of antidote-controlled modulation of factor IXa activity in patients with stable coronary artery disease," Circulation, 2008, 117(22): 2865-2874.

Chappell et al., "Computational design of small transcription activating RNAs for versatile and dynamic gene regulation," Nat Commun, 2017, 8(1): 1051.

Chappell et al., "Creating small transcription activating RNAs," Nat Chem Biol, 2015, 11(3): 214-220.

Chase et al., "Single-Stranded DNA Binding Proteins Required for DNA Replication," Ann. Rev. Biochem., 1986, 55: 103-136.

Chen et al., "Real-world patterns of pegloticase use for treatment of gout: descriptive multidatabase cohort study," BMJ Open, 2020, 10: e041167, 6 pages.

Chen et al., "The influence of polymer topology on pharmacokinetics: differences between cyclic and linear PEGylated poly(acrylic acid) comb polymers," J Control Release, 2009, 140: 203-209.

Chu et al., "Molecular Diagnosis of a Novel Coronavirus (2019-nCoV) Causing an Outbreak of Pneumonia," Clin Chem, 2020, 66(4): 549-555.

Cohen et al., "First clinical application of an actively reversible direct factor IXa inhibitor as an anticoagulation strategy in patients undergoing percutaneous coronary intervention," Circulation, 2010, 122(6): 614-622.

Cong et al., "Nucleocapsid Protein Recruitment to Replication-Transcription Complexes Plays a Crucial Role in Coronaviral Life Cycle," J Virol, 2020, 94: e01925-19, 21 pages.

Crowther, "The ELISA guidebook," Methods Mol Biol, 2000, 149(III-IV): 1-413.

Dale et al., "Direct covalent mercuration of nucleotides and polynucleotides," Biochemistry, 1975, 14(11): 2447-2457.

Davis et al., "Antibodies and the RNA World: A Role for Low-molecular-weight Effectors in Biochemical Evolution," RNA World, 1993, Chapters, p. 185-204.

Dincer et al., "Multiplexed Point-of-Care Testing—xPOCT," Trends Biotechnol, 2017, 35(8): 728-742.

Dong et al., "An interactive web-based dashboard to track COVID-19 in realtime," Lancet Infect Dis, 2020, 20: 533-534.

Dutta et al., "The Nucleocapsid Protein of SARS-CoV-2: a Target for Vaccine Development," J Virol, 2020, 94(13): e00647-20, 2 pages.

Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.

Eichhorn et al., "Interactions of metal ions with polynucleotides and related compounds. XII. The relative effect of various metal ions on DNA helicity," J. Am. Chem. Soc, 1968, 90: 7323-7328.

Ekladious et al., "Polymer-drug conjugate therapeutics: advances, insights and prospects," Nature Reviews Drug Discovery, 2019, 18: 273-294.

Fathallah et al., "Immunogenicity of Subcutaneously Administered Therapeutic Proteins—a Mechanistic Perspective," The AAPS Journal, 2013, 15(4): 897-900.

Fox et al., "Soluble polymer carriers for the treatment of cancer: the importance of molecular architecture," Acc Chem Res, 2009, 42(8): 1141-1151.

Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.

Garay et al., "Therapeutic perspectives on uricases for gout," Joint Bone Spine, 2012, 79: 237-242.

Gold et al., "Aptamers and the RNA World, Past and Present," Cold Spring Harbor Perspect. Biol., 2012, 4: a003582, 9 pages.

Harris et al., "Effect of pegylation on pharmaceuticals," Nature Reviews Drug Discovery, 2003, 2: 214-221.

Heggestad et al., "In Pursuit of Zero 2.0: Recent Developments in Nonfouling Polymer Brushes for Immunoassays," Adv Mater, 2020, 32: e1903285.

Hermanson et al., "Peginesatide for the treatment of anemia due to chronic kidney disease—an unfulfilled promise," Expert Opin Drug Saf, 2016, 15(10): 1421-1426.

Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.

Heus, "RNA aptamers," Nat Struct Biol, 1997, 4(8): 597-600.

Huang et al., "Clinical features of patients infected with 2019 novel coronavirus in Wuhan," China. Lancet, 2020, 395: 497-506.

Hucknall et al., "Simple Fabrication of Antibody Microarrays on Nonfouling Polymer Brushes with Femtomolar Sensitivity for Protein Analytes in Serum and Blood," Adv Mater, 2009, 21(19): 1968-1971.

Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.

Hwang et al., "Inhibition of gene expression in human cells through small molecule-RNA interactions," Proc. Natl. Acad. Sci. USA, 1999, 96(23): 12997-13002.

Jiang et al., "Neutralizing Antibodies against SARS-CoV-2 and Other Human Coronaviruses," Trends Immunol, 2020, 41(5): 355-359.

Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.

Joh et al., "Inkjet-printed point-of-care immunoassay on a nanoscale polymer brush enables subpicomolar detection of analytes in blood," Proc Natl Acad Sci U S A, 2017, 114: E7054-E7062.

Kang et al., "Crystal structure of SARS-CoV-2 nucleocapsid protein RNA binding domain reveals potential unique drug targeting sites," Acta Pharm Sin B, 2020, 10(7): 1228-1238.

Keefe et al., "Aptamers as therapeutics," Nature Reviews Drug Discovery, 2010, 9: 537-550.

Khailany et al., "Genomic characterization of a novel SARS-CoV-2," Gene Rep, 2020, 9: 100682, 6 pages.

Korte et al., "Short activated partial thromboplastin times are related to increased thrombin generation and an increased risk for thromboembolism," Am J Clin Pathol, 2000, 113(1): 123-127.

Kozel et al., "Point-of-care testing for infectious diseases: past, present, and future," J Clin Microbiol, 2017, 55: 2313-2320.

(56) References Cited

OTHER PUBLICATIONS

Kozma et al., "Anti-PEG antibodies: Properties, formation, testing and role in adverse immune reactions to PEGylated nano-biopharmaceuticals," Adv Drug Deliv Rev, 2020, 154-155, 163-175.
Krammer et al., "Serology assays to manage COVID-19," Science, 2020, 368: 1060-1061.
Kuo et al., "Global epidemiology of gout: prevalence, incidence and risk factors," Nature Reviews Rheumatology, 2015, 11: 649-662.
Laing et al., "A dynamic COVID-19 immune signature includes associations with poor prognosis," Nat Med, 2020, 26:1623-1635.
Li et al., "Ferric Chloride-induced Murine Thrombosis Models," J. Vis. Exp., 2016, 115: e54479, 12 pages.
Lieberman et al., "Comparison of Commercially Available and Laboratory-Developed Assays for In Vitro Detection of SARS-CoV-2 in Clinical Laboratories," J Clin Microbiol, 2020, 58(8):e00821-20.
Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.
Lippard et al., "Platinum complexes: probes of polynucleotide structure and antitumor drugs," Acc. Chem. Res., 1978, 11(5): 211-217.
Lipsitch et al., "Antibody testing will enhance the power and accuracy of COVID-19-prevention trials," Nat Med, 2020, 26: 818-819.
Lipsky et al., "Pegloticase immunogenicity: the relationship between efficacy and antibody development in patients treated for refractory chronic gout," Arthritis Res Ther, 2014, 16: R60.
Lisboa Bastos et al., "Diagnostic accuracy of serological tests for covid-19: systematic review and meta-analysis," BMJ, 2020, 370: m2516.
Liu et al., "High neutralizing antibody titer in intensive care unit patients with COVID-19," Emerg Microbes Infect, 2020, 9: 1664-1670.
Liu et al., "Semi-permeable coatings fabricated from comb-polymers efficiently protect proteins in vivo," Nature Communications, 2014, 5: 5526.
Liu et al., "The experiences of health-care providers during the COVID-19 crisis in China: a qualitative study," Lancet Glob Health, 2020, 8: e790-e798.
Lu et al., "Genomic characterisation and epidemiology of 2019 novel coronavirus: implications for virus origins and receptor binding," Lancet, 2020, 395: 565-574.
Maier et al., "From selection hits to clinical leads: progress in aptamer discovery," Mol. Ther. Methods Clin. Dev., 2016, 3: 16014, 10 pages.
McAndrews et al., "Heterogeneous antibodies against SARS-CoV-2 spike receptor binding domain and nucleocapsid with implications for COVID-19 immunity," JCI Insight, 2020, 5(18):e142386, 14 pages.
McElvaney et al., "A linear prognostic score based on the ratio of interleukin-6 to interleukin-10 predicts outcomes in COVID-19," EBioMedicine, 2020, 61: 103026, 8 pages.
McManus et al., "Gene silencing in mammals by small interfering RNAs," Nat Rev Genet, 2002, 3(10): 737-747.
Mejia-Salazar et al., "Microfluidic Point-of-Care Devices: New Trends and Future Prospects for eHealth Diagnostics," Sensors, 2020, 20: 1951, 19 pages.
Miller et al., "Disease and healthcare burden of COVID-19 in the United States," Nat Med, 2020, 26: 1212-1217.
Moreno et al., "Anti-PEG Antibodies Inhibit the Anticoagulant Activity of PEGylated Aptamers," Cell Chem Biol, 2019, 26(5): 634-644.e3.
Nalla et al., "Comparative Performance of SARS-CoV-2 Detection Assays Using Seven Different Primer-Probe Sets and One Assay Kit," J Clin Microbiol, 2020, 58: e00557-20, 6 pages.
Nimjee et al., "Aptamers as Therapeutics," Annu Rev Pharmacol Toxicol, 2017, 57: 61-79.
Norman et al., "Ultrasensitive high-resolution profiling of early seroconversion in patients with COVID-19," Nat Biomed Eng, 2020, 11 pages.
Nunn et al., "Crystal Structure of Tobacco Etch Virus Protease Shows the Protein C Terminus Bound within the Active Site," Journal of Molecular Biology, 2005, 350: 145-155.
Nyborg et al., "A Therapeutic Uricase with Reduced Immunogenicity Risk and Improved Development Properties," PLoS One, 2016, 11(12): e0167935, 23 pages.
Okba et al., "Severe Acute Respiratory Syndrome Coronavirus 2-Specific Antibody Responses in Coronavirus Disease Patients," Emerg Infect Dis, 2020, 26: 1478-1488.
Ozer et al., "Effect of Molecular Architecture on Cell Interactions and Stealth Properties of PEG," Biomacromolecules, 2017, 18: 2699-2710.
Pecoraro et al., "A systematic evaluation of immunoassay point-of-care testing to define impact on patients' outcomes," Ann Clin Biochem, 2017, 54(4): 420-431.
Pisal et al., "Delivery of therapeutic proteins," Journal of Pharmaceutical Sciences, 2010, 99(6): 2557-2575.
Ponti et al., "Biomarkers associated with COVID-19 disease progression," Crit Rev Clin Lab Sci, 2020, 57, 11 pages.
Posthuma-Trumpie et al., "Lateral flow (immuno)assay: its strengths, weaknesses, opportunities and threats. A literature survey," Anal Bioanal Chem, 2009, 393: 569-582.
Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.
Ravichandran et al., "Antibody signature induced by SARS-CoV-2 spike protein immunogens in rabbits," Sci Transl Med, 2020, 10.1126/scitranslmed.abc3539, 9 pages.
Richter et al., "Mechanistic determinants of biotherapeutics absorption following SC administration," AAPS J, 2012, 14(3): 559-570.
Rinaldi et al., "Antisense oligonucleotides: the next frontier for treatment of neurological disorders," Nat Rev Neurol, 2018, 14(1): 9-21.
Rogers et al., "Isolation of potent SARS-CoV-2 neutralizing antibodies and protection from disease in a small animal model," Science, 2020, 369: 956-963.
Rosadas et al., "Testing for responses to the wrong SARS-CoV-2 antigen," Lancet, 2020, 396: e23.
Rothe et al., "Transmission of 2019-nCoV Infection from an Asymptomatic Contact in Germany," N Engl J Med, 2020, 382: 10, 2 pages.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor Ixa," Nature, 2002, 19(6902): 90-94.
Seow et al., "Longitudinal evaluation and decline of antibody responses in SARS-CoV-2 infection," medRxiv, 2020, 24 pages.
Shu et al., "GISAID: Global initiative on sharing all influenza data—from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Sundy et al., "Efficacy and tolerability of pegloticase for the treatment of chronic gout in patients refractory to conventional treatment: two randomized controlled trials," Jama, 2011, 306(7): 711-720.

(56) References Cited

OTHER PUBLICATIONS

Sundy et al., "Pharmacokinetics and pharmacodynamics of intravenous PEGylated recombinant mammalian urate oxidase in patients with refractory gout," Arthritis Rheum, 2007, 56(3): 1021-1028.
Tang et al., "Laboratory Diagnosis of COVID-19: Current Issues and Challenges," J Clin Microbiol, 2020, 58: e00512-20, 9 pages.
Tuerk et al., "Systematic evolution of ligands by exponential enrichment: RNA ligands to bacteriophage T4 DNA polymerase," Science, 1990, 249(4968): 505-510.
Turner et al., "Challenges and Opportunities for the Subcutaneous Delivery of Therapeutic Proteins," Journal of Pharmaceutical Sciences, 2018, 107(5): 1247-1260.
U.S. FDA—Classify your medical devices. Updated as of: Feb. 7, 2020. Available at: <https://www.fda.gov/medical-devices/overview-device-regulation/classify-your-medical-device>.
U.S. FDA—In Vitro Diagnostics. Updated as of: Oct. 25, 2019. Available at: <https://www.fda.gov/medical-devices/products-and-medical-procedures/vitro-diagnostics>.
Vaninov, "In the eye of the COVID-19 cytokine storm," Nat Rev Immunol, 2020, 20: 277, 1 page.
Vashist et al., "Emerging Technologies for Next-Generation Point-of-Care Testing," Trends Biotechnol, 2015, 33(11): 692-705.
Verhoef et al., "Potential induction of anti-PEG antibodies and complement activation toward PEGylated therapeutics," Drug Discov Today, 2014, 19(12): 1945-1952.
Vugmeyster et al., "Pharmacokinetics and toxicology of therapeutic proteins: Advances and challenges," World J Biol Chem, 2012, 3(4): 73-92.
Waterboer et al., "Suppression of non-specific binding in serological Luminex assays," J Immunol Methods, 2006, 309: 200-204.
Weinhandl et al., "Relative safety of peginesatide and epoetin alfa," Pharmacoepidemiology and Drug Safety, 2014, 23(10): 1003-1011.
Werstuck et al., "Controlling gene expression in living cells through small molecule-RNA interactions," Science, 1998, 282(5387): 296-298.
Whitman et al., "Evaluation of SARS-CoV-2 serology assays reveals a range of test performance," Nat Biotechnol, 2020, 38: 1174-1183.
Wiersinga et al., "Pathophysiology, Transmission, Diagnosis, and Treatment of Coronavirus Disease 2019 (COVID-19): A Review," JAMA, 2020, 324(8): 782-793.
Winter et al., "The important role of serology for COVID-19 control," Lancet Infect Dis, 2020, 20: 758-759.
Wölfel et al., "Virological assessment of hospitalized patients with COVID-2019," Nature, 2020, 581:465-469.
Woodruff et al., "Modulation of the Coagulation Cascade Using Aptamers," Arterioscler Thromb Vasc Biol, 2015, 35(10): 2083-2091.
Yamaoka et al., "Distribution and tissue uptake of poly(ethylene glycol) with different molecular weights after intravenous administration to mice," Journal of Pharmaceutical Sciences, 1994, 83(4): 601-606.
Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Plasma IP-10 and MCP-3 levels are highly associated with disease severity and predict the progression of COVID-19," J Allergy Clin Immunol, 2020, 146: 119-127.
Yang et al., "Uricases as therapeutic agents to treat refractory gout: Current states and future directions," Drug Dev Res, 2012, 73(2): 66-72.
Yong et al., "Connecting clusters of COVID-19: an epidemiological and serological investigation," Lancet Infect Dis, 2020, 20: 809-815.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," PLoS ONE, 2012, 7(6): e39659.
Zhao et al., "Antibody responses to SARS-CoV-2 in patients of novel coronavirus disease 2019," Clin Infect Dis, 2020, 22 pages.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
International Search Report and Written Opinion for Application No. PCT/US2021/020591 dated Oct. 7, 2021 (14 pages).
International Search Report and Written Opinion for Application No. PCT/US2021/046833 dated Nov. 8, 2021 (13 pages).
International Search Report and Written Opinion for Application No. PCT/US2021/035823 dated Dec. 8, 2021 (16 pages).
Australian Patent Office Examination Report No. 1 for Application No. 2016301391 dated Nov. 5, 2021 (3 pages).
United States Patent Office Action for U.S. Appl. No. 16/614,282 dated Oct. 21, 2021 (14 pages).
United States Patent Office Action for U.S. Appl. No. 16/477,229 dated Oct. 26, 2021 (10 pages).
United States Patent Office Action for U.S. Appl. No. 17/265,165 dated Dec. 21, 2021 (11 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
United States Patent Office Action for U.S. Appl. No. 16/927,982 dated Jan. 6, 2022 (6 pages).
United States Patent Office Action for U.S. Appl. No. 16/477,229 dated Mar. 3, 2022 (10 pages).
Ren et al., "Stimulus-Responsive Polymer Prodrugs," Progress in Chemistry, 2013, 25(5): 10 pages.
United States Patent Office Action for U.S. Appl. No. 16/614,282 dated Apr. 27, 2022 (15 pages).
United States Patent Office Notice of Allowance for U.S. Appl. No. 16/305,696 dated May 23, 2022 (10 pages).
United States Patent Office Notice of Allowance for U.S. Appl. No. 16/305,696 dated Jun. 10, 2022 (4 pages).
United States Patent Office Action for U.S. Appl. No. 16/477,229 dated Jun. 13, 2022 (11 pages).
Da Pieve Chiara et al., "Modification of Thiol Functionalized Aptamers by Conjugation of Synthetic Polymers," Bioconjugate Chemistry, 2009, 1(1): 169-174.
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).

\* cited by examiner

| Possible Sequences $(VPX_1X_2G)_n$ | |
|---|---|
| VPKEG | VPKDG |
| VPREG | VPRDG |

FIG. 1D

ABP-Albumin Binding Peptide

I.V. PK Study

➢ Experimental Design:
- VPGAG-120 (no of repeats control) ⎤ ELP
- VPGAG-160 (MW control) ⎦
- VPKEG-120 ⎤
- VPREG-120 ⎥ ZIPP
- VPKDG-120 ⎥
- VPRDG-120 ⎦

- ➢ Experimental Design:
  - VPGAG-120 (no of repeats control)
  - VPGAG-160 (MW control)
  - VPKEG-120
  - VPKDG-120

GENETICALLY ENCODED INTRINSICALLY DISORDERED STEALTH POLYMERS FOR DELIVERY AND METHODS OF USING SAME

CROSS-REFERENCE TO RELATED APPLICATIONS

The present patent application is a national stage filing under 35 U.S.C. § 371 of International Application No. PCT/US2016/045655, filed on Aug. 4, 2016, which claims the benefit of U.S. Provisional Application No. 62/200,726, filed Aug. 4, 2015, the content of which are incorporated herein by reference in their entirety.

STATEMENT REGARDING FEDERALLY SPONSORED RESEARCH

This invention was made with government support under grant 5R01EB000188 R01 awarded by the National Institutes of Health. The government has certain rights in the invention.

SEQUENCE LISTING

The instant application includes a Sequence Listing which has been submitted electronically in ASCII format and is hereby incorporated by reference in its entirety. Said ASCII copy, created on Sep. 12, 2016, is named 028193-9241-WO00_As_Filed_Sequence_Listing.txt and is 4,470 bytes in size.

FIELD

The disclosure relates to methods of drug delivery and, more particularly, to zwitterionic polypeptides conjugated to therapeutics. The conjugates have improved biocompatibility and biodegradability. In some embodiments, the conjugates may be recombinantly expressed, and thereby able to be designed with precision and manipulated at the gene level.

INTRODUCTION

Delivery of drugs or therapeutics such as small molecules, peptides, and proteins, in their native form, is limited by their poor stability, low solubility, and short in vivo circulation. These challenges in drug delivery lead to decreased therapeutic efficacy and increased risk of off-target toxicity. Attaching macromolecular carriers to drugs can improve their solubility, plasma half-life, tumor-specific uptake, and their overall therapeutic potential. Various materials, mostly synthetic polymers, have been previously designed to deliver drugs. One such synthetic polymer is polyethylene glycol (PEG). PEG is a hydrophilic and hygroscopic polymer that forms a "water cage" around the drug, which then provides steric repulsion from blood components and prevents both its opsonization and enzymatic degradation. This "stealth" property of PEG improves solubility and stability of drugs, and reduces their premature clearance from the subject, making PEGylation—the process of attaching drugs to PEG—an important method in the pharmaceutical industry. In recent years, a new class of zwitterionic synthetic polymers, polymers with alternating cationic and anionic groups in their monomer, has demonstrated similar stealth properties. There are, however, three major shortcomings that undermine the reliability of synthetic polymers as drug delivery vehicles. First, it is well documented that repeated exposure to PEG can produce PEG-specific antibodies that trigger adverse immune responses. Second, synthetic polymers are non-biodegradable, and their effect in vivo post drug delivery is not well understood. Third, synthetic polymers are polydisperse in that each batch is composed of chains with different molecular weights. This polydispersity, which is intrinsic in synthetic polymers, can lead to a population of drug conjugates with different biological properties, especially with respect to the half-life and immunogenicity. There is a need in the art for efficient delivery of drugs with improved biocompatibility, solubility, stability and half-life, and reduced toxicity.

SUMMARY

In one aspect, provided herein are conjugates comprising: (a) a polypeptide comprising one or more charged motifs, each charged motif independently having an amino acid sequence consisting of SEQ ID NO: 1 (VPX$_1$X$_2$G), wherein X$_1$ is a negatively or positively charged amino acid, and wherein X$_2$ is the other of a negatively or positively charged amino acid; and (b) one or more drug molecules attached to the polypeptide.

In some embodiments, the polypeptide includes a plurality of charged motifs. In some embodiments, the plurality of charged motifs is repeated in tandem. In some embodiments, the polypeptide further includes one or more uncharged motifs, each uncharged motif independently having an amino acid sequence consisting of SEQ ID NO: 3 (VPGXG), wherein X is any amino acid except proline. In some embodiments, the polypeptide includes a plurality of uncharged motifs. In some embodiments, the plurality of uncharged motifs is repeated in tandem. In some embodiments, one or more uncharged motifs are positioned between at least two adjacent charged motifs of the polypeptide.

In some embodiments, the polypeptide includes the amino acid sequence of SEQ ID NO: 2 (VPX$_1$X$_2$G)$_n$, wherein X$_1$ is a negatively or positively charged amino acid, X$_2$ is the other of a negatively or positively charged amino acid, and n is an integer greater than or equal to 1. In some embodiments, the polypeptide includes the amino acid sequence of SEQ ID NO: 4 (VPGXG)$_n$, wherein X is any amino acid except proline, and n is an integer greater than or equal to 1. In some embodiments, the polypeptide includes the amino acid sequence of SEQ ID NO: 5 (VPX$_1$X$_2$G)$_n$(VPGXG)$_m$, wherein X$_1$ is a negatively or positively charged amino acid, X$_2$ is the other of a negatively or positively charged amino acid, X is any amino acid except proline, and n and m are independently an integer greater than or equal to 1. In some embodiments, the polypeptide includes the amino acid sequence of SEQ ID NO: 6 (VPGXG)$_m$(VPX$_1$X$_2$G)$_n$, wherein X$_1$ is a negatively or positively charged amino acid, X$_2$ is the other of a negatively or positively charged amino acid, X is any amino acid except proline, and n and m are independently an integer greater than or equal to 1. In some embodiments, the polypeptide includes the amino acid sequence of SEQ ID NO: 7 {(VPX$_1$X$_2$G)(VPGXG)}$_b$, wherein X$_1$ is a negatively or positively charged amino acid, X$_2$ is the other of a negatively or positively charged amino acid, X is any amino acid except proline, and b is an integer greater than or equal to 1. In some embodiments, X$_1$ is a negatively charged amino acid, and wherein X$_2$ is a positively charged amino acid. In some embodiments, X$_1$ is a positively charged amino acid, and wherein X$_2$ is a negatively charged amino acid. In some embodiments, the negatively charged amino acid is independently selected from glutamatic acid and aspartic acid. In some embodiments, the positively charged amino acid is independently selected from lysine and arginine. In some embodiments, X is any amino acid except proline. In some embodiments, X is selected from arginine, histidine, lysine, aspartic acid, glutamic acid, serine, threonine, asparagine, glutamine, cysteine, selenocysteine, glycine, alanine, valine, leucine, isoleucine, methionine, phenylalanine, tyrosine, and tryptophan. In some embodiments, X is selected from glycine and valine.

In some embodiments, the polypeptide further includes a linker. In some embodiments, the linker includes one or more cysteines. In some embodiments, the linker includes an amino acid sequence selected from SEQ ID NO: (GGC), SEQ ID NO: $((GGC)_8)$, SEQ ID NO: $((G_4S)_3)$, and SEQ ID NO: $((VPGXG)_{16}$ wherein X is valine or cysteine present in a ratio of 1:1). In some embodiments, the linker is positioned at the C-terminus, at the N-terminus, or a both C- and N-termini of the polypeptide. In some embodiments, the one or more drug molecules are attached to the polypeptide via the linker. In some embodiments, the drug molecule is attached to the polypeptide through a thiol reactive group in the linker. In some embodiments, the one or more drug molecules are selected from a small molecule, nucleotide, polynucleotide, peptide, protein, carbohydrate, and a combination thereof. In some embodiments, the drug molecule includes a small molecule. In some embodiments, the drug molecule includes a protein. In some embodiments, the drug molecule includes a cancer therapeutic. In some embodiments, the drug molecule includes an antibody. In some embodiments, the drug molecule includes a paclitaxel. In some embodiments, the drug molecule includes Tn3 (TRAIL superagonist). In some embodiments, the conjugate is prepared for administration to a subject. In some embodiments, the polypeptide of the conjugate is recombinantly expressed. In some embodiments, the conjugate is recombinantly expressed.

In another aspect, provided herein are compositions comprising the conjugate as detailed herein.

In another aspect, provided herein are polynucleotides encoding the polypeptide as detailed herein. In another aspect, provided herein are polynucleotides encoding the conjugate as detailed herein. In another aspect, provided herein are vectors comprising the polynucleotide.

In another aspect, provided herein are methods of delivering a drug molecule to a subject, the method comprising administering the conjugate as detailed herein to the subject.

In another aspect, provided herein are methods of treating a subject having a disease or disorder, the method comprising administering the conjugate as detailed herein to the subject.

In another aspect, provided herein are methods of determining the presence of a target in a sample, the method comprising: contacting the sample with the conjugate as detailed herein under conditions to allow a complex to form between the drug molecule and the target in the sample; and detecting the presence of the complex, wherein presence of the complex is indicative of the target in the sample.

In some embodiments, the sample is obtained from a subject and the method further includes diagnosing a disease, prognosticating, or assessing the efficacy of a treatment of the subject. In some embodiments, when the method further includes assessing the efficacy of a treatment of the subject, then the method further includes modifying the treatment of the subject as needed to improve efficacy. In another aspect, provided herein are methods of diagnosing a disease in a subject, the method comprising: contacting a sample from the subject with the conjugate as detailed herein under conditions to allow a complex to form between the drug molecule and a target in the sample; determining the level of the target in the sample, wherein level of the complex is indicative of the level of the target in the sample; and comparing the level of the target in the sample to a control level of the target, wherein a level of the target different from the control level indicates disease in the subject. In some embodiments, the control level corresponds to the level in the subject at a time point before or during the period when the subject has begun treatment, and wherein the sample is taken from the subject at a later time point. In some embodiments, the sample is taken from the subject at a time point during the period when the subject is undergoing treatment, and wherein the control level corresponds to a disease-free level or to the level at a time point before the period when the subject has begun treatment. In some embodiments, the method further includes modifying the treatment or administering a different treatment to the subject when the treatment is determined to be ineffective in treating the disease. In some embodiments, the conjugate is labeled with a reporter. In some embodiments, the conjugate is administered to the subject intravenously, intraarterially, intraperitoneally, or intratumorally. In some embodiments, the conjugate has reduced antigenicity relative to the drug molecule conjugated to polyethylene glycol (PEG). In some embodiments, the conjugate has reduced immunogenicity relative to the drug molecule conjugated to polyethylene glycol (PEG). In some embodiments, the disease is selected from cancer, metabolic disease, autoimmune disease, cardiovascular disease, and orthopedic disorder. In some embodiments, the disease includes cancer. In some embodiments, the cancer is selected from breast cancer, colorectal cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. In some embodiments, the cancer includes breast cancer.

DETAILED DESCRIPTION

Figure 1A:
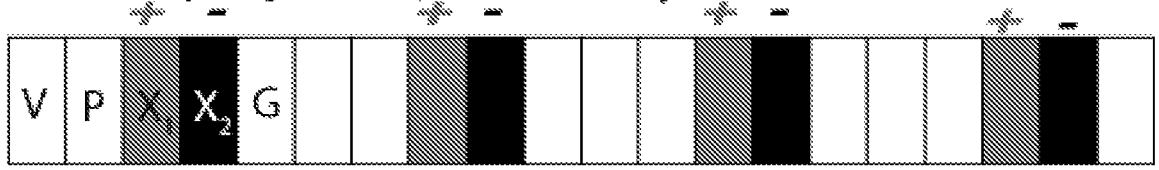
FIG. 1 shows possible architectures and sequences of ZiPPs. (A) Homopolymer. (B) Diblock polymer. (C) Multiblock polymer. (D) Possible sequences of the charged motif.
Figure 1B:
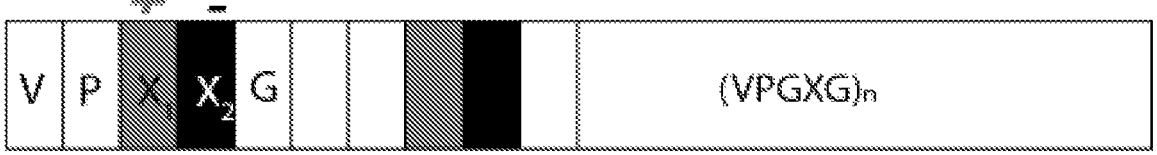
Figure 1C:
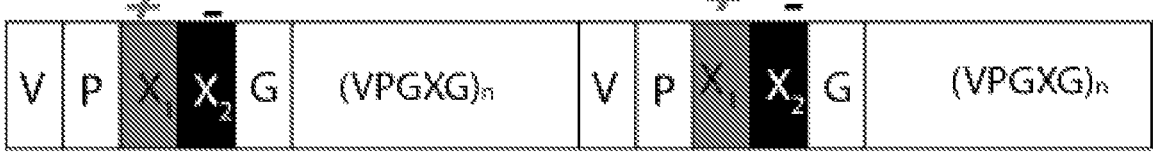

Provided herein are compositions and methods for delivering drug molecules to a subject. The compositions and methods include a conjugate including a polypeptide and a drug molecule attached thereto. The polypeptide includes both positively and negatively charged amino acids. The compositions and methods detailed herein may overcome previous challenges in drug delivery including limitations on biocompatibility, solubility, stability and half-life, immunogenicity, and antigenicity. The constructs detailed herein may use a hydrophilicity principle to provide a "water cage" around the conjugate to sterically shield the conjugate from degradation. The conjugates thereby increase the stability and solubility of the conjugated therapeutics and improve their in vivo efficacy. The conjugates may allow for the treatment of disease by effectively delivering drugs to treat the disease. In some embodiments wherein the drug binds a target, the conjugates may also be used to detect the target, detect or diagnose disease, and/or determine the efficacy of a treatment. The conjugates detailed herein may also be produced by genetic engineering, thereby facilitating their design and manipulation with precision, lower toxicity, better biocompatibility, and improved biodegradability.

1. Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

As used herein, the term "biomarker" refers to a naturally occurring biological molecule present in a subject at varying concentrations that is useful in identifying and/or classifying a disease or a condition. The biomarker can include genes, proteins, polynucleotides, nucleic acids, ribonucleic acids, polypeptides, or other biological molecules used as an indicator or marker for disease. In some embodiments, the biomarker comprises a disease marker. For example, the biomarker can be a gene that is upregulated or downregulated in a subject that has a disease. As another example, the biomarker can be a polypeptide whose level is increased or decreased in a subject that has a disease or risk of developing a disease. In some embodiments, the biomarker comprises a small molecule. In some embodiments, the biomarker comprises a polypeptide.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, or diseased after treatment, or a combination thereof.

The term "expression vector" indicates a plasmid, a virus or another medium, known in the art, into which a nucleic acid sequence for encoding a desired protein can be inserted or introduced.

The term "host cell" is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli*.

"Monodisperse" or "monodispersion" refers to a property of a plurality of conjugates, or polypeptides thereof, wherein each have about the same molecular weight. Genetically encoded synthesis of a conjugate may facilitate precise control of the molecular weight. Molecular weight is a factor that affects a molecule's circulation time in vivo, or its half-life.

"Opsonization" refers to the molecular mechanism whereby molecules, microbes, or apoptotic cells are chemically modified to have stronger interactions with cell surface receptors on phagocytes and natural killer (NK) cells. An antigen on the molecules, microbes, or apoptotic cell is coated in opsonins. The opsonins enhance binding to immune cells such as macrophages and neutrophils. Opsonization also mediates phagocytosis via signal cascades from cell surface receptors.

"Synthetic polymer" refers to a polymer which is produced from at least one monomer by a chemical process. A synthetic polymer is not produced directly by a living organism. Synthetic polymers include a homopolymer, heteropolymer, block polymer, copolymer, ter-polymer, etc., and blends, combinations and mixtures thereof. Examples of synthetic polymers include, but are not limited to, functionalized polymers, such as a polymer comprising 5-vinyltetrazole monomer units and having a molecular weight distribution less than 2.0. A synthetic polymer may be or contain one or more of a star block copolymer, a linear polymer, a branched polymer, a hyperbranched polymer, a dendritic polymer, a comb polymer, a graft polymer, a brush polymer, a bottle-brush copolymer and a crosslinked structure, such as a block copolymer comprising a block of 5-vinyltetrazole monomer units. Synthetic polymers include, without limitation, polyesters, poly(meth)acrylamides, poly(meth)acrylates, polyethers, polystyrenes, polynorbornenes and monomers that have unsaturated bonds. For example, amphiphilic comb polymers are described in U.S. Patent Application Publication No. 2007/0087114 and in U.S. Pat. No. 6,207,749 to Mayes et al., the disclosure of each of which is herein incorporated by reference in its entirety. The amphiphilic comb-type polymers may be present in the form of copolymers, containing a backbone formed of a hydrophobic, water-insoluble polymer and side chains formed of short, hydrophilic non-cell binding polymers. Examples of other synthetic polymers include, but are not limited to, polyalkylenes such as polyethylene and polypropylene and polyethyleneglycol (PEG); polychloroprene; polyvinyl ethers; such as poly(vinyl acetate); polyvinyl halides such as poly(vinyl chloride); polysiloxanes; polystyrenes; polyurethanes; polyacrylates; such as poly(methyl (meth)acrylate), poly(ethyl (meth)acrylate), poly(n-butyl(meth)acrylate), poly(isobutyl (meth) acrylate), poly(tert-butyl (meth)acrylate), poly(hexyl(meth) acrylate), poly(isodecyl (meth)acrylate), poly(lauryl (meth) acrylate), poly(phenyl (meth)acrylate), poly(methyl acrylate), poly(isopropyl acrylate), poly(isobutyl acrylate), and poly(octadecyl acrylate); polyacrylamides such as poly (acrylamide), poly(methacrylamide), poly(ethyl acrylamide), poly(ethyl methacrylamide), poly(N-isopropyl acrylamide), poly(n, iso, and tert-butyl acrylamide); and copolymers and mixtures thereof. These synthetic polymers may include useful derivatives, including synthetic polymers having substitutions, additions of chemical groups, for example, alkyl groups, alkylene groups, hydroxylations, oxidations, and other modifications routinely made by those skilled in the art. The synthetic polymers may include zwitterionic polymers such as, for example, polyphosphorycholine, polycarboxybetaine, and polysulfobetaine. The synthetic polymers may have side chains of betaine, carboxybetaine, sulfobetaine, oligoethylene glycol (OEG), sarcosine or polyethyleneglycol (PEG).

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids.

"Pharmacokinetics" as used herein refers the circulation of drugs in the body and its bioavailability, distribution, and excretion.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Reporter," "reporter group," "label," and "detectable label" are used interchangeably herein. The reporter is capable of generating a detectable signal. The label can produce a signal that is detectable by visual or instrumental means. A variety of reporter groups can be used, differing in the physical nature of signal transduction (e.g., fluorescence, electrochemical, nuclear magnetic resonance (NMR), and electron paramagnetic resonance (EPR)) and in the chemical nature of the reporter group. Various reporters include signal-producing substances, such as chromagens, fluorescent compounds, chemiluminescent compounds, radioactive compounds, and the like. In some embodiments, the reporter comprises a radiolabel. Reporters may include moieties that produce light, e.g., acridinium compounds, and moieties that produce fluorescence, e.g., fluorescein. In some embodiments, the signal from the reporter is a fluorescent signal. The reporter may comprise a fluorophore. Examples of fluorophores include, but are not limited to, acrylodan (6-acryloy 1-2-dimethylaminonaphthalene), badan (6-bromo-acetyl-2-dimethylamino-naphthalene), rhodamine, naphthalene, danzyl aziridine, 4[N-[(2-iodoacetoxy)ethyl]-N-methylamino]-7-nitrobenz-2-oxa-1,3-diazole ester (IANBDE), 4[N-[(2-iodoacetoxy)ethyl]-N-methylamino-7-nitrobenz-2-oxa-1,3-diazole (IANBDA), fluorescein, dipyrrometheneboron difluoride (BODIPY), 4-nitrobenzo[c][1,2,5]oxadiazole (NBD), Alexa fluorescent dyes, and derivatives thereof. Fluorescein derivatives may include, for example, 5-fluorescein, 6-carboxyfluorescein, 3'6-carboxyfluorescein, 5(6)-carboxyfluorescein, 6-hexachlorofluorescein, 6-tetrachlorofluorescein, fluorescein, and isothiocyanate.

"Sample" or "test sample" as used herein can mean any sample in which the presence and/or level of a target is to be detected or determined. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

The term "sensitivity" as used herein refers to the number of true positives divided by the number of true positives plus the number of false negatives, where sensitivity ("sens") may be within the range of 0<sens<1. Ideally, method embodiments herein have the number of false negatives equaling zero or close to equaling zero, so that no subject is wrongly identified as not having a disease when they indeed have the disease. Conversely, an assessment often is made of the ability of a prediction algorithm to classify negatives correctly, a complementary measurement to sensitivity.

The term "specificity" as used herein refers to the number of true negatives divided by the number of true negatives plus the number of false positives, where specificity ("spec") may be within the range of 0<spec<1. Ideally, the methods described herein have the number of false positives equaling zero or close to equaling zero, so that no subject is wrongly identified as having a disease when they do not in fact have disease. Hence, a method that has both sensitivity and specificity equaling one, or 100%, is preferred.

By "specifically binds," it is generally meant that a polypeptide binds to a target when it binds to that target more readily than it would bind to a random, unrelated target.

"Stealth" or "stealth polymer" refers to a conjugate, or to the polypeptide thereof, that can remain undetected by immune cells in the bloodstream for a prolonged period of time. Stealth polymers are at least partially resistant to enzymatic degradation of the conjugate, or to the polypeptide thereof, such as by proteases, and opsonization, which is a common method used by immune system to recognize foreign particles. Accordingly, stealth polymers may have one or more of reduced antigenicity, reduced immunogenicity, increased stability, increased half-life, and increased bioavailability relative to other polymers, conjugates, non-stealth polymers, and/or non-stealth conjugates. The ability to delay, reduce, or prevent opsonization, recognition by the immune system, or clearance of a conjugate (or the polypeptide or drug molecules thereof) from the body may be referred to herein as a stealth property.

"Subject" as used herein can mean a mammal that wants or is in need of the herein described conjugates or fusion proteins. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Target" as used herein can refer to an entity that a drug molecule binds. A target may include, for example, a small molecule, a protein, a polypeptide, a polynucleotide, a carbohydrate, or a combination thereof.

"Transition" or "phase transition" refers to the aggregation of the thermally responsive polypeptides. Phase transition occurs sharply and reversibly at a specific temperature called the lower critical solution temperature (LCST) or the inverse transition temperature $T_t$. Below the transition temperature, the thermally responsive polypeptide (or a polypeptide comprising a thermally responsive polypeptide) is highly soluble. Upon heating past the transition temperature, the thermally responsive polypeptides hydrophobically collapse and aggregate, forming a separate, gel-like phase. "Inverse transition cycling" refers to a protein purification method for thermally responsive polypeptides (or a polypeptide comprising a thermally responsive polypeptide). The protein purification method may involve the use of thermally responsive polypeptide's reversible phase transition behavior to cycle the solution through soluble and insoluble phases, thereby removing contaminants.

"Treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Water cage" refers to water molecules surrounding a molecule and interacting ionically with the molecule. The molecule may be, for example, a polypeptide, a ZiPP, a drug molecule, or a conjugate. When the molecule is in a solution, for example, the molecule forms ionic interactions with the surrounding water molecules such that a water cage is formed around it. For example, the positively and negatively charged amino acids of a polypeptide may form ionic interactions with water molecules around it in solution. The solution may include, for example, a subject's plasma or blood or other bodily fluid. Ionic interactions are stronger than hydrogen bonds or other intermolecular attractions and need more energy to become perturbed. In some embodiments, the water cage can shield the molecule (for example, a polypeptide, a ZiPP, a drug molecule, or a conjugate) from degradation or opsonization. A water cage may confer a stealth property to a molecule.

"Zwitterionic" or "zwitterion" refers to a molecule with net charge of zero, but including negative and positive charges on independent individual atoms within the molecule. The charged atoms are joined by one or more covalent bonds. A polypeptide may be zwitterionic.

2. Conjugate

The conjugate includes a polypeptide and one or more drug molecules attached to the polypeptide. The conjugate may further include at least one linker. The conjugates are considered stealth polymers for drug delivery.

a. Polypeptide

The polypeptide comprises one or more charged motifs. The charged motif includes one or more positively charged amino acids and one or more negatively charged amino acids, wherein the positively charged amino acids and negatively charged amino acids are present in a ratio of 1:1. In some embodiments, the net charge of the motif is neutral. In some embodiments, the charged motif is a zwitterionic motif. The positively charged amino acids within one motif may be the same or different. The negatively charged amino acids within one motif may be the same or different. As used herein, the charge of an amino acid (positive and/or negative) refers to the charge of the amino acid side chain. A charged amino acid is positively and/or negatively charged at neutral pH, at physiological pH, or at the local pH within the protein fold, or a combination thereof. The charged motif may further include one or more uncharged amino acids. In some embodiments, the charged motif has an amino acid sequence of $VPX_1X_2G$ (SEQ ID NO: 1), wherein $X_1$ is a negatively or positively charged amino acid, and wherein $X_2$ is the other of a negatively or positively charged amino acid. A polypeptide comprising one or more charged motifs may be a zwitterionic polypeptide (ZiPP). ZiPPs are overall neutral polypeptides that include both amino acids with negative charge and amino acids with positive charge.

In some embodiments, the polypeptide comprises a plurality of charged motifs. The plurality of charged motifs may be repeated. In some embodiments, polypeptide comprises the amino acid sequence of $(VPX_1X_2G)_n$ (SEQ ID NO: 2), wherein $X_1$ is a negatively or positively charged amino acid, $X_2$ is the other of a negatively or positively charged amino acid, and n is an integer greater than or equal to 1. $X_1$ may be the same or different between adjacent motifs. $X_2$ may be the same or different between adjacent motifs. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, a polypeptide comprising the amino acid sequence of $(VPX_1X_2G)_n$ (SEQ ID NO: 2), wherein $X_1$ is a negatively or positively charged amino acid, $X_2$ is the other of a negatively or positively charged amino acid, and n is an integer greater than or equal to 1, may be referred to as a homopolymer.

In some embodiments, the polypeptide includes one or more uncharged motifs in addition to the one or more charged motifs. The uncharged motif includes uncharged amino acids. In some embodiments, the uncharged motif does not include any charged amino acids. In some embodiments, the uncharged motif has an amino acid sequence consisting of VPGXG (SEQ ID NO: 3), wherein X is any amino acid except proline.

A plurality of uncharged motifs may be repeated in tandem. In some embodiments, the polypeptide comprises the amino acid sequence of $(VPGXG)_n$ (SEQ ID NO: 4) in addition to the one or more charged motifs, wherein X is any amino acid except proline, and n is an integer greater than or equal to 1. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, polypeptides comprising an uncharged motif having an amino acid sequence consisting of $(VPGXG)_n$ (SEQ ID NO: 4) in addition to the one or more charged motifs, wherein X is any amino acid except proline, and n is an integer greater than or equal to 1, are referred to as elastin-like polypeptides (ELP).

The motifs of the polypeptide can be arranged in any number of possible ways. Examples of possible arrangements and architectures are shown in FIG. 1. In FIG. 1, the gray block denotes a positively charged amino acid while the black block denotes a negatively charged amino acid. FIG. 1A shows an example of a homopolymer, wherein each unit is a repeat of the pentapeptide sequence $VPX_1X_2G$ (SEQ ID NO: 1), or charged motif. FIG. 1D shows possible sequences of $VPX_1X_2G$ (SEQ ID NO: 1). FIG. 1B shows an example of a diblock polymer. In a diblock architecture, one block of polymer is made with a repeating charged motif, while the other part includes a repeating uncharged motif. FIG. 1C shows an example of a multiblock polymer, wherein the charged motifs and uncharged motifs are placed at different sites to increase diversity of the polymer. The particular number, identity, and arrangement of motifs may be designed to create a conjugate that can achieve an optimal level of solvation, create a water cage, and/or create a layer around itself to help improve the pharmacokinetics of the therapeutics or drug molecules. In some embodiments, the polypeptide is arranged to confer a stealth property to the polypeptide or conjugate. In some embodiments, one or more uncharged motifs are positioned between at least two adjacent charged motifs of the polypeptide. In some embodiments, the polypeptide includes a plurality of charged motifs repeated in tandem and a plurality of uncharged motifs repeated in tandem. In some embodiments, the plurality of charged motifs repeated in tandem are positioned C-terminal to the plurality of uncharged motifs repeated in tandem. In some embodiments, the plurality of charged motifs repeated in tandem are positioned N-terminal to the plurality of uncharged motifs repeated in tandem.

In some embodiments, the polypeptide comprises the amino acid sequence of $(VPX_1X_2G)_n(VPGXG)_m$ (SEQ ID NO: 5), wherein $X_1$ is a negatively or positively charged amino acid, $X_2$ is the other of a negatively or positively charged amino acid, X is any amino acid except proline, and n and m are independently an integer greater than or equal to 1. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, m is an integer less than or equal to about 100, 200, 300, 400, or 500. In some embodiments, m is an integer greater than or equal to about 1, 10, 50, 100, 150, or 200. In some embodiments, m is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, m is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, a polypeptide comprising the amino acid sequence of $(VPX_1X_2G)_n(VPGXG)_m$ (SEQ ID NO: 5), wherein $X_1$ is a negatively or positively charged amino acid, $X_2$ is the other of a negatively or positively charged amino acid, X is any amino acid except proline, and n and m are independently an integer greater than or equal to 1, may be referred to as a diblock polymer.

In some embodiments, the polypeptide comprises the amino acid sequence of $(VPGXG)_m(VPX_1X_2G)_n$ (SEQ ID NO: 6), wherein $X_1$ is a negatively or positively charged amino acid, $X_2$ is the other of a negatively or positively charged amino acid, X is any amino acid except proline, and n and m are independently an integer greater than or equal to 1. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, m is an integer less than or equal to about 100, 200, 300, 400, or 500. In some embodiments, m is an integer greater than or equal to about 1, 10, 50, 100, 150, or 200. In some embodiments, m is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, m is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, a polypeptide comprising the amino acid sequence of $(VPGXG)_m(VPX_1X_2G)_n$ (SEQ ID NO: 6), wherein $X_1$ is a negatively or positively charged amino acid, $X_2$ is the other of a negatively or positively charged amino acid, X is any amino acid except proline, and n and m are independently an integer greater than or equal to 1, may be referred to as a diblock polymer.

In some embodiments, the polypeptide comprises the amino acid sequence of $\{(VPX_1X_2G)(VPGXG)\}_b$ (SEQ ID NO: 7), wherein $X_1$ is a negatively or positively charged amino acid, $X_2$ is the other of a negatively or positively charged amino acid, X is any amino acid except proline, and b is an integer greater than or equal to 1. In some embodiments, b is an integer less than or equal to about 100, 200, or 300. In some embodiments, b is an integer greater than or equal to about 1, 10, 50, 100, 150, or 200. In some embodiments, b is an integer from about 10 to about 300, from about 10 to about 200, from about 10 to about 100, from about 10 to about 50, from about 1 to about 300, from about 1 to about 200, from about 1 to about 100, or from about 1 to about 50. In some embodiments, b is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300. In some embodiments, a polypeptide comprising the amino acid sequence of $\{(VPX_1X_2G)(VPGXG)\}_b$ (SEQ ID NO: 7), wherein $X_1$ is a negatively or positively charged amino acid, $X_2$ is the other of a negatively or positively charged amino acid, X is any amino acid except proline, and b is an integer greater than or equal to 1, may be referred to as a multiblock polymer.

In some embodiments, $X_1$ is a negatively charged amino acid, and $X_2$ is a positively charged amino acid. In some embodiments, $X_1$ is a positively charged amino acid, and $X_2$ is a negatively charged amino acid. In some embodiments, the negatively charged amino acid is independently selected from glutamatic acid and aspartic acid. In some embodiments, the positively charged amino acid is independently selected from lysine and arginine. In some embodiments, X is selected from arginine, histidine, lysine, aspartic acid, glutamic acid, serine, threonine, asparagine, glutamine, cysteine, selenocysteine, glycine, alanine, valine, leucine, isoleucine, methionine, phenylalanine, tyrosine, and tryptophan. In some embodiments, X is selected from glycine and valine.

In some embodiments, the polypeptide is temperature-sensitive, which may also be referred to as thermally responsive. Thermally responsive polypeptides may have a phase transition. A thermally responsive polypeptide may impart a phase transition characteristic to the polypeptide and/or conjugate. Phase transition occurs sharply and reversibly at a specific temperature called the lower critical solution temperature (LCST) or the inverse transition temperature (Tt). "Phase transition" or "transition" may also refer to the aggregation of the thermally responsive polypeptide. Below the transition temperature (LCST or Tt), the thermally responsive polypeptides (or polypeptides comprising a thermally responsive polypeptide) may be highly soluble. Upon heating above the transition temperature, thermally responsive polypeptides hydrophobically may collapse and aggregate, forming a separate, gel-like phase or insoluble hydrophobic aggregates. The thermal responsive property of the polypeptide may be utilized in purification of the polypeptide and/or conjugate according to a method referred to as "inverse transition cycling. Phase transition may also be triggered using kosmotropic salts, such as, for example, ammonium sulfate. Sodium chloride, for example, may be used with the kosmotropic salt. The kosmotropic salt may be added to a solution comprising the polypeptide and/or conjugate, with the kosmotropic salt being added until the polypeptide and/or conjugate forms aggregates or is precipitated out of solution. The aggregates may be pelleted by centrifugation and resuspended in a second solution or buffer. Aggregates of the polypeptide and/or conjugate may re-solubilize into solution once cooled below their Tt or when the kosmotropic salt is removed from the solution. In some embodiments, the conjugates are purified without any chromatographic purification. In some embodiments, the conjugates are generated recombinantly and purified from bacterial culture, such as, for example, from $E.$ $coli.$ b. Drug Molecule The conjugate may include one or more drug molecules. The drug molecule may be a therapeutic. In some embodiments, the drug molecule is selected from a small molecule, nucleotide, polynucleotide, protein, polypeptide, carbohydrate, and a combination thereof. In some embodiments, the drug molecule comprises a small molecule. In some embodiments, the drug molecule comprises a protein. In some embodiments, the drug molecule comprises a cancer therapeutic. In some embodiments, the drug molecule comprises an antibody. In some embodiments, the drug molecule comprises Tn3 (TRAIL superagonist). In some embodiments, the drug molecule is attached to a cysteine of the polypeptide of the conjugate.

The conjugate may include 1, 2, 3, 4, 5, 6, 7, 8, 9, or 10 drug molecules. The conjugate may include at least about 1, at least about 2, or at least about 3 drug molecules. The conjugate may include less than about 10, less than about 8, or less than about 5 drug molecules. In some embodiments, the conjugate includes 1 drug molecule. In some embodiments, the conjugate includes 1 drug molecule per polypeptide of the conjugate. In some embodiments, the conjugate includes 1-10 drug molecules. In some embodiments, the conjugate includes 2-5 drug molecules.

c. Linker

In some embodiments, the conjugate further includes at least one linker. In some embodiments, the conjugate includes more than one linker. In such embodiments, the linkers may be the same or different from one another. The conjugate may include at least 1, at least 2, at least 3, at least 4, at least 5, at least 6, at least 7, at least 8, at least 9, or at least 10 linkers. The conjugate may include less than 20, less than 15, less than 10, or less than 5 linkers. The conjugate may include between 1 and 20, between 5 and 15, or between 1 and 5 linkers. The linker may be positioned in at the C-terminus of the polypeptide, at the N-terminus of the polypeptide, or at both the N- and C-termini of the polypeptide. In some embodiments, the linker may be positioned anywhere within a polypeptide sequence. Multiple linkers may be positioned adjacent to one another.

The linker may be a polypeptide of any amino acid sequence and length. The linker may act as a spacer peptide. In some embodiments, the linker comprises charged amino acids. In some embodiments, the linker comprises uncharged amino acids. In some embodiments, the linker is flexible. In some embodiments, the linker comprises one or more cysteines. In some embodiments, the linker comprises an amino acid sequence selected from SEQ ID NO: 8 (GGC), SEQ ID NO: 9 ((GGC)$_8$), SEQ ID NO: 10 ((G$_4$S)$_3$), and SEQ ID NO: 11 ((VPGXG)$_{16}$ wherein X is valine or cysteine present in a ratio of 1:1).

The linker may serve as an attachment site for the drug molecule to the polypeptide. The drug molecule may attach to the linker by any suitable means known in the art. The drug molecule may attach to the linker through a thiol reactive linking group. In some embodiments, the one or more drug molecules are attached to the polypeptide via the linker. In some embodiments, the drug molecule is attached to the polypeptide through a thiol reactive group in the linker.

3. Polynucleotides

Further provided are polynucleotides encoding the conjugates detailed herein. A vector may include the polynucleotide encoding the conjugates detailed herein. To obtain expression of a polypeptide, one may subclone the polynucleotide encoding the polypeptide into an expression vector that contains a promoter to direct transcription, a transcription/translation terminator, and if for a nucleic acid encoding a protein, a ribosome binding site for translational initiation. An example of a vector is pet24. Suitable bacterial promoters are well known in the art. Further provided is a host cell transformed or transfected with an expression vector comprising a polynucleotide encoding a conjugate as detailed herein. Bacterial expression systems for expressing the protein are available in, e.g., $E.$ $coli,$ $Bacillus$ sp., and $Salmonella$ (Paiva et al., $Gene$ 1983, 22, 229-235; Mosbach et al., $Nature$ 1983, 302, 543-545). Kits for such expression systems are commercially available. Eukaryotic expression systems for mammalian cells, yeast, and insect cells are well known in the art and are also commercially available. Retroviral expression systems can be used in the present invention. In some embodiments, the conjugate comprises a polypeptide comprising an amino acid sequence of SEQ ID NOs: 12. In some embodiments, the conjugate comprises a polypeptide encoded by a polynucleotide sequence of SEQ ID NOs: 13.

The conjugate may be expressed recombinantly in a host cell according to one of skill in the art. The conjugate may be purified by any means known to one of skill in the art. For example, the conjugate may be purified using chromatography, such as liquid chromatography, size exclusion chromatography, or affinity chromatography, or a combination thereof. In some embodiments, the conjugate is purified without chromatography. In some embodiments, the conjugate is purified using inverse transition cycling.

4. Administration

A composition may comprise the conjugate. The conjugates as detailed above can be formulated into a composition in accordance with standard techniques well known to those skilled in the pharmaceutical art. The composition may be prepared for administration to a subject. Such compositions comprising a conjugate can be administered in dosages and by techniques well known to those skilled in the medical arts taking into consideration such factors as the age, sex, weight, and condition of the particular subject, and the route of administration.

The conjugate can be administered prophylactically or therapeutically. In prophylactic administration, the conjugate can be administered in an amount sufficient to induce a response. In therapeutic applications, the conjugates are administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The conjugate can be administered by methods well known in the art as described in Donnelly et al. (*Ann. Rev. Immunol.* 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The conjugate can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The conjugates can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the conjugate is administered intravenously, intraarterially, or intraperitoneally to the subject.

The conjugate can be a liquid preparation such as a suspension, syrup, or elixir. The conjugate can be incorporated into liposomes, microspheres, or other polymer matrices (such as by a method described in Feigner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The conjugate may be used as a vaccine. The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation can be carried out via a minimally invasive device.

In some embodiments, the conjugate is administered in a controlled release formulation. The conjugate may be released into the circulation or a tumor, for example. In some embodiments, the conjugate may be released over a period of at least about 1 day, at least about 2 days, at least about 3 days, at least about 4 days, at least about 5 days, at least about 6 days, at least about 7 days, at least about 1 week, at least about 1.5 weeks, at least about 2 weeks, at least about 2.5 weeks, at least about 3.5 weeks, at least about 4 weeks, or at least about 1 month.

5. Detection

As used herein, the term "detect" or "determine the presence of" refers to the qualitative measurement of undetectable, low, normal, or high concentrations of one or more conjugates bound to target. In some embodiments, the target may be a biomarker. Detection may include in vitro, ex vivo, or in vivo detection. Detection may include detecting the presence of one or more conjugates or targets versus the absence of the one or more conjugates or targets. Detection may also include quantification of the level of one or more conjugates or targets. The term "quantify" or "quantification" may be used interchangeably, and may refer to a process of determining the quantity or abundance of a substance (e.g., conjugate or target), whether relative or absolute. Any suitable method of detection falls within the general scope of the present disclosure. In some embodiments, the conjugate comprises a reporter attached thereto for detection. In some embodiments, the conjugate is labeled with a reporter. In some embodiments, detection of conjugate bound to target may be determined by methods including but not limited to, band intensity on a Western blot, flow cytometry, radiolabel imaging, cell binding assays, activity assays, SPR, immunoassay, or by various other methods known in the art.

In some embodiments, including those wherein the conjugate comprises an antibody for binding and/or detecting a target, any immunoassay may be utilized. The immunoassay may be an enzyme-linked immunoassay (ELISA), radioimmunoassay (RIA), a competitive inhibition assay, such as forward or reverse competitive inhibition assays, a fluorescence polarization assay, or a competitive binding assay, for example. The ELISA may be a sandwich ELISA. Specific immunological binding of the conjugate to the target can be detected via direct labels, attached to the conjugate or via indirect labels, such as alkaline phosphatase or horseradish peroxidase. The use of immobilized conjugates may be incorporated into the immunoassay. The conjugates may be immobilized onto a variety of supports, such as magnetic or chromatographic matrix particles, the surface of an assay plate (such as microtiter wells), pieces of a solid substrate material, and the like. An assay strip can be prepared by coating the conjugate or plurality of conjugates in an array on a solid support. This strip can then be dipped into the test biological sample and then processed quickly through washes and detection steps to generate a measurable signal, such as a colored spot.

6. Methods a. Methods of Delivering a Drug Molecule

The present invention is directed to a method of delivering a drug molecule to a subject. The method may include administering the conjugate as described herein to the subject. In some embodiments, the conjugate has an improved property relative to the drug molecule alone or the drug molecule conjugated to a synthetic polymer such as polyethylene glycol (PEG), the improved property selected from, for example, stealth, biocompatibility, solubility, stability, half-life, retention in plasma, antigenicity, immunogenicity, monodispersion, or a combination thereof. In some embodiments, the conjugate is easily synthesized. In some embodiments, the conjugate is easily purified. In some embodiments, the easy synthesis and/or purification may lead to improved cost-effectiveness of the conjugates. In some embodiments, the conjugate, or polypeptide thereof, is genetically encoded, thereby facilitating the design of a conjugate with a precise molecular weight. In some embodiments, the molecular weight of the conjugate determines and/or affects its half-life in vivo. Being able to easily and precisely control the molecular weight of the conjugate may facilitate control of the half-life of the conjugate in vivo. In comparison, it may not be easy to control the molecular weight of synthetic polymers such as PEG. In some embodiments, the conjugate has reduced antigenicity relative to the drug molecule conjugated to a synthetic polymer such as polyethylene glycol (PEG). In some embodiments, the conjugate has reduced immunogenicity relative to the drug molecule conjugated to a synthetic polymer such as polyethylene glycol (PEG).

b. Methods of Treating a Disease

The present invention is directed to a method of treating a disease in a subject in need thereof. The method may comprise administering to the subject an effective amount of the conjugate as described herein. The disease may be, for example, cancer, a metabolic disease, an autoimmune disease, a cardiovascular disease, or a orthopedic disorder.

Metabolic disease may occur when abnormal chemical reactions in the body alter the normal metabolic process. Metabolic diseases may include, for example, insulin resistance, non-alcoholic fatty liver diseases, type 2 diabetes, insulin resistance diseases, cardiovascular diseases, arteriosclerosis, lipid-related metabolic disorders, hyperglycemia, hyperinsulinemia, hyperlipidemia, and glucose metabolic disorders.

Autoimmune diseases arise from an abnormal immune response of the body against substances and tissues normally present in the body. Autoimmune diseases may include, but are not limited to, lupus, rheumatoid arthritis, multiple sclerosis, insulin dependent diabetes mellitus, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, polyarteritis nodosa, myocarditis, psoriasis, Celiac disease, Crohn's disease, ulcerative colitis, and fibromyalgia.

Cardiovascular disease is a class of diseases that involve the heart or blood vessels. Cardiovascular diseases may include, for example, coronary artery diseases (CAD) such as angina and myocardial infarction (heart attack), stroke, hypertensive heart disease, rheumatic heart disease, cardiomyopathy, heart arrhythmia, congenital heart disease, valvular heart disease, carditis, aortic aneurysms, peripheral artery disease, and venous thrombosis.

Orthopedic disorders or musculoskeletal disorders are injuries or pain in the body's joints, ligaments, muscles, nerves, tendons, and structures that support limbs, neck, and back. Orthopedic disorders may include degenerative diseases and inflammatory conditions that cause pain and impair normal activities. Orthopedic disorders may include, for example, carpal tunnel syndrome, epicondylitis, and tendinitis.

Cancers may include, but are not limited to, breast cancer, colorectal cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers. In some embodiments, the cancer is breast cancer.

c. Methods of Diagnosing a Disease

Provided herein are methods of diagnosing a disease. The methods may include administering to the subject a conjugate as described herein, and detecting binding of the conjugate to a target to determine presence of the target in the subject. The presence or absence of the target may indicate the disease in the subject. In other embodiments, the methods may include contacting a sample from the subject with a conjugate as described herein, determining the level of a target in the sample, and comparing the level of the target in the sample to a control level of the target, wherein a level of the target different from the control level indicates disease in the subject. In some embodiments, detected levels of the target less than a control may indicate disease. In some embodiments, detected levels of the target greater than a control may indicate disease. In some embodiments, the disease is selected from cancer, metabolic disease, autoimmune disease, cardiovascular disease, and orthopedic disorders, as detailed above. In some embodiments, the target comprises a disease marker or biomarker.

d. Methods of Determining the Presence-Of a Target

Provided herein are methods of determining the presence of a target in a sample. The methods may include contacting the sample with a conjugate as described herein under conditions to allow a complex to form between the conjugate and the target in the sample, and detecting the presence of the complex. Presence of the complex may be indicative of the target in the sample. The target may be a protein or a nucleic acid, for example. The protein may be a receptor or an antigen, for example. The antigen may be associated with a disease, for example. In some embodiments, the target comprises a biomarker. In some embodiments, the conjugate is labeled with a reporter for detection.

In some embodiments, the sample is obtained from a subject and the method further includes diagnosing, prognosticating, or assessing the efficacy of a treatment of the subject. When the method includes assessing the efficacy of a treatment of the subject, the method may further include modifying the treatment of the subject as needed to improve efficacy.

e. Methods of Determining the Effectiveness of a Treatment

Provided herein are methods of determining the effectiveness of a treatment for a disease in a subject in need thereof. The methods may include contacting a sample from the subject with a conjugate as detailed herein under conditions to allow a complex to form between the conjugate and a target in the sample, determining the level of the complex in the sample, wherein the level of the complex is indicative of the level of the target in the sample, and comparing the level of the target in the sample to a control level of the target, wherein if the level of the target is different from the control level, then the treatment is determined to be effective or ineffective in treating the disease.

Time points may include prior to onset of disease, prior to administration of a therapy, various time points during administration of a therapy, and after a therapy has concluded, or a combination thereof. Upon administration of the conjugate to the subject, the conjugate may bind a target, wherein the presence or absence of the target indicates the presence of the disease in the subject at the various time points. In some embodiments, the target comprises a disease marker or biomarker. Comparison of the binding of the conjugate to the target at various time points may indicate whether the disease has progressed, whether the diseased has advanced, whether a therapy is working to treat or prevent the disease, or a combination thereof.

In some embodiments, the control level corresponds to the level in the subject at a time point before or during the period when the subject has begun treatment, and the sample is taken from the subject at a later time point. In some embodiments, the sample is taken from the subject at a time point during the period when the subject is undergoing treatment, and the control level corresponds to a disease-free level or to the level at a time point before the period when the subject has begun treatment. In some embodiments, the method further includes modifying the treatment or administering a different treatment to the subject when the treatment is determined to be ineffective in treating the disease.

7. Examples

Example 1

Materials and Methods

Cloning. The synthetic genes for ZiPPs were assembled from chemically synthesized oligomers (IDT Inc.; Coralville, Iowa). The oligomers were cloned into a pET expression vector in *E. coli* using plasmid reconstruction recursive directional ligation (Pre-RDL) technique (McDaniel, J. R., et al. *Biomacromolecules*, 2010, 11, 944-952).

Expression and purification of ZiPPs by inverse transition cycling (ITC). ZiPPs were expressed from a pET expression vector in *E. coli*. All ZiPPs in aqueous solution show a reversible inverse phase transition. They go from being a soluble protein to insoluble hydrophobic aggregates when heated above their transition temperature (Tt). The same phenomena (phase separation) can be also triggered using kosmotropic salts. Aggregates of ZiPPs can re-solubilize into the solution once cooled below their Tt or when the salt is removed from the solution. This thermally responsive property of ZiPP enables a simple non-chromatographic method for protein purification. This method of purification is called "inverse transition cycling" (ITC) (Meyer, D. E. and A. Chilkoti. *Nat. Biotech.* 1999, 17, 1112-1115; MacEwan, S. R., et al. *J. Vis. Exp.* 2014, 88, e51583).

In a typical purification of ZiPPs by ITC, *E. coli* cells from 1 L culture are recovered by centrifugation and resuspended in cold PBS. The cells are then lysed by ultrasonic disruption at 4° C. The *E. coli* lysate is then centrifuged at 15,000×g to remove the cell wall and other cellular debris. ZiPPs are soluble proteins that are present in the soluble fraction (supernatant) of the cell lysate. Polyethylenimine is added to the supernatant of the cell lysate, and centrifuged at 14,000×g to pallet DNA and any remaining bacterial cell walls. ZiPPs are then purified from the supernatant by triggering phase separation using ammonium sulfate and sodium chloride, followed by centrifugation at 15,000×g for 15 minutes at 4° C. The pallet is then resuspended in cold PBS, and any insoluble matter is removed by a centrifugation step at 4° C. for 10 min. These steps are repeated until homogeneity, which is confirmed by the appearance of a single band in SDS-PAGE gel. The molecular weight (MW) was also confirmed with Voyager DE-Pro MALDI-TOF (Applied Biosystems; Foster City, Calif.) instrument. The unstructured nature of ZiPPs was confirmed with Circular Dichroism Instrument (Aviv 202). For animal experiments, endotoxin is removed using a Detoxi-Gel (Thermo Scientific; Waltham, Mass.).

In vivo pharmacokinetics (PK) Study. In this study ZiPPs were compared with uncharged polymers $(VPGAG)_{120}$ and $(VPGAG)_{160}$. The polymers were fluorescently labeled with Alexa 488 in the N-terminus and injected into Balb/c mice using tail vein injection. VPGAG, a biopolymer of similar nature but without any charges, was used as a control to show that any change in the pharmacokinetic parameters seen is the result of the charges incorporated in the $VPX_1X_2G$ motif. Each mouse received a single dose of ZiPPs or control (150 mg/kg BW), injected i.v or subcutaneously. Blood samples were collected (10 µL collected into tubes with 100 µL of heparin) at 40 sec, 15 min, 0.5, 2, 4, 8, 24, 48, and 72 hours after injection from the tail vein. The concentration of fluorescently labeled polymer in the blood was calculated using a standard curve of Alexa 488. Blood concentration time-course data was analyzed with a standard two compartment PK model for i.v. pk data to ascertain the pharmacokinetic parameters.

Paclitaxel (PTX) conjugation. Eight periodically spaced cysteine residues arranged in a $(VPGXG)_{16, \, x \, is \, V \, or \, C \, 1:1}$, motif was cloned to the C-terminus of ZiPP. The drug conjugation segment contained eight cysteines to which multiple copies of PTX were conjugated. First 2'OH of PTX was modified with levulinic acid (Etrych, T. S., et al. *Molecular Pharmaceutics* 2010, 7, 1015-1026). This modification retains the cytotoxicity of PTX. Activated PTX was then conjugated to free thiols using an acid-labile hydrazide linker (N-ε-Maleimidocaproic acid hydrazide (EMCH) linker) with a terminal maleimide that reacted with thiol groups on ZiPPs to form a stable carbon-sulfur bond (Andrew MacKay, J., et al. *Nat. Mater.* 2009, 8, 993-999).

Characterization of ZiPP-PTX drug conjugation. Purity of the drug conjugation was evaluated using High Performance Liquid Chromatography (HPLC). The HPLC data was quantified using the integrated area under the peak at an absorbance of 228 nm that corresponds to the absorbance of PTX. The conjugation ratio of drugs to ZiPPs was determined by matrix-assisted laser desorption/ionization time-of-flight mass spectrometry (MALDI-TOF-MS) a Voyager DE-Pro MALDI-MS (Applied Biosystems; Foster City, Calif.) instrument equipped with a nitrogen laser (337 nm). Dynamic Light Scattering (DLS) technique was performed to determine the hydrodynamic radius (Rh) of the ZiPP-PTX nanoparticle at 25° C. and 25 µM concentration using a Dynapro plate reader (Wyatt Technology; Santa Barbara, Calif.). The data was analyzed with a regularization fit of the autocorrelation function and the percentage intensity was converted to mass intensity using Raleigh spheres model. Regularization fit was then used to determine the hydrodynamic radius as weighted by the percent by mass for a random coil. Radius of gyration was calculated using Static Light Scattering (SLS) after PTX conjugation. The form factor (ρ) was calculated as Rg/Rh.

In vitro cytotoxicity of ZiPP-PTX conjugates. In vitro cytotoxicity was done on MDA-MB-231 human triple negative breast cancer cells. $3 \times 10^3$ cells were seeded per 100 µL of media in Falcon™ 96-well cell culture plates (BD; Franklin Lakes, N.J.). The cells were allowed to adhere for 16-18 hours before being treated with free PTX and ZiPP-PTX at concentrations that ranged from sub-nanomolar to high-micromolar range. After 72 hours of drug treatment, 20 µL of 3-(4,5-dimethyl2-yl)-5-(3-carboxymethoxyphenyl)-2-(4-sulfophenyl)-2H-tetrazolium (MTS) reagent (CellTiter 96 AQueous™ Promega; Madison, Wis.) was added to each well and incubated for an additional 2 hours. A dose-response curve for free drug and ZiPP-drug conjugate was constructed by measuring the absorbance of each well at 490 nm with a Victor3 microplate reader (Perkin Elmer; Waltham, Mass.). The 50% inhibitory concentration, $IC_{50}$, was determined by fitting data to the following equation (Andrew MacKay, J., et al. *Nat. Mater.* 2009, 8, 993-999):

$$V_\% = 100\% \bigg/ \left[1 + \left(\frac{C_{treatment}}{IC_{50}}\right)^p\right]$$

where V is viability of cells, $C_{treatment}$ is drug concentration, and p is slope of the dose response curve. This $IC_{50}$ value is used to evaluate the potency of the conjugates.

Example 2

Expression and Purification of ZiPPs

Figure 2A:
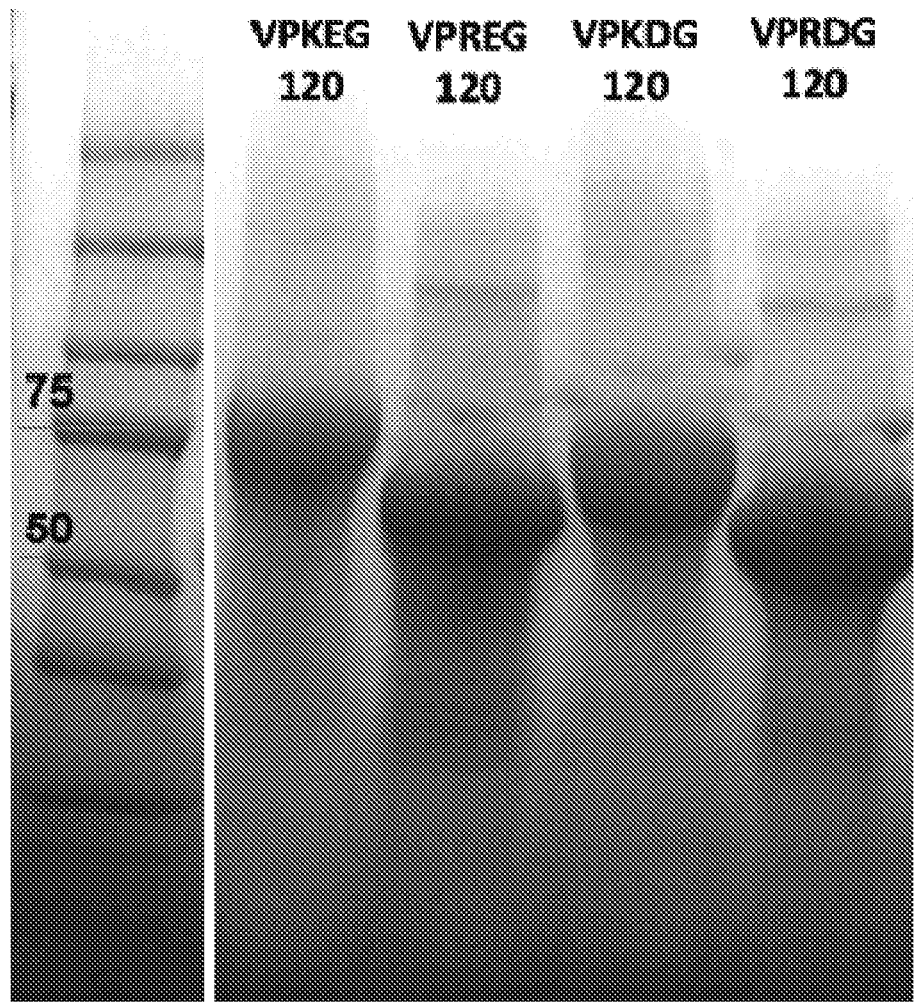
FIG. 2 shows the characterization of ZiPPs. The ZiPP constructs used were 120 repeats of the pentapeptide zwitterionic motif. (A) SDS page analysis of purified ZiPP constructs. (B) Representative MALDI spectra for $(VPKDG)_{120}$ and $(VPRDG)_{120}$ confirmed the MW of purified ZiPP constructs (MW=60.5 kDa, MW=63.8 kDa, respectively). (C) Hydrodynamic radius measured using Dynamic Light Scattering showed well hydrated ZiPPs compared to ELP controls. (D) CD-Spectra of ZiPPs showed negative ellipticity in low wavelength and slightly positive ellipticity in higher wavelength, which is typical of a disordered structure like ELPs. (E) Native PAGE gel showed that ZiPPs did not interact with albumin.
Figure 2B:
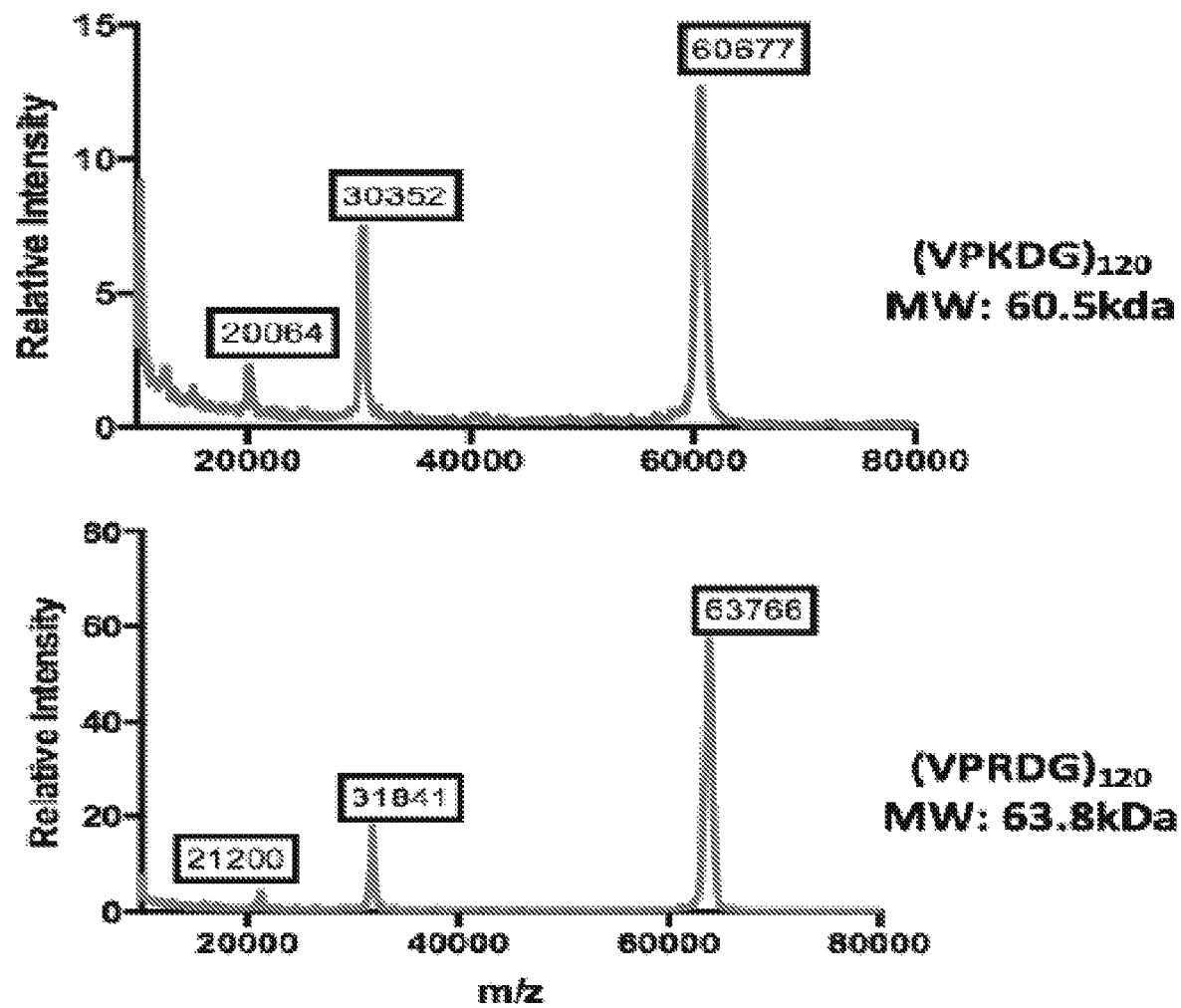
Figure 2C:
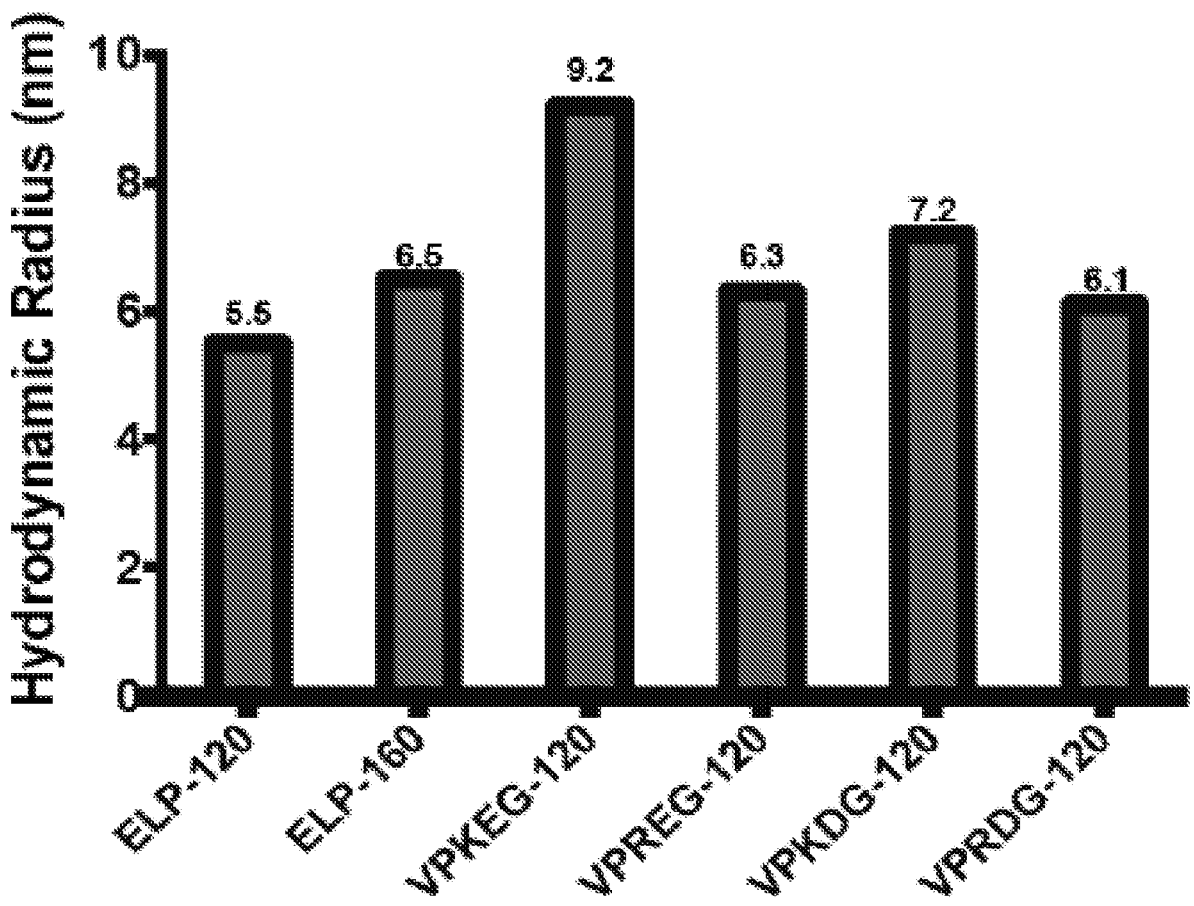
Figure 2D:
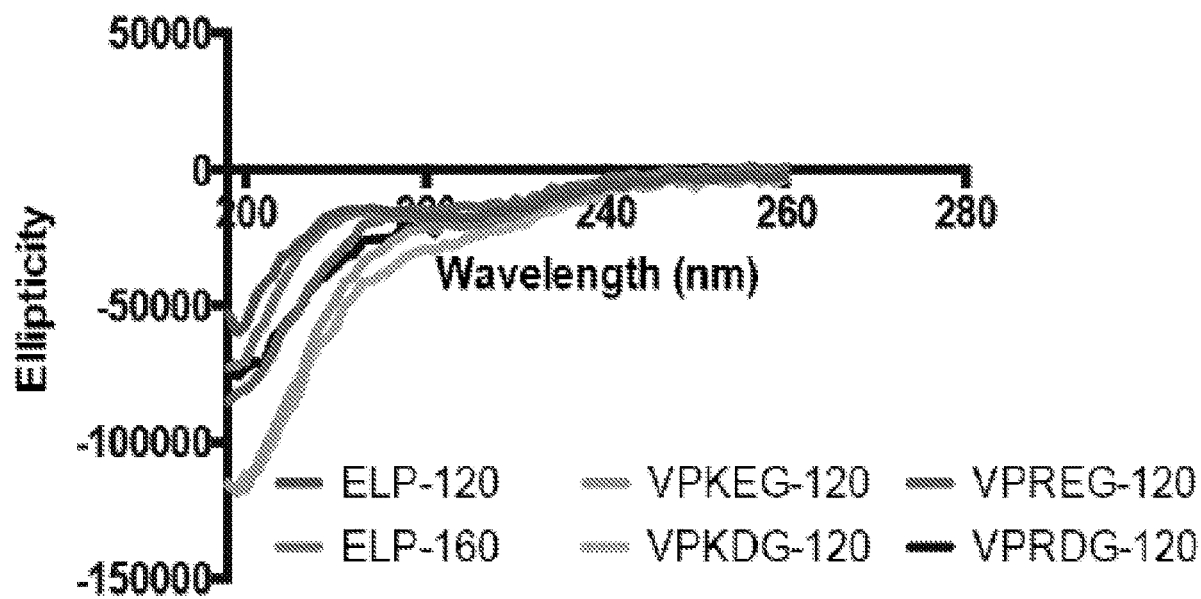
Figure 2E:
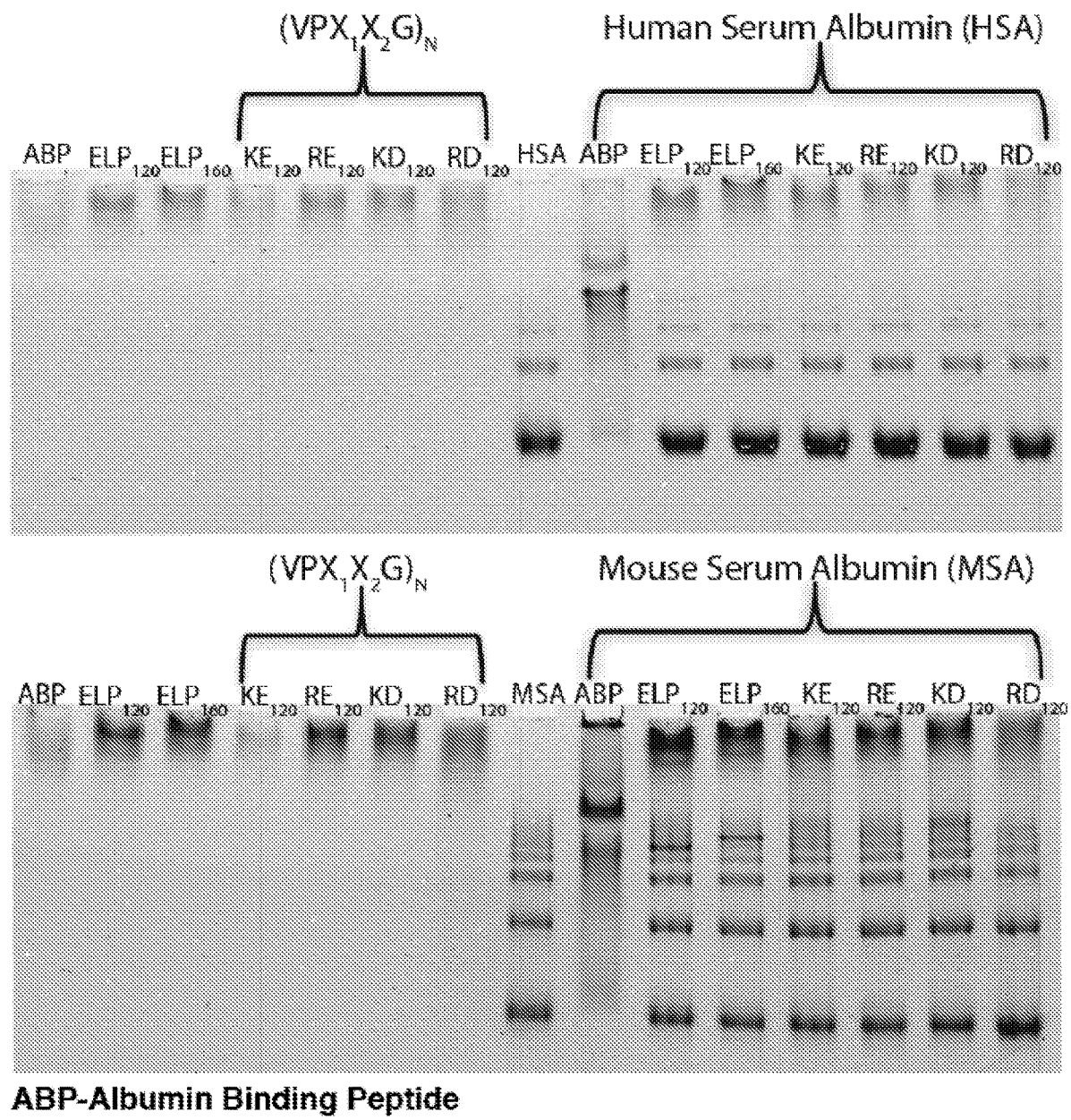
Figures 7A, 7B:
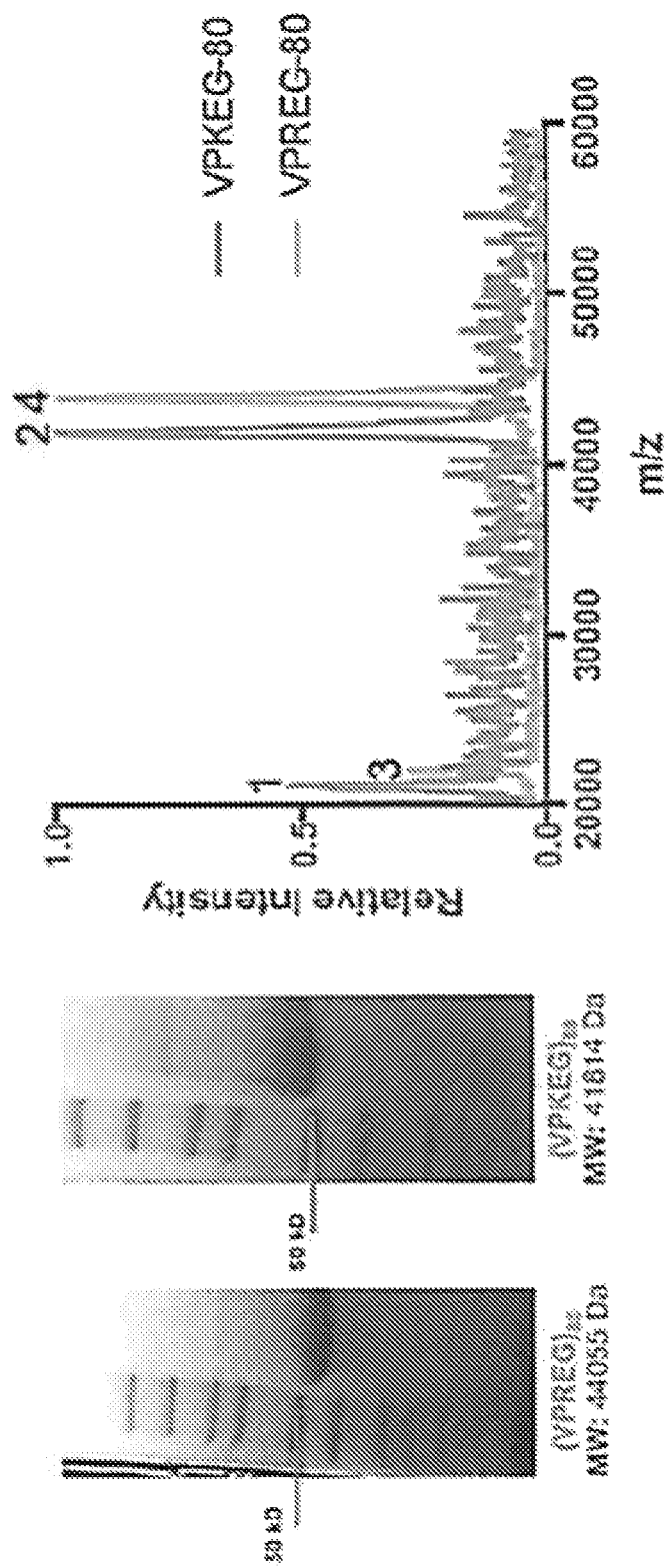
FIG. 7 shows the characterization of ZiPPs. The ZiPP constructs used were 80 repeats of the pentapeptide zwitterionic motif. (A) SDS page analysis of purified ZiPP constructs. The 50 kD and 75 kD ladder is marked as a reference molecular weight, however, ladders used in SDS-PAGE are from globular proteins and hence are not directly comparable to unstructured ZIPPs. (B) Representative MALDI spectra for $(VPREG)_{80}$ and $(VPKEG)_{80}$ confirmed the molecular weight of the purified ZIPP constructs (MW=44.1 kDa, MW=41.8 kDa, respectively). (C) CD-Spectra of ZIPPs showed negative ellipticity in low wavelength and slightly positive ellipticity in higher wavelength, which is typical of a disordered structure like ELPs.
Figure 7C:
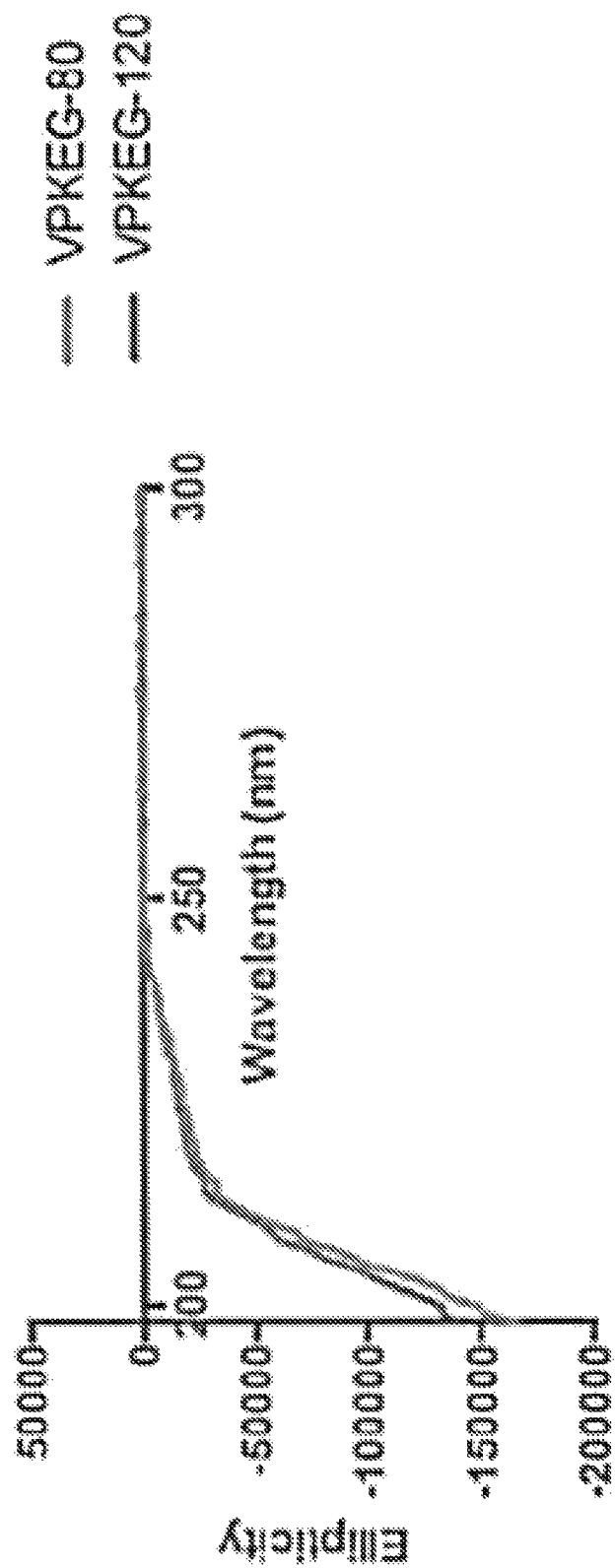

The thermally responsive property of ZiPPS enabled a simple non-chromatographic purification using ITC. The appearance of a single band in copper stained SDS-PAGE gel confirmed the purity of the product (FIG. 2A). Two different ZiPPs, $(VPKEG)_{80}$, (MW=44 kDa) and $(VPREG)_{80}$. (MW=42 kDa) are shown as representatives of purified products in FIG. 7A. The 50 kDa ladder is marked as a reference MW in the gel, however the ladder used in SDS gels is from globular proteins and hence is not directly comparable to unstructured ZiPPs. To confirm the purity and MW, we analyzed the purified product by MALDI-TOF. The MALDI spectrum showed the presence of ions at m/z values of 21 kDa and 42 kDa (peaks 1 and 2) for $(VPKEG)_{80}$ and m/z values of 22 kDa and 44 kDa (peaks 3 and 4) for $(VPREG)_{80}$ (FIG. 7B). The MALDI spectrum showed the presence of ions at m/z values of 20 kDa, 30 kDa, and 60.5 kDa for $(VPKDG)_{120}$ and m/z values of 21 kDa and 32 kDa and 63.8 kDa for $(VPRDG)_{120}$ (FIG. 2B), which confirmed the molecular weight of the purified ZiPP constructs (MW=60.5 kDa, MW=63.8 kDa respectively). We also confirmed the intrinsic disordered nature of the ZiPPs by using CD-Spectra. The CD-spectra in FIG. 2D and FIG. 7C showed negative ellipticity in low wavelength and slightly positive ellipticity in higher wave length, which is characteristic of a random-coil, which is typical of a disordered structure like ELPs and confirmed the unstructured nature of the polymer. Hydrodynamic radius was measured using Dynamic Light Scattering and showed well hydrated ZiPPs compared to ELP controls (FIG. 2C). Native PAGE gel showed that ZIPPs do not interact with albumin (FIG. 2E).

Example 3

In-Vivo Pharmacokinetic Study

Figure 3A:
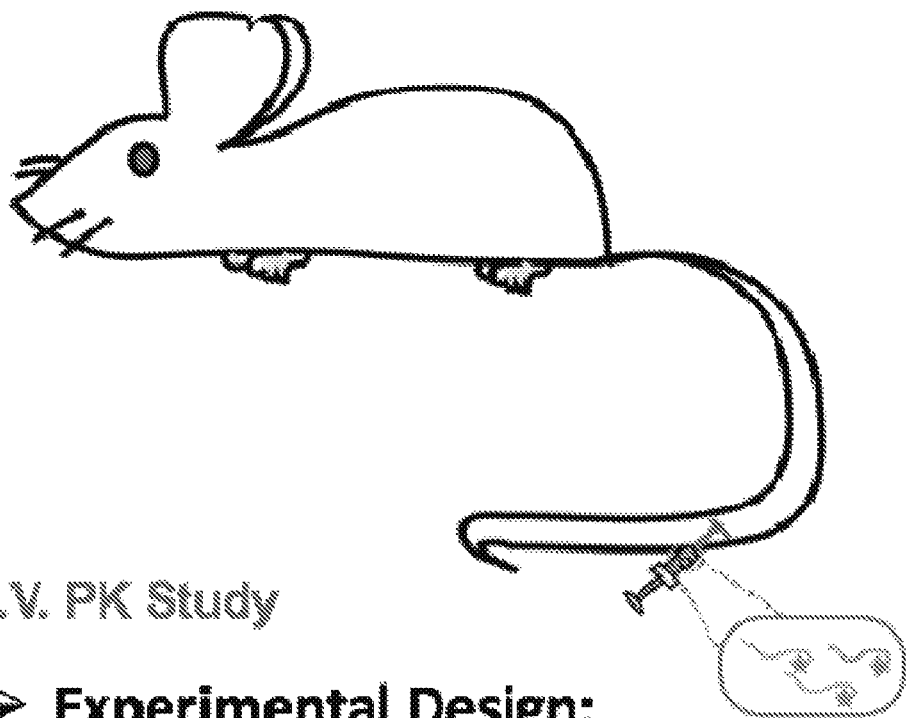
FIG. 3 shows the plasma pharmacokinetics of ELP (VPGAG) and ZiPPs when injected intravenously. (A) The experimental design. (B) Plasma concentrations as a function of time post-injection. (C) Area under the curve (AUC) for each conjugate. (D) Elimination half-life for each conjugate.
Figure 3B:
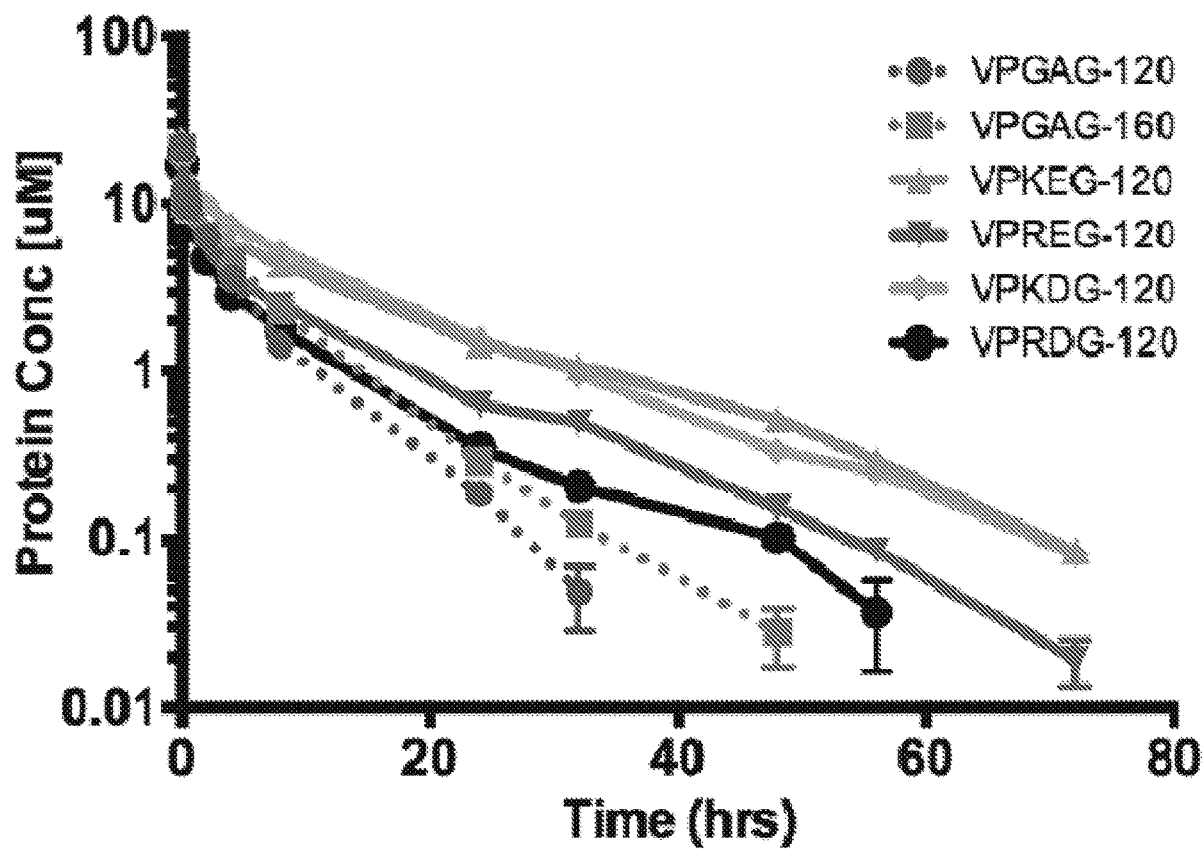
Figure 3C:
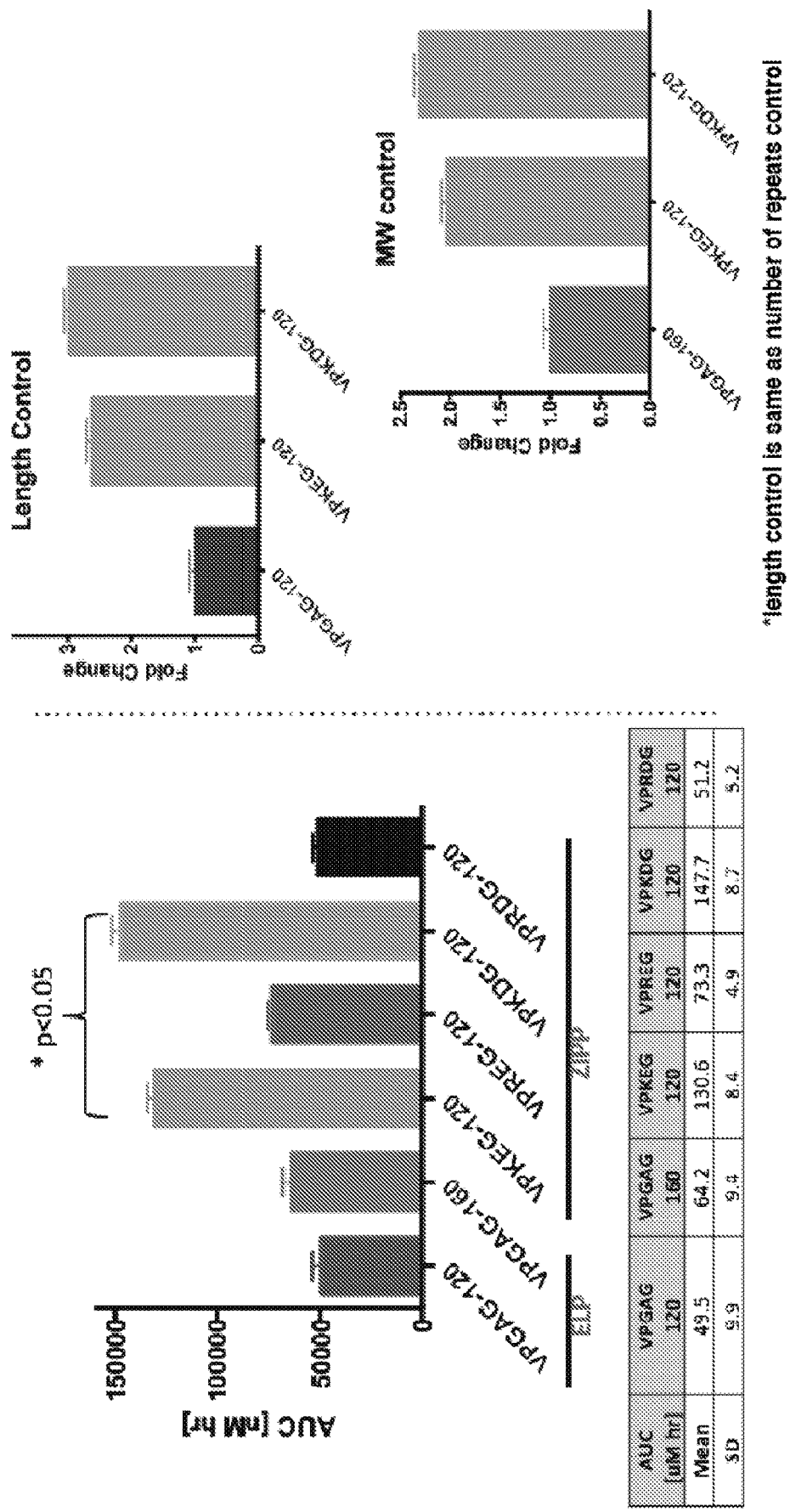
Figure 3D:
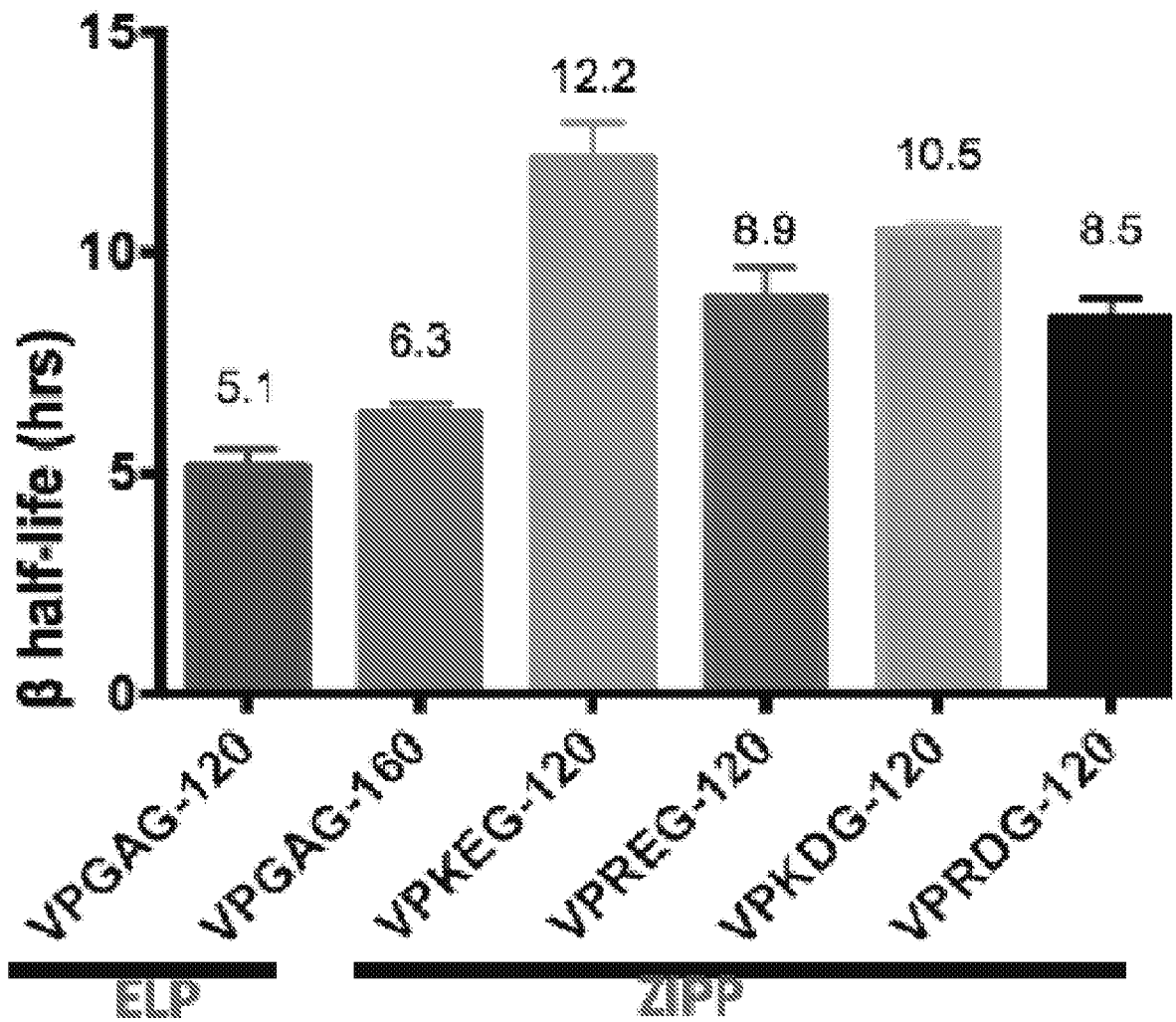
Figure 4A:
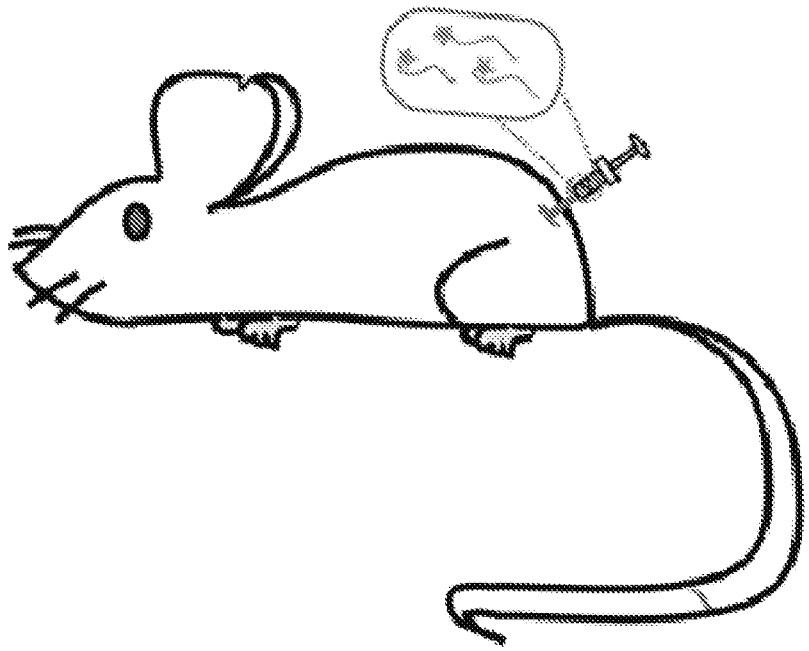
FIG. 4 shows the plasma pharmacokinetics of ELP (VP-GAG) and ZiPPs when injected subcutaneously. (A) The experimental design. (B) Plasma concentrations as a function of time post-injection. (C) AUC for each conjugate.
Figure 4B:
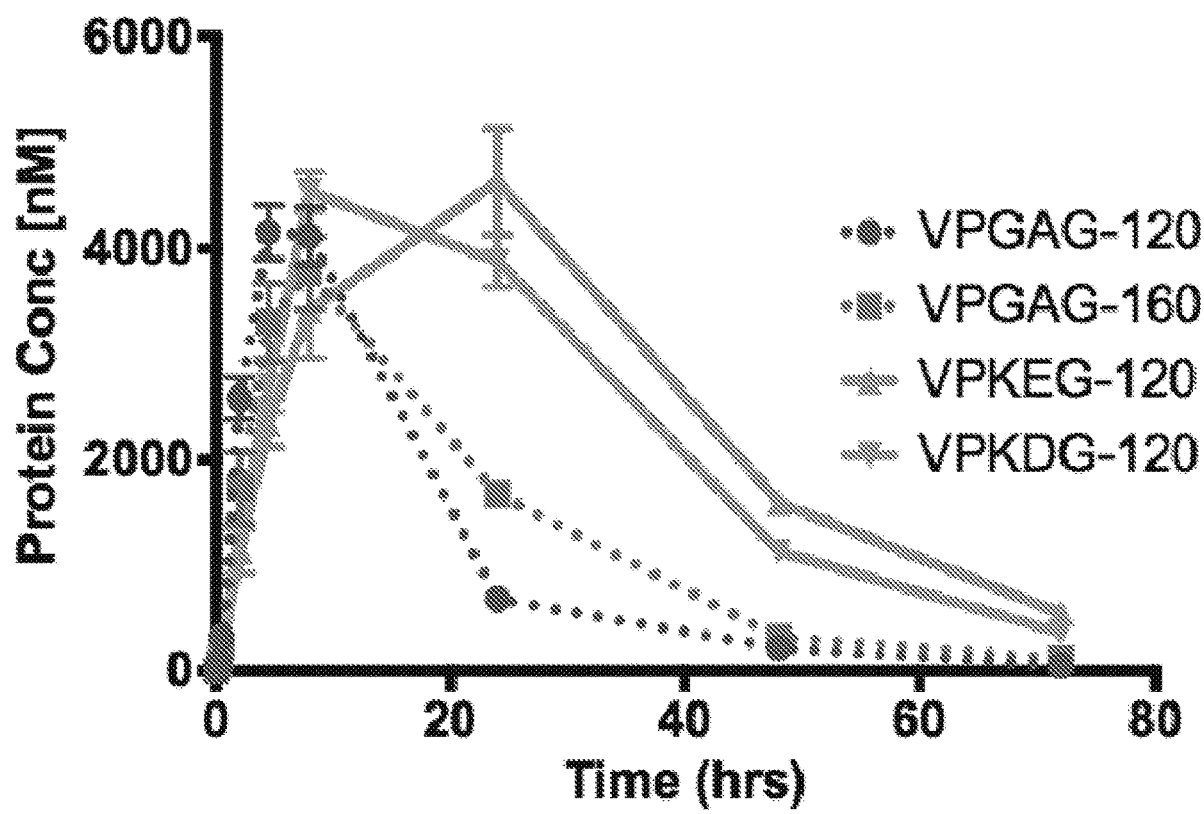
Figure 4C:
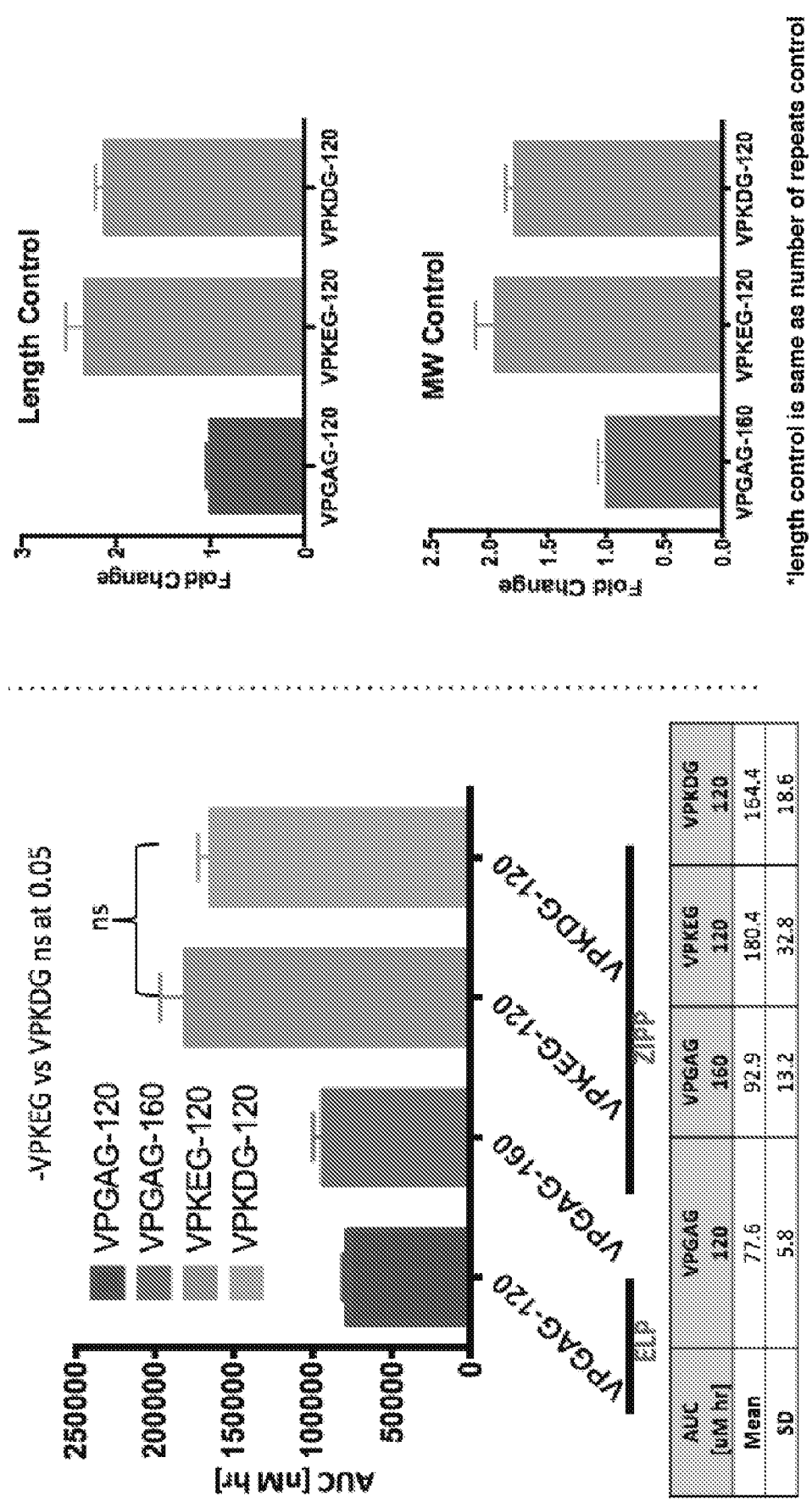

To determine the pharmacokinetic parameters of ZiPPs, the plasma concentration was tracked over a period of 72 hours following systemic administration in mice via tail vein injection or sub-cutaneous injection. An uncharged polymer with matched amino acid length was used as the control. The experimental design is shown in FIG. 3A and FIG. 4A. The polymers were fluorescently labeled with Alexa488 and injected into mice. Blood samples were collected at various time points up to 72 hours. ELP120 $(VPGAG)_{120}$ was used as a length control while ELP160 $(VPGAG)_{160}$ was used as a molecular weight control. FIG. 3B and FIG. 4B show the plasma polymer concentration as a function of time post-injection, which showed that incorporating a zwitterionic motif (specifically including K, D, and E for $X_1$ and $X_2$, respectively) imparted stealth property, which in return increased the circulation time of the polymer compared to uncharged ELPs. Plasma concentrations as a function of time post-injection showed that ZIPPs performed better than ELPs. These polymers followed a two compartmental model and thus the half-life and area under the curve was calculated using this model. A two-compartment model was fitted to the plasma polymer concentration, which yielded pharmacokinetic parameters area under the curve (AUC) (FIG. 3C and FIG. 4C) and elimination half-life (FIG. 3D). AUC was calculated as a measure of the total polymer exposure over the time course of the experiment. The AUC showed that VPKEG and VPKDG performed significantly better than uncharged ELP length controls as well as the molecular weight control. Data represent mean±SE, n=5 for FIG. 3C, and data represent mean±SE, n=3-4 for FIG. 4C. The terminal half-life of ZiPPs increased by 6 hours compared to that of VPGAG constructs (FIG. 3D). Moreover, the most descriptive pharmacokinetic parameter, the total cumulative blood exposure of the polymer, measured by area under the plasma concentration curve (AUC) for ZiPPs was about three times higher than that of the uncharged polypeptide, VPGAG of same chain length (FIG. 3C). The result showed that incorporating a zwitterionic motif and more specifically charged residues into the peptide polymer does play a significant role in improving the pharmacokinetics of the polymer.

Example 4

Characterization of Paclitaxel-ZiPP Conjugates

Figure 5A:
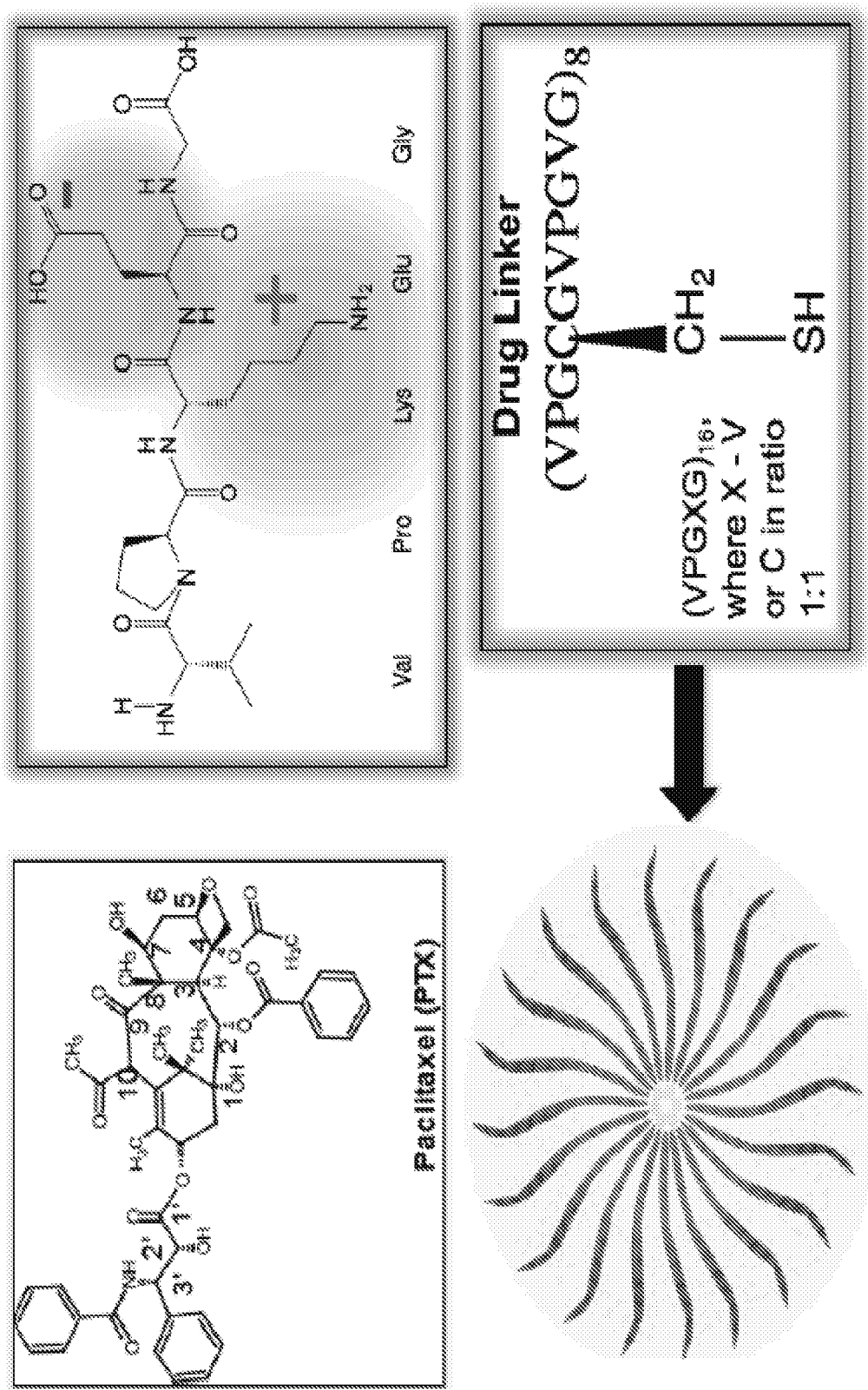
FIG. 5 shows the characterization of ZiPP-PTX conjugate. (A) Design schematics of ZiPP paclitaxel (PTX) nanoparticles. Paclitaxel was chemically conjugated to the 8 C-terminal residues via a pH sensitive linker. (B) Dynamic and static light data after PTX conjugation shows that ZiPPs self-assembled into micelles of 58 nm radius with aggregation number of 26 per micelle. The form factor ($\rho$)—calculated as Rg/Rh—was 0.82, which denotes formation of spherical micelles. MALDI-MS of ZiPP and ZiPP+PTX conjugate showed that there were 3.2-4 drugs per polymer chain. (C) Cell viability for ZiPP-PTX, ELP-PTX, and free PTX in MDA-MB-231 triple negative breast cancer cell line after 72 hours of treatment.
Figure 5B:
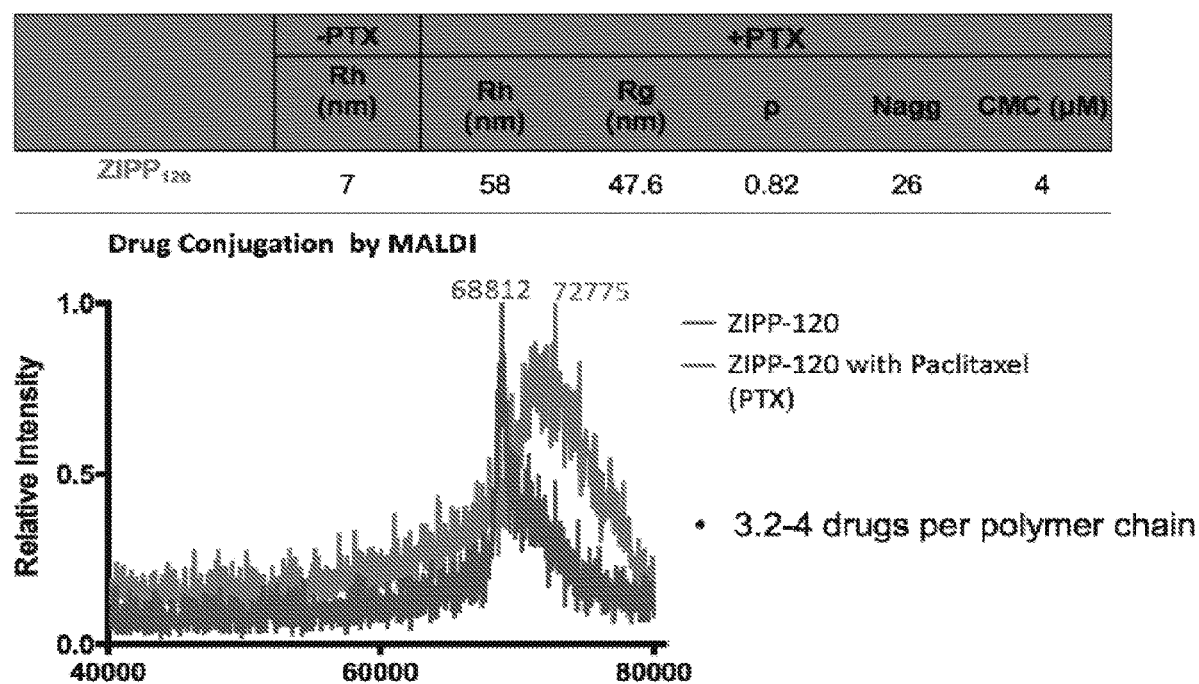

Paclitaxel (PTX) was chemically conjugated to $(VPGXG)_{16}$, with X-V or C, in a ratio 1:1, at a trailer at the C-terminus of 120 repeats of the VPKEG pentapeptide unit. Paclitaxel was chemically conjugated to the 8 C-terminal residues via a pH sensitive linker. The design is shown in FIG. 5A. The polymer drug conjugate was purified using Amicon Ultra-15 Centrifugal Filter Units (MWCO: 10 kDa; Millipore; Billerica, Mass.) and the purified product was run on HPLC to confirm the absence of unreacted free drugs. The HPLC chromatogram confirmed the purity of the polymer-drug conjugate with negligible amount of free drugs. Purified ZiPP-PTX conjugate had 3.2-4 drugs per polymer chain as confirmed by the difference in MW calculated between the parent ZiPP polymer chain and ZiPP-PTX conjugate using MALDI-TOF spectra (FIG. 5B). Moreover, Dynamic Light Scattering measurement indicated that after PTX conjugation, ZiPPs indeed spontaneously self-assembled into nanoparticles of hydrodynamic radius (Rh) of 58 nm. They self-assembled into micelles of 58 nm radius with aggregation number of 26 per micelle. The form factor (ρ)—calculated as Rg/Rh—was 0.82, which denotes formation of spherical micelles.

Example 5

In Vitro Anti-Tumor Efficacy of ZiPP-PTX Conjugates

Figure 5C:
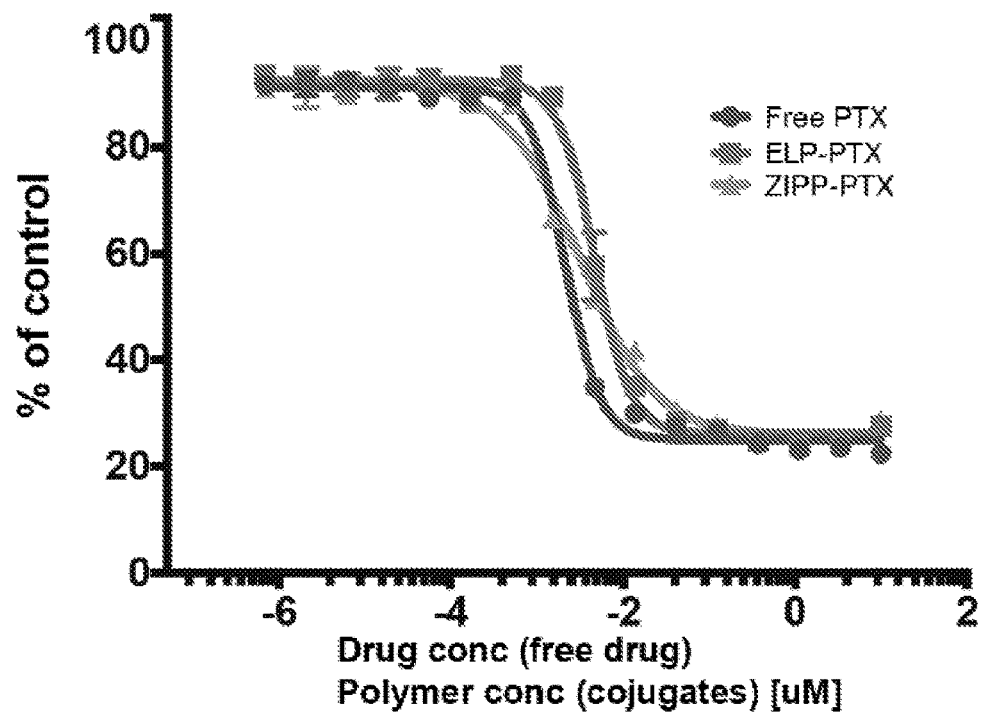

The in vitro cytotoxicity of Zipp-PTX was measured by looking at the cell viability over a range of concentrations as a function of time. MDA-MB-231 was used as the model, a human triple negative breast cancer cell line. After 72 hours of drug treatment, the proliferation of MDA-MB-231 cells was inhibited compared to the control (no drug) (FIG. 5C). Moreover, the inhibition was comparable to that of free drug. The $IC_{50}$ value for free drug was around 2 nM while that of ZiPP-PTX was 12.4 nM (concentration in terms of the drug). The $IC_{50}$ value for ZiPP-PTX was 6 times higher than that for free drug, but such result is expected in an in-vitro environment, where free drugs can easily diffuse in and out of the cells through drug transporters, while PTX from the drug-polymer conjugate only gets released once it is inside of the endosome. This process is slow because the nanoparticles are uptaken via endocytosis and the drug gets released after the nanoparticles travel to the late endosomes where pH is low. This low pH triggers the release of PTX from ZiPP. These results are encouraging as they indicate that the PTX-polymer conjugate is stable and is potent enough to take to in-vivo platform. $IC_{50}$ values represented the concentration of the drug that reduced cell viability by 50%.

Example 6

ZiPP-Tn3 Conjugates

Figure 6A:
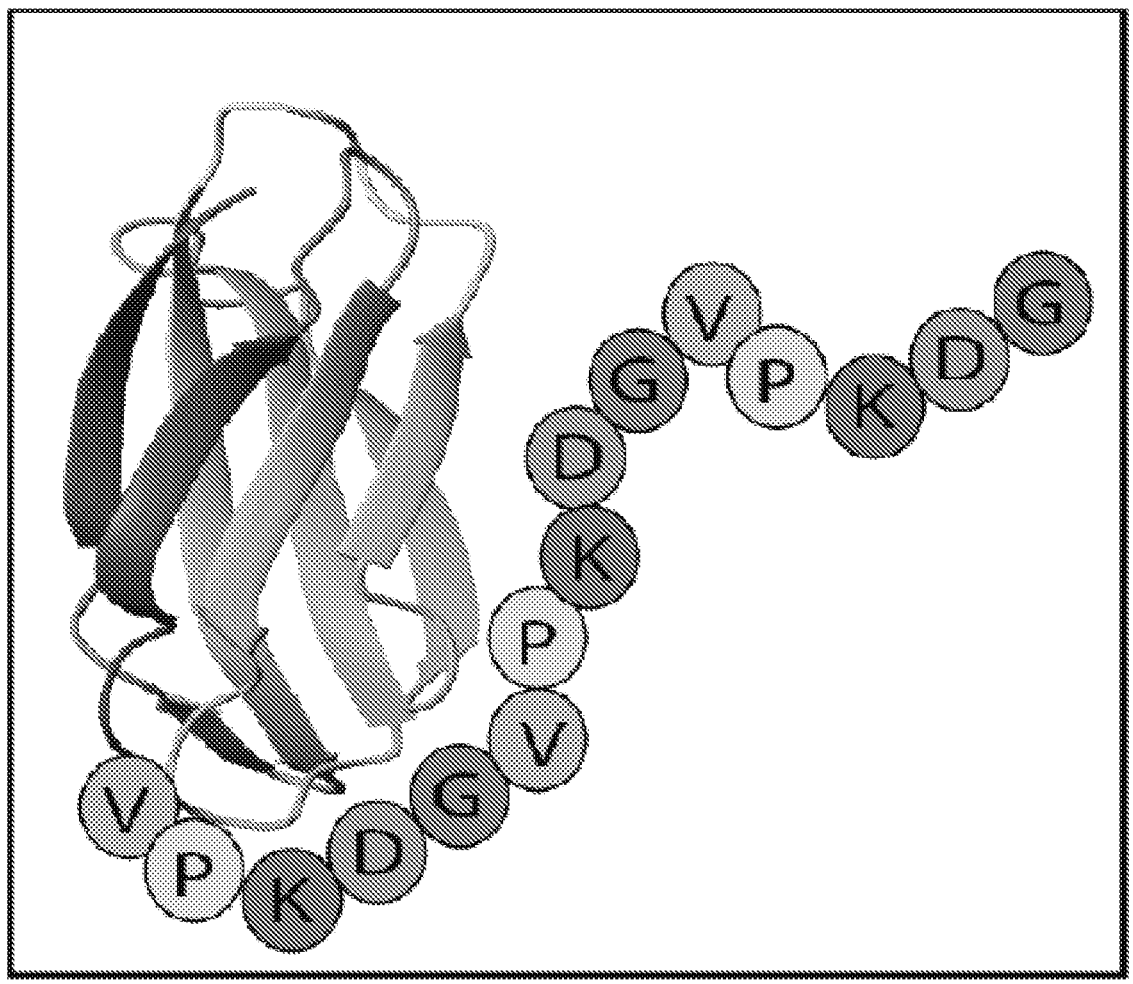
FIG. 6 shows Zippylated proteins. (A) Design overview for ZiPP fusion protein with $(Tn3)_6$. (B) SDS-PAGE analysis of affinity purified samples of $(Tn3)_6$ with various lengths of ZiPP that were recombinantly expressed in *E. coli*. (C) Cytotoxicity assay against Colo205 (colon cancer cell) and calculated $IC_{50}$ values.
Figure 6B:
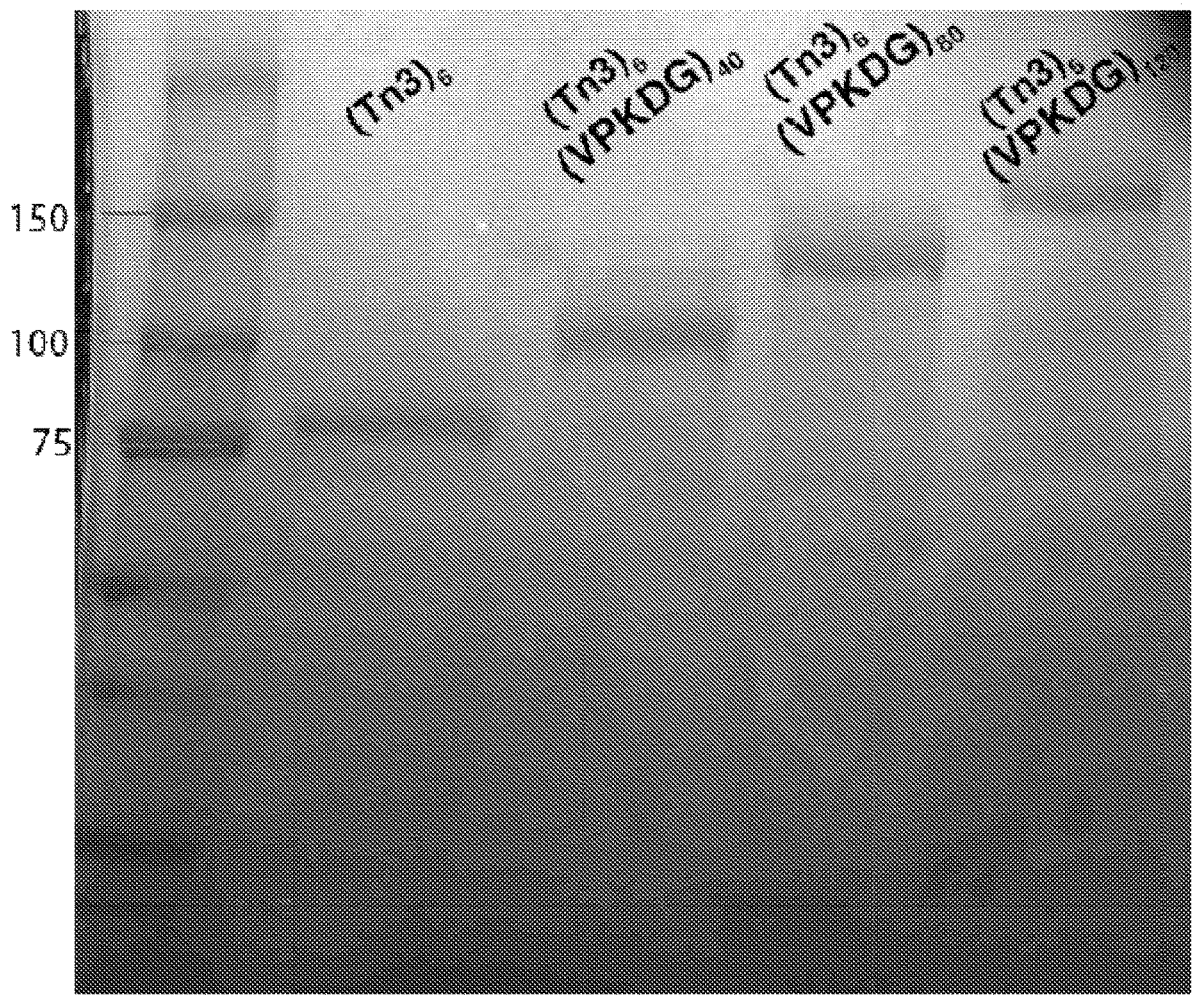
Figure 6C:
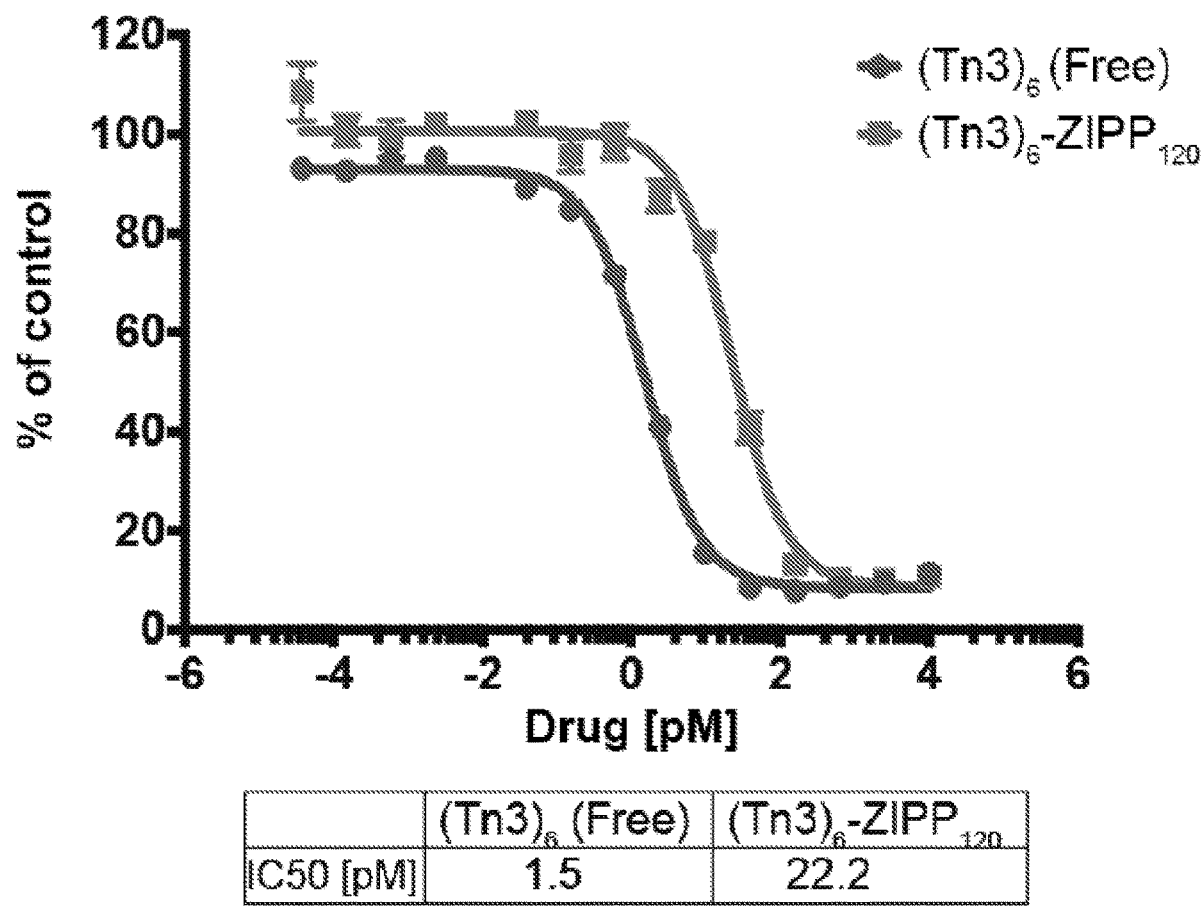

Multivalent scaffold protein (Tn3) is a superagonist of TNF-related apoptosis-including ligand receptors 2 (TRAIL2) and was picked as the protein to attached to a ZiPP. The design overview of the fusion protein is shown in FIG. 6A. Superagonist of TRAIL2 was chosen because activation of TRAILR2 can induce apoptosis in a variety of human cancers, and hence has a potential for cancer therapeutics. $(Tn3)_6$ represents 6 tandem repeats of the monomer Tn3 unit, which was engineered by MedImmune to bind to TRAIL2 with high affinity. $(Tn3)_6$ with various lengths of ZiPP was recombinantly expressed in E. coli. SDS-PAGE analysis of affinity purified samples are shown in FIG. 6B. A cytotoxicity assay against Colo205 (colon cancer cell) showed that the fusion proteins were highly cytotoxic and their potency was comparable to free protein ($(Tn3)_6$ without ZIPP attached), as shown in FIG. 6C. The $IC_{50}$ values represented the concentration of the drug that reduced cell viability by 50%.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A conjugate comprising: (a) a polypeptide comprising one or more charged motifs, each charged motif independently having an amino acid sequence consisting of SEQ ID NO: 1 ($VPX_1X_2G$), wherein $X_1$ is a negatively or positively charged amino acid, and wherein $X_2$ is the other of a negatively or positively charged amino acid; and (b) one or more drug molecules attached to the polypeptide.

Clause 2. The conjugate of clause 1, wherein the polypeptide comprises a plurality of charged motifs.

Clause 3. The conjugate of clause 2, wherein the plurality of charged motifs is repeated in tandem.

Clause 4. The conjugate of clause any one of the preceding clauses, wherein the polypeptide further comprises one or more uncharged motifs, each uncharged motif independently having an amino acid sequence consisting of SEQ ID NO: 3 (VPGXG), wherein X is any amino acid except proline.

Clause 5. The conjugate of clause 4, wherein the polypeptide comprises a plurality of uncharged motifs.

Clause 6. The conjugate of clause 5, wherein the plurality of uncharged motifs is repeated in tandem.

Clause 7. The conjugate of any one of clauses 4-6, wherein one or more uncharged motifs are positioned between at least two adjacent charged motifs of the polypeptide.

Clause 8. The conjugate of clause 1, wherein the polypeptide comprises the amino acid sequence of SEQ ID NO: 2 $(VPX_1X_2G)_n$, wherein $X_1$ is a negatively or positively charged amino acid, $X_2$ is the other of a negatively or positively charged amino acid, and n is an integer greater than or equal to 1.

Clause 9. The conjugate of clause 4, wherein the polypeptide comprises the amino acid sequence of SEQ ID NO: 4 $(VPGXG)_n$, wherein X is any amino acid except proline, and n is an integer greater than or equal to 1.

Clause 10. The conjugate of clause 4, wherein the polypeptide comprises the amino acid sequence of SEQ ID NO: 5 $(VPX_1X_2G)_n(VPGXG)_m$, wherein $X_1$ is a negatively or positively charged amino acid, $X_2$ is the other of a negatively or positively charged amino acid, X is any amino acid except proline, and n and m are independently an integer greater than or equal to 1.

Clause 11. The conjugate of clause 4, wherein the polypeptide comprises the amino acid sequence of SEQ ID NO: 6 $(VPGXG)_m(VPX_1X_2G)_n$, wherein $X_1$ is a negatively or positively charged amino acid, $X_2$ is the other of a negatively or positively charged amino acid, X is any amino acid except proline, and n and m are independently an integer greater than or equal to 1.

Clause 12. The conjugate of clause 4, wherein the polypeptide comprises the amino acid sequence of SEQ ID NO: 7 $\{(VPX_1X_2G)(VPGXG)\}_b$, wherein $X_1$ is a negatively or positively charged amino acid, $X_2$ is the other of a negatively or positively charged amino acid, X is any amino acid except proline, and b is an integer greater than or equal to 1.

Clause 13. The conjugate of any one of clauses 1-12, wherein $X_1$ is a negatively charged amino acid, and wherein $X_2$ is a positively charged amino acid.

Clause 14. The conjugate of any one of clauses 1-12, wherein $X_1$ is a positively charged amino acid, and wherein $X_2$ is a negatively charged amino acid.

Clause 15. The conjugate of any one of the preceding clauses, wherein the negatively charged amino acid is independently selected from glutamatic acid and aspartic acid.

Clause 16. The conjugate of any one of the preceding clauses, wherein the positively charged amino acid is independently selected from lysine and arginine.

Clause 17. The conjugate of any one of clauses 4-16, wherein X is any amino acid except proline.

Clause 18. The conjugate of clause 17, wherein X is selected from arginine, histidine, lysine, aspartic acid, glutamic acid, serine, threonine, asparagine, glutamine, cysteine, selenocysteine, glycine, alanine, valine, leucine, isoleucine, methionine, phenylalanine, tyrosine, and tryptophan.

Clause 19. The conjugate of clause 18, wherein X is selected from glycine and valine.

Clause 20. The conjugate of any one of the preceding clauses, wherein the polypeptide further comprises a linker.

Clause 21. The conjugate of clause 20, wherein the linker comprises one or more cysteines.

Clause 22. The conjugate of any one of clauses 20-21, wherein the linker comprises an amino acid sequence selected from SEQ ID NO: (GGC), SEQ ID NO: ((GGC)$_8$), SEQ ID NO: ((G$_4$S)$_3$), and SEQ ID NO: ((VPGXG)$_{16}$ wherein X is valine or cysteine present in a ratio of 1:1).

Clause 23. The conjugate of any one of clauses 20-22, wherein the linker is positioned at the C-terminus, at the N-terminus, or a both C- and N-termini of the polypeptide.

Clause 24. The conjugate of any one of clauses 20-23, wherein the one or more drug molecules are attached to the polypeptide via the linker.

Clause 25. The conjugate of any one of clauses 20-24, wherein the drug molecule is attached to the polypeptide through a thiol reactive group in the linker.

Clause 26. The conjugate of any one of the preceding clauses, wherein the one or more drug molecules are selected from a small molecule, nucleotide, polynucleotide, peptide, protein, carbohydrate, and a combination thereof.

Clause 27. The conjugate of clause 26, wherein the drug molecule comprises a small molecule.

Clause 28. The conjugate of clause 26, wherein the drug molecule comprises a protein.

Clause 29. The conjugate of any one of clauses 1-25, wherein the drug molecule comprises a cancer therapeutic.

Clause 30. The conjugate of any one of clauses 1-25, wherein the drug molecule comprises an antibody.

Clause 31. The conjugate of any one of clauses 1-25, wherein the drug molecule comprises a paclitaxel.

Clause 32. The conjugate of any one of clauses 1-25, wherein the drug molecule comprises Tn3 (TRAIL superagonist).

Clause 33. The conjugate of any one of the preceding clauses, wherein the conjugate is prepared for administration to a subject.

Clause 34. The conjugate of any one of the preceding clauses, wherein the polypeptide of the conjugate is recombinantly expressed.

Clause 35. The conjugate of clause 28, wherein the conjugate is recombinantly expressed.

Clause 36. A composition comprising the conjugate of any one of the preceding clauses.

Clause 37. A polynucleotide encoding the polypeptide of any one of clauses 1-35.

Clause 38. A polynucleotide encoding the conjugate of clause 28.

Clause 39. A vector comprising the polynucleotide of clause 37 or 38.

Clause 40. A method of delivering a drug molecule to a subject, the method comprising administering the conjugate of any one of clauses 1-35 to the subject.

Clause 41. A method of treating a subject having a disease or disorder, the method comprising administering the conjugate of any one of clauses 1-35 to the subject.

Clause 42. A method of determining the presence of a target in a sample, the method comprising: contacting the sample with the conjugate of any one of clauses 1-35 under conditions to allow a complex to form between the drug molecule and the target in the sample; and detecting the presence of the complex, wherein presence of the complex is indicative of the target in the sample.

Clause 43. The method of clause 42, wherein the sample is obtained from a subject and the method further comprises diagnosing a disease, prognosticating, or assessing the efficacy of a treatment of the subject.

Clause 44. The method of clause 43, wherein when the method further comprises assessing the efficacy of a treatment of the subject, then the method further comprises modifying the treatment of the subject as needed to improve efficacy.

Clause 45. A method of diagnosing a disease in a subject, the method comprising: contacting a sample from the subject with the conjugate of any one of clauses 1-35 under conditions to allow a complex to form between the drug molecule and a target in the sample; determining the level of the target in the sample, wherein level of the complex is indicative of the level of the target in the sample; and comparing the level of the target in the sample to a control level of the target, wherein a level of the target different from the control level indicates disease in the subject.

Clause 46. The method of clause 45, wherein the control level corresponds to the level in the subject at a time point before or during the period when the subject has begun treatment, and wherein the sample is taken from the subject at a later time point.

Clause 47. The method of clause 45, wherein the sample is taken from the subject at a time point during the period when the subject is undergoing treatment, and wherein the control level corresponds to a disease-free level or to the level at a time point before the period when the subject has begun treatment.

Clause 48. The method of any one of clauses 45-47, the method further comprising modifying the treatment or administering a different treatment to the subject when the treatment is determined to be ineffective in treating the disease.

Clause 49. The method of any one of clauses 40-48, wherein the conjugate is labeled with a reporter.

Clause 50. The method of any one of clauses 40-49, wherein the conjugate is administered to the subject intravenously, intraarterially, intraperitoneally, or intratumorally.

Clause 51. The method of any one of clauses 40-50, wherein the conjugate has reduced antigenicity relative to the drug molecule conjugated to polyethylene glycol (PEG).

Clause 52. The method of any one of clauses 40-50, wherein the conjugate has reduced immunogenicity relative to the drug molecule conjugated to polyethylene glycol (PEG).

Clause 53. The method of any one of clauses 40-52, wherein the disease is selected from cancer, metabolic disease, autoimmune disease, cardiovascular disease, and orthopedic disorder.

Clause 54. The method of clause 53, wherein the disease comprises cancer.

Clause 55. The method of clause 54, wherein the cancer is selected from breast cancer, colorectal cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer.

Clause 56. The method of clause 55, wherein the cancer comprises breast cancer.

Sequences

SEQ ID NO: 1
VPX$_1$X$_2$G, wherein X$_1$ is a negatively or positively charged amino acid, and wherein X$_2$ is the other of a negatively or positively charged amino acid.

SEQ ID NO: 2
(VPX$_1$X$_2$G)$_n$, wherein X$_1$ is a negatively or positively charged amino acid, X$_2$ is the other of a negatively or positively charged amino acid, and n is an integer greater than or equal to 1.

SEQ ID NO: 3
VPGXG, wherein X is any amino acid except proline.

SEQ ID NO: 4
(VPGXG)$_n$, wherein X is any amino acid except proline, and n is an integer greater than or equal to 1.

SEQ ID NO: 5
(VPX$_1$X$_2$G)$_n$(VPGXG)$_m$, wherein X$_1$ is a negatively or positively charged amino acid, X$_2$ is the other of a negatively or positively charged amino acid, X is any amino acid except proline, and n and m are independently an integer greater than or equal to 1.

SEQ ID NO: 6
(VPGXG)$_m$(VPX$_1$X$_2$G)$_n$, wherein X$_1$ is a negatively or positively charged amino acid, X$_2$ is the other of a negatively or positively charged amino acid, X is any amino acid except proline, and n and m are independently an integer greater than or equal to 1.

SEQ ID NO: 7
{(VPX$_1$X$_2$G)(VPGXG)}$_b$, wherein X$_1$ is a negatively or positively charged amino acid, X$_2$ is the other of a negatively or positively charged amino acid, X is any amino acid except proline, and b is an integer greater than or equal to 1.

SEQ ID NO: 8
GGC

SEQ ID NO: 9
(GGC)$_8$

SEQ ID NO: 10
(G$_4$S)$_3$

SEQ ID NO: 11
(VPGXG)$_{16}$ wherein X is valine or cysteine present in a ratio of 1:1.

Example polypeptide
SEQ ID NO: 12
V P K D G V P K D G V P K D G V P K D G V P K D G Polynucleotide encoding example polypeptide
SEQ ID NO: 13
GTC CCG aaa gac GGT GTT CCG aag gac GGC GTG CCT aaa gat GGT GTT CCG aag gac GGG GTG CCA aaa gat GGG

---

We claim:

1. A conjugate comprising:
   (a) a polypeptide comprising SEQ ID NO: 2 (VPX$_1$X$_2$G)$_n$, wherein X$_1$ is a negatively or positively charged amino acid, X$_2$ is the other of a negatively or positively charged amino acid, and n is an integer from about 50 to about 500, wherein the negatively charged amino acid is independently selected from glutamic acid and aspartic acid, and the positively charged amino acid is independently selected from lysine and arginine, and wherein SEQ ID NO: 2 repeats in series about 50 to about 500 times; and
   (b) one or more drug molecules attached to the polypeptide, wherein the one or more drug molecules are selected from a cancer therapeutic, nucleotide, polynucleotide, peptide, protein, carbohydrate, antibody, and a combination thereof.

2. The conjugate of claim 1, wherein the polypeptide further comprises one or more uncharged motifs, each uncharged motif independently having an amino acid sequence consisting of SEQ ID NO: 3 (VPGXG), wherein X is any amino acid except proline.

3. The conjugate of claim 2, wherein the polypeptide comprises a plurality of uncharged motifs.

4. The conjugate of claim 3, wherein the plurality of uncharged motifs is repeated in tandem.

5. The conjugate of claim 2, wherein one or more uncharged motifs are positioned between at least two adjacent charged motifs of the polypeptide.

6. The conjugate of claim 2, wherein the polypeptide comprises the amino acid sequence of SEQ ID NO: 5 (VPX$_1$X$_2$G)$_n$(VPGXG)$_m$, wherein:
   X$_1$ is a negatively or positively charged amino acid, X$_2$ is the other of a negatively or positively charged amino acid, wherein the negatively charged amino acid is independently selected from glutamic acid and aspartic acid, and the positively charged amino acid is independently selected from lysine and arginine;
   X is any amino acid except proline;
   n is an integer from about 50 to about 500; and
   m is an integer greater than or equal to 1.

7. The conjugate of claim 2, wherein the polypeptide comprises the amino acid sequence of SEQ ID NO: 6 (VPGXG)$_m$(VPX$_1$X$_2$G)$_n$, wherein:
   X$_1$ is a negatively or positively charged amino acid, X$_2$ is the other of a negatively or positively charged amino acid, wherein the negatively charged amino acid is independently selected from glutamic acid and aspartic acid, and the positively charged amino acid is independently selected from lysine and arginine;

X is any amino acid except proline;

n is an integer from about 50 to about 500; and m is an integer greater than or equal to 1.

8. The conjugate of claim 2, wherein the polypeptide comprises the amino acid sequence of SEQ ID NO: 7 {(VPX$_1$X$_2$G)(VPGXG)}$_b$, wherein:

X$_1$ is a negatively or positively charged amino acid, X$_2$ is the other of a negatively or positively charged amino acid, wherein the negatively charged amino acid is independently selected from glutamic acid and aspartic acid, and the positively charged amino acid is independently selected from lysine and arginine;

X is any amino acid except proline; and b is an integer greater than or equal to 1.

9. The conjugate of claim 1, wherein the polypeptide further comprises a linker, and wherein the one or more drug molecules are attached to the polypeptide via the linker.

10. The conjugate of claim 9, wherein the linker comprises one or more cysteines.

11. The conjugate of claim 9, wherein the linker comprises an amino acid sequence selected from SEQ ID NO: 8 (GGC), SEQ ID NO: 9 ((GGC)$_8$), SEQ ID NO: 10 ((G$_4$S)$_3$), and SEQ ID NO: 11 ((VPGXG)$_{16}$) wherein X is valine or cysteine present in a ratio of 1:1.

12. The conjugate of claim 9, wherein the drug molecule is attached to the polypeptide through a thiol reactive group in the linker.

13. The conjugate of claim 1, wherein the drug molecule is a cancer therapeutic.

14. The conjugate of claim 1, wherein the drug molecule is paclitaxel.

15. A method of treating a subject having a disease or disorder, the method comprising administering the conjugate of claim 1 to the subject, wherein the disease or disorder is a cancer, a metabolic disease, an autoimmune disease, a cardiovascular disease, or an orthopedic disorder.

16. The method of claim 15, wherein the disease or disorder is cancer selected from breast cancer, colorectal cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer.

17. The conjugate of claim 2, wherein the polypeptide further comprises a linker, and wherein the one or more drug molecules are attached to the polypeptide via the linker.

18. The conjugate of claim 17, wherein the linker comprises one or more cysteines.

19. The conjugate of claim 17, wherein the linker comprises an amino acid sequence selected from SEQ ID NO: 8 (GGC), SEQ ID NO: 9 ((GGC)$_8$), SEQ ID NO: 10 ((G$_4$S)$_3$), and SEQ ID NO: 11 ((VPGXG)$_{16}$) wherein X is valine or cysteine present in a ratio of 1:1.

20. The conjugate of claim 17, wherein the drug molecule is attached to the polypeptide through a thiol reactive group in the linker.

21. The conjugate of claim 1, wherein the drug molecule is a protein.

22. The conjugate of claim 1, wherein the drug molecule is an antibody.

23. The conjugate of claim 1, wherein the drug molecule is Tn$_3$ TRAIL superagonist.

* * * * *

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (3)..(3)
<223> OTHER INFORMATION: negatively or positively charged amino acid
<220> FEATURE:
<221> NAME/KEY: X
<222> LOCATION: (4)..(4)
<223> OTHER INFORMATION: other negatively or positively charged amino
      acid

<400> SEQUENCE: 1

Val Pro Xaa Xaa Gly
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (3)..(3)
<223> OTHER INFORMATION: negatively or positively charged amino acid
<220> FEATURE:
<221> NAME/KEY: X
<222> LOCATION: (4)..(4)
<223> OTHER INFORMATION: other negatively or positively charged amino
      acid
```

```
-continued

<400> SEQUENCE: 2

Val Pro Xaa Xaa Gly
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (4)..(4)
<223> OTHER INFORMATION: any amino acid except proline

<400> SEQUENCE: 3

Val Pro Gly Xaa Gly
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (4)..(4)
<223> OTHER INFORMATION: any amino acid except proline

<400> SEQUENCE: 4

Val Pro Gly Xaa Gly
1               5

<210> SEQ ID NO 5
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (3)..(3)
<223> OTHER INFORMATION: negatively or positively charged amino acid
<220> FEATURE:
<221> NAME/KEY: X
<222> LOCATION: (4)..(4)
<223> OTHER INFORMATION: other negatively or positively charged amino
      acid
<220> FEATURE:
<221> NAME/KEY: X
<222> LOCATION: (9)..(9)
<223> OTHER INFORMATION: any amino acid except proline

<400> SEQUENCE: 5

Val Pro Xaa Xaa Gly Val Pro Gly Xaa Gly
1               5                   10

<210> SEQ ID NO 6
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (4)..(4)
<223> OTHER INFORMATION: any amino acid except proline
<220> FEATURE:
<221> NAME/KEY: X
<222> LOCATION: (8)..(8)
```

<223> OTHER INFORMATION: negatively or positively charged amino acid
<220> FEATURE:
<221> NAME/KEY: X
<222> LOCATION: (9)..(9)
<223> OTHER INFORMATION: other negatively or positively charged amino
      acid

<400> SEQUENCE: 6

Val Pro Gly Xaa Gly Val Pro Xaa Xaa Gly
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (3)..(3)
<223> OTHER INFORMATION: negatively or positively charged amino acid
<220> FEATURE:
<221> NAME/KEY: X
<222> LOCATION: (4)..(4)
<223> OTHER INFORMATION: other negatively or positively charged amino
      acid
<220> FEATURE:
<221> NAME/KEY: X
<222> LOCATION: (9)..(9)
<223> OTHER INFORMATION: any amino acid except proline

<400> SEQUENCE: 7

Val Pro Xaa Xaa Gly Val Pro Gly Xaa Gly
1               5                   10

<210> SEQ ID NO 8
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 8

Gly Gly Cys
1

<210> SEQ ID NO 9
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 9

Gly Gly Cys Gly Gly Cys Gly Gly Cys Gly Gly Cys Gly Gly Cys Gly
1               5                   10                  15

Gly Cys Gly Gly Cys Gly Gly Cys
            20

<210> SEQ ID NO 10
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 10

Gly Gly Gly Gly Ser Gly Gly Gly Gly Ser Gly Gly Gly Gly Ser
1               5                   10                  15

```
<210> SEQ ID NO 11
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (4)..(4)
<223> OTHER INFORMATION: valine or cysteine present in a ratio of 1:1

<400> SEQUENCE: 11

Val Pro Gly Xaa Gly
1               5

<210> SEQ ID NO 12
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 12

Val Pro Lys Asp Gly Val Pro Lys Asp Gly Val Pro Lys Asp Gly Val
1               5                   10                  15

Pro Lys Asp Gly Val Pro Lys Asp Gly
            20                  25

<210> SEQ ID NO 13
<211> LENGTH: 75
<212> TYPE: DNA
<213> ORGANISM: Artificial sequence
<220> FEATURE:
<223> OTHER INFORMATION: Synthetic polynucleotide

<400> SEQUENCE: 13
gtcccgaaag acgtgttcc gaaggacggc gtgcctaaag atggtgttcc gaaggacggg      60
gtgccaaaag atggg                                                      75
```